US011058820B2

(12) United States Patent
Cereda et al.

(10) Patent No.: US 11,058,820 B2
(45) Date of Patent: Jul. 13, 2021

(54) DRUG DELIVERY DEVICE

(71) Applicant: OVAL MEDICAL TECHNOLOGIES LIMITED, Cambridge (GB)

(72) Inventors: Valerio Lelio Cereda, Cambridge (GB); Ralph George Lamble, Cambridge (GB); Jonathan Lawson, Cambridge (GB); Michael Charles Savill, Huntingdon (GB); Susanna Elizabeth McRobert White, Cambridge (GB); Martyn James Young, Warwick (GB); Matthew Egerton Young, Cambridge (GB)

(73) Assignee: OVAL MEDICAL TECHNOLOGIES LIMITED, Cambridge (GB)

(*) Notice: Subject to any disclaimer, the term of this patent is extended or adjusted under 35 U.S.C. 154(b) by 222 days.

(21) Appl. No.: 16/228,012

(22) Filed: Dec. 20, 2018

(65) Prior Publication Data
US 2019/0117893 A1    Apr. 25, 2019

Related U.S. Application Data

(63) Continuation of application No. 14/908,439, filed as application No. PCT/GB2014/052282 on Jul. 25, 2014, now Pat. No. 10,207,051.

(30) Foreign Application Priority Data

Aug. 1, 2013    (GB) .................................... 1313782

(51) Int. Cl.
*A61M 5/20* (2006.01)
*A61M 5/50* (2006.01)
(Continued)

(52) U.S. Cl.
CPC ........ *A61M 5/2033* (2013.01); *A61M 5/3157* (2013.01); *A61M 5/3202* (2013.01);
(Continued)

(58) Field of Classification Search
CPC .............. A61M 5/3157; A61M 5/3202; A61M 2205/581
See application file for complete search history.

(56) References Cited

U.S. PATENT DOCUMENTS 2,551,339 A     5/1951  George et al.
5,584,815 A *  12/1996  Pawelka ................. A61M 5/19
                                                              604/135

(Continued)

FOREIGN PATENT DOCUMENTS

CN      102316918 A     1/2012
CN      102470212 A     5/2012
(Continued)

OTHER PUBLICATIONS

"Definition of Sensor", Merriam-Webster, https://www.merriam-webster.com/dictionary/sensor. (2020) (Year: 2020).*
(Continued)

*Primary Examiner* — Nathan R Price
*Assistant Examiner* — Tasnim Mehjabin Ahmed
(74) *Attorney, Agent, or Firm* — Lando & Anastasi, LLP

(57) ABSTRACT

There is provided drug delivery devices comprising a drug container assembly with a needle and automatic needle insertion and drug delivery mechanisms. Aspects of the devices described include a noise-generation mechanism to indicate the completion of drug delivery, a mechanism for triggering drug delivery following needle insertion, front-end activation of the device and a safety mechanism for covering the needle after use and methods of assembly of the devices.

19 Claims, 46 Drawing Sheets

(51) Int. Cl.
*A61M 5/31* (2006.01)
*A61M 5/315* (2006.01)
*A61M 5/32* (2006.01)
*A61M 5/36* (2006.01)

(52) U.S. Cl.
CPC ............ *A61M 5/3204* (2013.01); *A61M 5/36* (2013.01); *A61M 5/50* (2013.01); *A61M 2005/3109* (2013.01); *A61M 2205/581* (2013.01)

(56) References Cited

U.S. PATENT DOCUMENTS

| | | | |
|---|---|---|---|
| 5,980,495 | A | 11/1999 | Heinz et al. |
| 6,485,474 | B1 | 11/2002 | Heinz et al. |
| 7,641,636 | B2 | 1/2010 | Moesli et al. |
| 7,794,432 | B2 | 9/2010 | Young et al. |
| 8,632,504 | B2 | 1/2014 | Young |
| 2001/0005781 | A1* | 6/2001 | Bergens ............... A61M 5/2033 604/208 |
| 2008/0262438 | A1* | 10/2008 | Bollenbach ......... A61M 5/2033 604/207 |
| 2011/0301548 | A1* | 12/2011 | Young ................. A61M 5/2033 604/200 |
| 2012/0209192 | A1 | 8/2012 | Alexandersson |
| 2013/0060196 | A1 | 3/2013 | O'Connor et al. |

FOREIGN PATENT DOCUMENTS

| | | |
|---|---|---|
| EP | 1459775 A1 | 9/2004 |
| EP | 2489381 A1 | 8/2012 |
| JP | 2012517845 A | 8/2012 |
| WO | 2005070481 A1 | 8/2005 |
| WO | 2010094916 A1 | 8/2010 |
| WO | 2011043714 A1 | 4/2011 |
| WO | 2012022810 A2 | 2/2012 |
| WO | 2012039276 A1 | 3/2012 |
| WO | 2012073035 A1 | 6/2012 |
| WO | 2012085585 A2 | 6/2012 |
| WO | 2013034958 A1 | 3/2013 |
| WO | 2013034985 A2 | 3/2013 |

OTHER PUBLICATIONS

International Preliminary Report on Patentability from corresponding International Application No. PCT/GB2014/052282 dated Feb. 11, 2016.
International Search Report and Written Opinion from corresponding International Application No. PCT/GB2014/052282 dated Jan. 22, 2015.
Search Report from corresponding GB Application No. GB1313782.3 dated Jan. 20, 2014.
Examination Report of the European Patent Office from corresponding EP Application Serial No. 14744928.4 dated Mar. 9, 2018.
English Translation of Notice of Reasons for Rejection from corresponding JP Application Serial No. 2016-530597 dated Jun. 5, 2018.
English Translation of First Office Action of the State Intellectual Property Office of the People's Republic of China from corresponding CN Application Serial No. 201480054227.2 dated Jul. 16, 2018.
Decision of Patent Grant of the Japanese Patent Office from corresponding JP Application Serial No. 2016-530597 dated Feb. 5, 2019.
Office Action from corresponding Japanese Application No. 2019-041249 dated Jun. 2, 2020.
First Office Action of the State Intellectual Property Office of the People's Republic of China from corresponding CN Application Serial No. 201910301065.2 dated Jan. 5, 2021.
Examination Report of the Indian Patent Office from corresponding IN Application Serial No. 201617003326 dated Mar. 30, 2021.

* cited by examiner

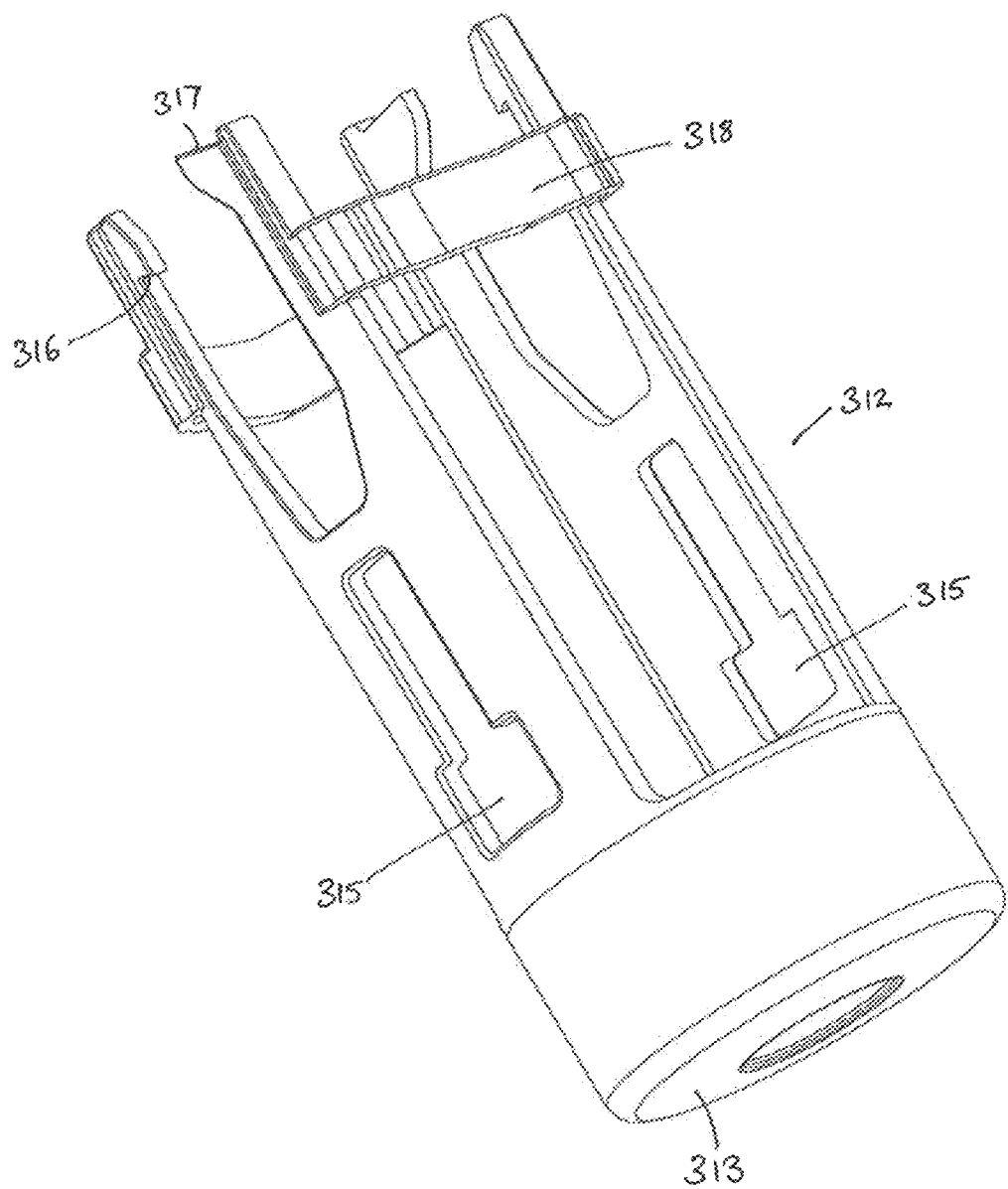

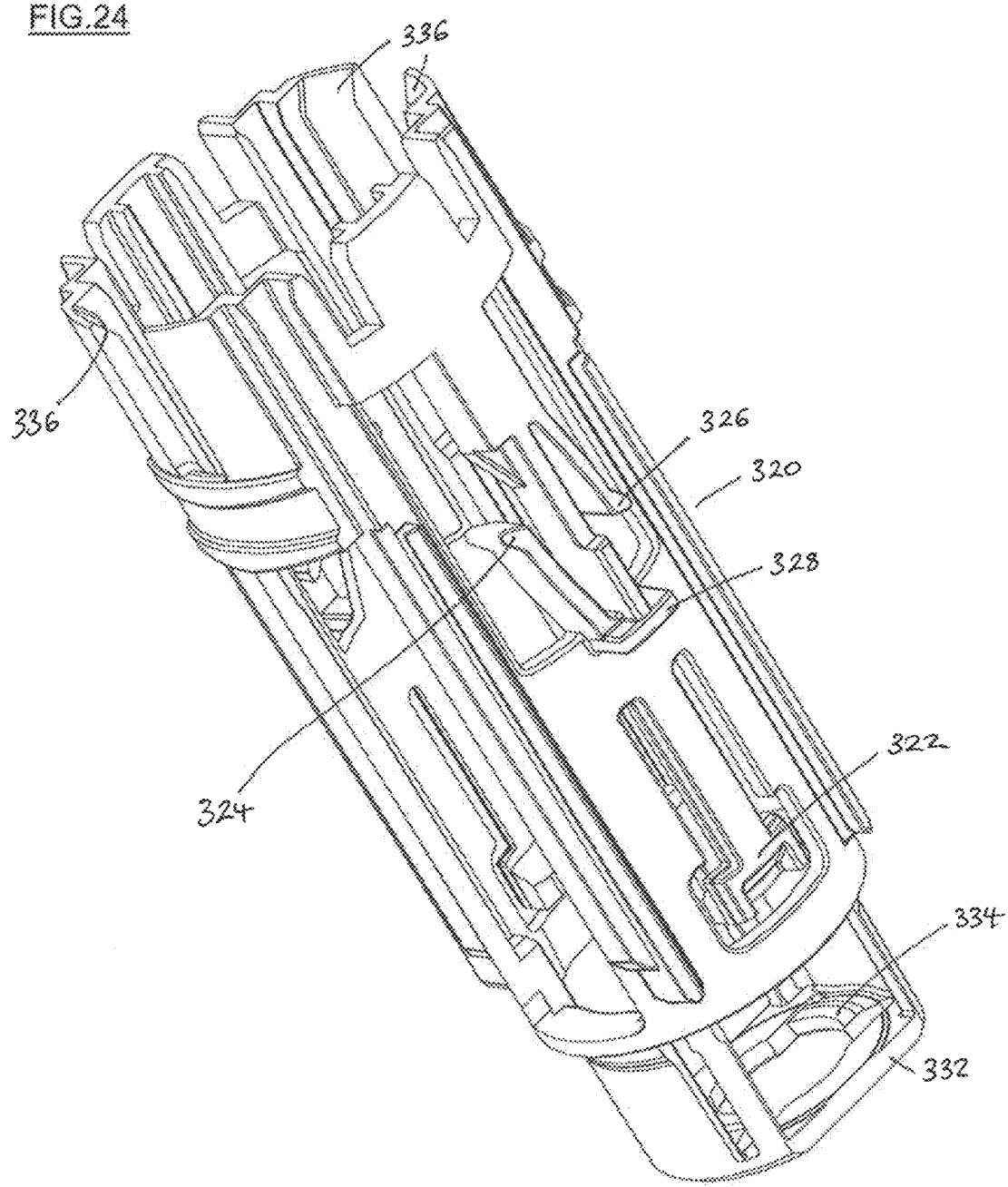

DRUG DELIVERY DEVICE

CROSS-REFERENCE TO RELATED APPLICATIONS

This application is a continuation of U.S. patent application Ser. No. 14/908,439, filed Jan. 28, 2016, titled DRUG DELIVERY DEVICE, which is a U.S. National Stage Application under 35 U.S.C. § 371 of International Application No. PCT/GB2014/052282, filed Jul. 25, 2014, titled DRUG DELIVERY DEVICE, which claims priority to United Kingdom Patent Application No. GB 1313782.3, filed Aug. 1, 2013. U.S. patent application Ser. No. 14/908,439 and International Application No. PCT/GB2014/052282 are each incorporated by reference herein in their entirety.

FIELD OF THE INVENTION

The present invention relates to devices for administering drugs to patients, and in particular to autoinjectors.

BACKGROUND TO THE INVENTION

An autoinjector is a drug delivery device that contains a medical, therapeutic, diagnostic, pharmaceutical or cosmetic compound (drug) before it is administered, and which is used to administer the compound through the skin of the patient via a hollow needle. Autoinjectors may be used by the patient themselves or by a different user, and may be used to administer drugs to animals.

Autoinjectors are typically used because they reduce the amount of training and effort needed by a user compared with that needed for a syringe, by automating either or both processes of inserting the needle into the patient and expelling the drug through the needle. They can also reduce the fear of injection by hiding the needle from the patient and protect the patient from needle stick injuries.

Autoinjectors typically include a housing containing a drug and a plunger that is driven by an automatic mechanism to move the plunger within the housing to eject the drug. The automatic mechanism may also move the needle relative to the housing to insert the needle into a subject. Motive power for the mechanisms may come from one or more springs or other power sources such as compressed gas.

Autoinjectors are used to deliver so-called crisis drugs such as epinephrine, where a patient may need to self-inject the drug while under the severe stress of anaphylactic shock. They are also used to deliver drugs for long-term conditions such as rheumatoid arthritis, where the patient may have limited dexterity.

In both cases it is beneficial for the autoinjector to have a simple and easy user interface in order to maximise the likelihood that the patient is able to operate the autoinjector correctly and receive the drug. It would also be desirable to provide an audible indication to the patient that drug delivery has been successfully completed.

It is also desirable for the autoinjector to be small, reliable and robust, simple to manufacture, secure during transport and before intended use, and suitable for drugs having high viscosity.

SUMMARY OF THE INVENTION

The invention is defined in the appended independent claims, to which reference should be made. Advantageous features are set out in the dependent claims.

In a first aspect, there is provided a drug delivery device comprising:
a drug container containing a drug;
a plunger within the drug container, movement of the plunger within the drug container being operative to deliver the drug from the drug container; and
a drive mechanism, the drive mechanism comprising: a stored energy source, the stored energy source configured to release energy by expanding from a compressed state, a first drive element coupled to the stored energy source, and a second drive element coupled to the first drive element and positioned between the first drive element and the plunger, wherein in a first position of the drive mechanism the first drive element is constrained from moving in an axial direction relative to the second drive element but in a second position of the drive mechanism the first drive element is free to move in the axial direction relative to the second drive element such that a first surface of the first drive element is driven against a first surface of the second drive element by the stored energy source to produce an audible signal indicative of the completion of drug delivery from the drug container.

Previous mechanisms used to provide an audible indication of completion of drug delivery in drug delivery devices have suffered from the problem that the audible indication has not been loud enough. They have typically relied on a portion of the drive element used to drive the drug out of the device striking a stationary part of the device housing as it moves past that stationary part. The solution of the present invention is to use a stored energy source to drive two parts of a multi-part drive mechanism against each other when the drive mechanism reaches a predetermined position within the device. This allows a much greater noise to be generated as the parts can be made rigid and may be driven against each other at high speed.

Advantageously the expansion of the stored energy source moves the drive mechanism from the first position to the second position.

In order to constrain the first drive element from moving in the axial direction relative to the second drive element in the first position, a further component within the drive mechanism, which interacts with an external component of the device, may be used. Alternatively, an external component of the housing through which the drive mechanism moves may be used to interact with the first or second drive element to constrain relative axial movement between the first and second drive element.

In some embodiments, the drive mechanism may comprise a third drive element, the third drive element constraining relative movement between the first drive element and the second drive element when the drive mechanism is in the first position, wherein the third drive element is configured to engage the drug container or a portion of a housing of the drug delivery device as the drive mechanism moves to the second position.

The third drive element may be configured to engage the drug container or a portion of the housing of the drug delivery device at a release position between the first position and the second position of the drive mechanism, and, as the drive mechanism moves from the release position to the second position, the third drive element may be held stationary relative to the drug container or housing to release the first or second drive member from the third drive member. The third drive element may be positioned between the first and second drive elements.

It is important that the first surface of the first drive element is driven against the first surface of the second drive element reliably and at the correct time, which is when the drug has been fully (or almost fully) expelled from the drug container by the drive mechanism. There are inevitably some small variations in the dimensions of the component parts of the device from one device to the next, no matter what manufacturing process is used. An advantage of configuring the third element to engage the drug container directly is that it means that relatively few separate components are involved in determining when the first drive element is driven against the first surface of the second drive element, so the requirement for very fine dimensional tolerances for each component is reduced, and the timing of the audible indication can more closely match the end of drug delivery. In the first position of the drive mechanism, the first drive element and the second drive element may be constrained from relative rotation. In the second position of the drive mechanism the first drive element and the second drive element may be free to rotate relative to one another and, following or during relative rotation, may move in an axial direction relative to one another.

The first drive element may comprise a first bearing surface, and the second drive element may comprise a second bearing surface engaging the first bearing surface in the first position of the drive mechanism, wherein rotation of the first drive element relative to the second drive element moves the first bearing surface off the second bearing surface, allowing the first surface of the first drive element to strike the first surface of the second drive element, wherein in the first position of the drive mechanism, the third drive element constrains relative rotation between the first drive element and the second drive element, and in the second position, the third drive element is moved axially relative to the first and second drive elements to a position in which the third drive element does not constrain relative rotation between the first drive element and the second drive element.

The second drive element may comprise a first axially extending protrusion or slot that in the first position engages the third drive element to prevent relative rotation between the second drive element and the third drive element, and the first drive element may comprise an axially extending slot or protrusion that in the first position engages with the third drive element to prevent relative rotation between the third drive element and the first drive element.

The third drive element may extend around at least a portion of the second drive element and the first drive element may extend around at least a portion of the third drive element. The first and third drive elements may be generally tubular.

Alternatively, or in addition, the drug delivery device may comprise a housing component coupled to or integral with the drug container, the housing component constraining the first drive element from moving relative to the second drive element in the first position of the drive mechanism. The drug delivery device may further comprise an external housing, wherein the drug container is configured to move through the external housing during operation of the device, and wherein the housing component moves through the external housing with the drug container. The drug delivery device may comprise a hypodermic needle and the housing component may be part of a needle insertion mechanism that moves the drug container through the housing to insert the needle into an injection site.

The drug delivery device may be an autoinjector.

In a second aspect, there is provided a drug delivery device comprising:
a housing;
a drug container, and
an powerpack assembly coupled to the drug container, the powerpack assembly comprising:
a stored energy source, the stored energy source configured to release energy by expanding from a compressed state;
an insertion member engaging the stored energy source and positioned between the stored energy source and the drug container; and
a retaining means, in a first position the retaining means engaging the stored energy source and the insertion member to retain the stored energy source in a first compressed state;
wherein the retaining means and housing are configured such that the retaining means is moved by the housing to a second position on engagement of the powerpack assembly with the housing, the retaining means being disengaged from the stored energy source or the insertion member in the second position;
the drug container and housing being configured such that the stored energy source is retained in a second compressed state by the drug container when the retaining means is moved to the second position, and
a triggering mechanism configured to release the stored energy source from the second compressed state when the autoinjector is to be used.

The housing may comprise a first cam surface configured to engage a second cam surface on the retaining means. The retaining means and housing may be configured such that the retaining means is rotated by the housing to the second position on engagement of the powerpack assembly with the housing.

The stored energy source may be a compression spring or a gas spring, for example. The drug delivery device may further comprise a drive mechanism configured to drive a plunger through the drug container, the drive mechanism comprising a second stored energy source, and a release mechanism configured to control a sequence of release of the first stored energy source and the second stored energy source, wherein the retaining means forms a part of the release mechanism.

The drive mechanism may be configured to drive the drug container through the housing in a longitudinal direction, and wherein the retaining means comprises a longitudinally extending retaining limb that retains a drive element of the drive mechanism to the insertion member to prevent a release of the second stored energy source. The retaining limb may be configured to release the drive element from the insertion member substantially at an end of travel of the drug container through the housing. The retaining means and housing may be configured such that the retaining means is rotated about a longitudinal axis by the housing to the second position. The retaining means may be held within the housing and is inaccessible to a user during use. As used herein, the axial direction, the longitudinal direction and the insertion direction are used to mean the same direction.

Prior to use of the device, the first stored energy source may be positioned at least partially within the second stored energy source. The insertion element may comprise a first portion comprising a bearing surface engaging the first stored energy source, and a second portion extending from the first portion, the second portion defining a recess in which the second stored energy source is received.

The insertion element may be assembled from two components to simplify manufacture and assembly of the device.

The drive member may comprise a mechanism for providing an audible indication in accordance with the first aspect of the invention.

The drug container may be retained by one or more latches on the housing or on an internal component coupled to the housing, to retain the stored energy source in the second compressed state.

The triggering mechanism may comprise a movable skin sensor element, configured such that when the skin sensor element is pressed onto an injection site, the skin sensor element moves to release the drive means from the second deformed condition.

The drug delivery device may be an autoinjector.

In a third aspect of the invention there is provided a method for assembling a drug delivery device according to the second aspect of the invention, comprising the steps of:

placing or forming a stored energy source in a powerpack assembly having a powerpack housing;

retaining the stored energy source in the powerpack assembly in a first compressed condition using a retaining means coupled to the drive member and the powerpack housing in a first position;

coupling the powerpack assembly to a drug container assembly, the drug container assembly containing a drug to be dispensed by the autoinjector;

coupling the powerpack assembly and drug container assembly to an outer housing; and moving the retaining means to a second position to release the stored energy source to second compressed condition, wherein the drug container assembly and outer housing retain the stored energy source in the second compressed condition and wherein in the second compressed condition the stored energy source stores sufficient potential energy for needle insertion and/or drug ejection when the autoinjector is to be used.

The step of moving the retaining means may be performed as a consequence of the step of coupling to the outer housing.

The step of moving the retaining means may comprise rotation of the retaining means relative to the powerpack housing.

In a fourth aspect, there is provided a drug delivery device comprising:

a device housing;

a drug container within the housing and containing a drug, and a plunger positioned within the drug container, the drug container having an outlet for dispensing the drug; and a powerpack assembly, the powerpack assembly comprising an insertion member fixed to or abutting the drug container, a first stored energy source positioned between the insertion member and the device housing, and a second stored energy source positioned between the insertion member and a drive member, wherein, in use, the drive member is configured to engage the plunger, wherein, in an initial position, the first stored energy source is located at least partially within the second stored energy source.

The insertion member may be driven by the first stored energy source to move the drug container through the housing and the drive member may be driven by the second stored energy source to move the plunger through the drug container.

The second stored energy source may be held within the insertion member before operation of the device.

The insertion member may comprise a first portion comprising a first bearing surface engaging the first stored energy source, and a second portion extending from the first portion, the second portion defining a recess in which the second stored energy source is received. The first or second portion of the insertion member may comprise a second bearing surface engaging the drive member.

The drug delivery device may further comprise a retaining means, the retaining means coupled to the device housing, and extending within the first stored energy source and engaging the drive member or the insertion member to prevent the drive member from disengaging from the second bearing surface. The device may be configured such that movement of the insertion member through the housing to an insertion position releases the drive member from the retaining means.

The first stored energy source may be configured to expand to release energy to drive the insertion member within the device housing and the first stored energy source may be initially prevented from expanding by the engagement of a portion of the device housing with the drug container.

The drug delivery device may be an autoinjector.

In a fifth aspect of the invention, there is provided a drug delivery device, comprising:

a drug container;

an internal housing;

an insertion mechanism coupled to the drug container and configured to move the drug container through the internal housing in an insertion direction;

a skin sensor element, configured to contact an injection site in use; and a skin sensor biasing element biasing the skin sensor in the insertion direction;

wherein the skin sensor element is movable in a direction opposite to the insertion direction from an initial position to a retracted position to trigger the insertion mechanism;

wherein the internal housing includes a first latching element to restrain the skin sensor element from moving from the initial position in the insertion direction, wherein the first latching element comprises a latching surface configured to engage the skin sensor element and a first camming surface; and wherein either the drug container or the insertion mechanism includes a second camming surface, wherein the second camming surface is configured to engage the first camming surface to move the first latching element as the drug container is moved through the internal housing in the axial direction, thereby allowing the skin sensor element to move in the insertion direction past the initial position to an extended position. In the extended position the skin sensor element covers the needle.

The first latching element may comprise a resilient cantilever arm, wherein the latching surface and the first camming surface are formed at a free end of the cantilever arm. The cantilever arm may be held in tension by the skin sensor element and skin sensor biasing element when the skin sensor is in the initial position.

The internal housing may define a central bore through which the drug container moves, and the first and second camming surfaces may be configured to move the latching element in a direction parallel to a perimeter of the bore. The first camming surface may be positioned inwardly of the latching surface. The first camming surface advantageously extends non-parallel with the latching surface. Inwardly in this context means further from an exterior surface of the device.

The skin sensor element may comprise at least a first aperture that aligns with a drug container latch on the internal housing when the skin sensor element is in the retracted position.

The skin sensor may be configured so as not to occlude a window in the internal housing for viewing the drug container when in the initial or retracted position.

The drug delivery device may further comprise a second latching element formed on the internal housing, the second latching element being configured to prevent the skin sensor moving to the retracted position after it has been released from the first latching element. The second latching element may engage a second aperture or a protrusion on the skin sensor element.

In the retracted position the skin sensor element may abut the internal housing to prevent further movement of the skin sensor element relative to the internal housing in a direction opposite to the insertion direction.

The drug delivery device may be an autoinjector.

In a sixth aspect of the invention there is provided a needle assembly comprising:

a hypodermic needle;

a needle hub to which the needle is fixed at a first end;

a needle shield coupled to the needle hub and covering a second end of the needle; wherein the needle shield comprises a rigid body, the rigid body providing a sterile barrier around at least a portion of the needle; and a compliant element within the rigid body, the compliant member providing a liquid tight seal around a second end of the needle, wherein the rigid body is configured to provide an interference fit with the needle hub and thereby provides a seal around the needle hub.

The rigid body may be formed from a moulded plastics material, such as high-density polyethylene or polypropylene.

The needle assembly may comprise at least one circumferential rib on an interior surface of the rigid body or on an external surface of the needle hub. Preferably, the needle assembly comprises at least two circumferential ribs on the interior surface of the rigid body. The radius of curvature of each rib at the contact point, prior to fitting of the rigid body to the needle hub is preferably less than 0.6 mm. The contact point of each rib is the point on the surface of the rib that is configured to first contact the needle hub when the rigid body is fitted to the needle hub.

The needle hub may be formed from a moulded plastics material, such as cyclic olefin polymer.

The needle hub may have a surface finish having a maximum distance between peak and trough of 2 µm or less. Preferably, a surface finish of the needle hub is 0.2 Ra or less. The needle hub may have a circular cylindrical outer surface to which the rigid body is coupled. An interior surface of the rigid body preferably has a surface finish of 0.2 Ra or less. An interior surface of the rigid body may have a surface finish having a maximum distance between peak and trough of 2 µm or less.

The rigid body may comprise an external surface having at least one protrusion or recess. At least a portion of the rigid body may be transparent.

The compliant element may be fully enclosed, or may be only partially enclosed, by the rigid body and needle hub. The compliant element may be retained in the rigid body by at least one protrusion on the rigid body.

The needle assembly may further comprise at least one vent in the compliant element or the rigid body for allowing air to escape from the rigid body during insertion of the compliant element into the rigid body. Alternatively, the rigid body may be moulded over the compliant element, or the compliant element may be moulded inside the rigid body.

In a seventh aspect of the invention, there is provided an autoinjector or syringe comprising a needle assembly in accordance with the sixth aspect.

In an eighth aspect of the invention, there is provided a method of manufacturing a needle assembly comprising:

fixing a first end of a needle to a needle hub; and coupling a needle shield to the needle hub, the needle shield covering a second end of the needle; wherein the needle shield comprises a rigid body and a complaint element, wherein the rigid body is configured to provide an interference fit with the needle hub and thereby provide a seal around the needle hub, the rigid body providing a sterile barrier around at least a portion of the needle, the step of coupling including inserting a second end of the needle into the compliant element such that the compliant element provides a liquid tight seal around the second end of the needle.

In a ninth aspect of the invention, there is provided a drug delivery device comprising:

a drug container assembly comprising a drug container containing a drug, a hypodermic needle coupled to the drug container and through which the drug can be dispensed and a plunger within the drug container;

an internal housing, the drug container positioned within the internal housing and movable through the internal housing;

a powerpack assembly comprising at least one stored energy source, the powerpack assembly coupled to the drug container;

a lower housing fixed to the internal housing;

an upper housing fixed to the lower housing and enclosing the powerpack assembly;

a skin sensor element extending between the lower housing and the internal housing and movable relative to the internal housing and the lower housing; and a cap covering the skin sensor element and coupled to the lower housing.

The upper housing may be fixed to the lower housing using one or more mechanical fixings.

The device may be configured such that movement of the skin sensor element relative to the internal housing from an initial position to a retracted position releases the stored energy source within the powerpack assembly.

The internal housing may comprise retaining latches, which, when the skin sensor element is in the initial position, are engaged with the drug container to retain the drug container in an initial position of the drug container to retain the stored energy source, and wherein movement of the skin sensor element to the retracted position allows the retaining latches to disengage from the drug container, thereby releasing the stored energy source. The internal housing may comprise first latching elements that restrain the skin sensor element from movement out of the initial position. The first latching elements may be resilient arms that engage the skin sensor element at a free end.

The lower housing or internal housing may comprise second latching elements that lock the skin sensor element in an extended position after the skin sensor has moved to the extended position.

The powerpack assembly may comprise first and second stored energy sources, wherein the first stored energy source provides energy to move the drug container from an initial position of the drug container to an insertion position of the drug container, and wherein the second stored energy source provides energy to move the plunger within the drug container to dispense the drug. The powerpack assembly may be fixed to the drug container. The stored energy sources may be compression springs.

The powerpack assembly may comprise a retaining means in accordance with the second aspect of the invention. The powerpack may comprise a drive mechanism in accordance with the first aspect of the invention.

The internal housing may comprise a stopping surface configured to engage the drug container as the drug container moves to an insertion position. The stopping surface may comprise one or more resilient cantilever beams that are deformed by the drug container as the drug container moves to an insertion position.

The cap may directly or indirectly engage the skin sensor element, to prevent the skin sensor element from moving to a retracted position from an initial position.

The upper housing or lower housing may comprise an aperture to allow for viewing of the drug. The internal housing or the lower housing may be transparent and may be configured to engage the aperture in upper housing.

The upper housing may comprise two major surfaces each including an aperture to allow for viewing of the drug, and two minor surfaces. The first and second latching elements may be positioned adjacent a minor surface of the upper housing.

The drug delivery device may be an autoinjector.

In a tenth aspect of the invention, there is provided a method of assembling a drug delivery device according to the ninth aspect, comprising the steps of:
providing the powerpack assembly;
providing the drug container assembly;
providing a front end assembly comprising the internal housing, the lower housing and the skin sensor and the cap;
providing the upper housing;
coupling the powerpack assembly to the drug container assembly;
coupling the drug container assembly to the front end assembly; and
coupling the powerpack assembly, drug container assembly and front end assembly to the upper housing.

The step of coupling the powerpack assembly to the drug container assembly may be performed before or after the step of coupling the drug container assembly to the front end assembly. Similarly, the cap may be coupled to the other elements of the front end assembly at any point in the method.

In an eleventh aspect of the invention, there is provided a drug delivery device comprising:
a housing;
a drug container within the housing,
a powerpack assembly configured to move the drug container through the housing in an axial direction from an initial position to an insertion position,
wherein the housing includes a stopping surface configured to engage the drug container when the drug container reaches the insertion position, wherein the stopping surface is provided on a least one resilient beam on the housing, the resilient beam being deflectable in the axial direction.

The stopping surface may be provided on a pair of cantilever beams. The device may comprise an outer housing and an internal housing, and the stopping surface is provided on the internal housing.

The drug container may comprise a hypodermic needle. The drug delivery device may be an autoinjector.

In a twelfth aspect of the invention, there is provided a drug delivery device comprising:

a housing;
a drug container within the housing and containing a drug to be dispensed, the drug container having a first end defining a first opening;
a plunger, positioned within the drug container, in contact with the drug;
a first sealing element providing a first closure seal across the first opening of the drug container;
a pusher initially located on an opposite side of the first closure seal to the plunger, wherein the pusher is operable to break the first closure seal and move the plunger within the drug container to dispense the drug; and
an insertion mechanism configured to move the drug container through the housing,
wherein, prior to use, the pusher and the insertion mechanism are held out of contact with the first sealing element.

The sealing element may be laminated foil and may be welded or glued to the drug container. The term "closure seal" as used herein in the claims and description means a seal that prevents deterioration or contamination of a drug in a container against foreseeable external factors in storage. A closure seal maintains the safety, identity, strength, quality, sterility and/or purity of a drug in a container in compliance with official, regulatory or established requirements.

The drug container may comprise a second opening through which the drug is dispensed and at least one side wall extending between the first opening and the second opening, wherein the drive mechanism is engaged to the at least one sidewall.

The drug delivery device may be an autoinjector.

In a thirteenth aspect there is provided a drug delivery device comprising:
a housing;
a drug container within the housing and containing a drug to be dispensed, the drug container having a first end defining a first opening;
a plunger, positioned within the drug container, in contact with the drug;
a first sealing element providing a first closure seal across the first opening of the drug container;
a pusher initially located on an opposite side of the first closure seal to the plunger, wherein the pusher is operable to break the first closure seal and move the plunger within the drug container to dispense the drug; and
an insertion mechanism configured to move the drug container through the housing prior to operation of the pusher to break the first closure seal,
wherein, no elements of the insertion mechanism and housing contact the first sealing element as the drug container is moved through the housing.

The drug delivery device may be an autoinjector.

Features described in relation to one aspect of the invention may equally be applied to any other aspect of the invention.

BRIEF DESCRIPTION OF THE DRAWINGS

Embodiments of the invention will now be described, by way of example only, with reference to the accompanying drawings, in which:

FIG. 23 is a perspective view of a skin sensor element of the second embodiment;

FIG. 24 is a perspective view of a chassis of the second embodiment;

DETAILED DESCRIPTION

Figure 1:
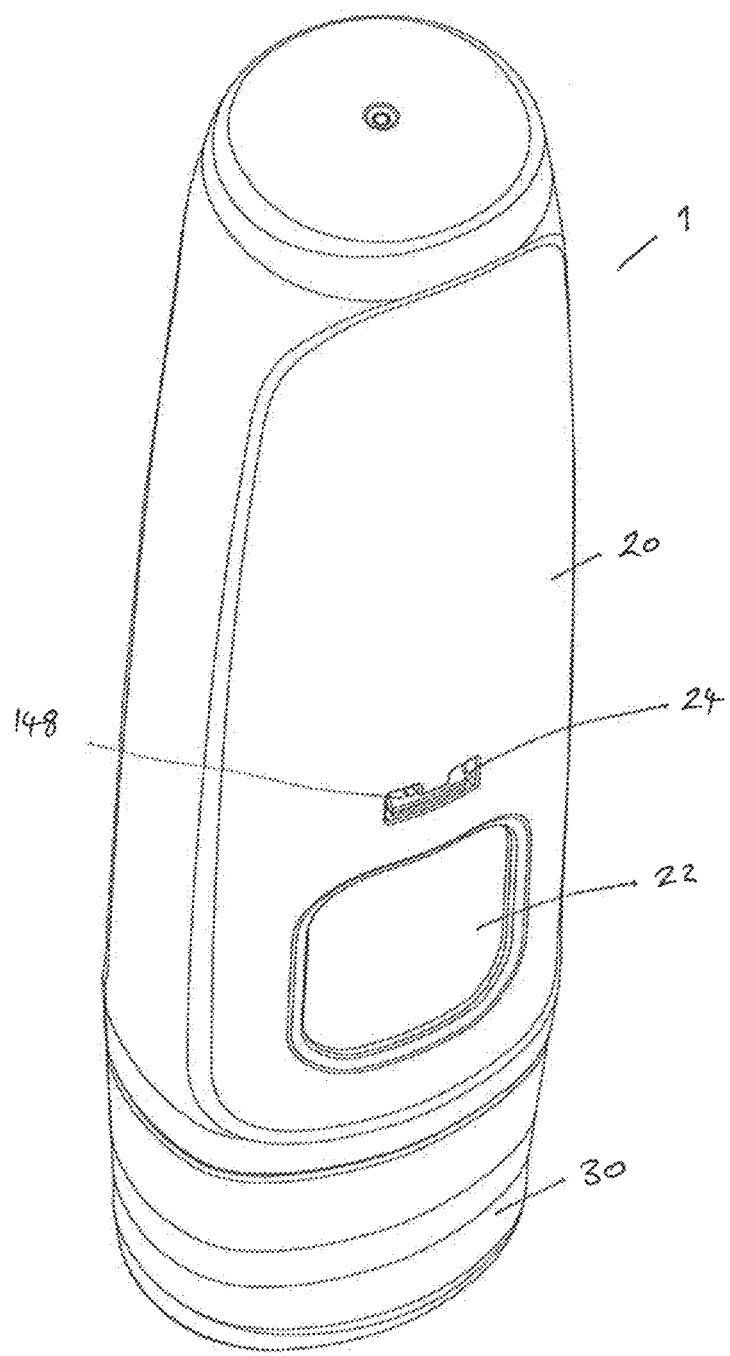
FIG. 1 is a perspective view of an autoinjector in accordance with a first embodiment of the invention, prior to use.

FIG. 1 is a perspective view of an autoinjector 1 in accordance with a first embodiment of the invention, before use. The autoinjector comprises an outer housing 20, having a viewing window 22 through which a drug within the autoinjector can be inspected. A cap 30 is provided to cover the end of the device through which the needle passes during operation and to prevent inadvertent activation of the device. The autoinjector is compact, being approximately 10 cm long and fits easily in a user's hand.

Figure 2:
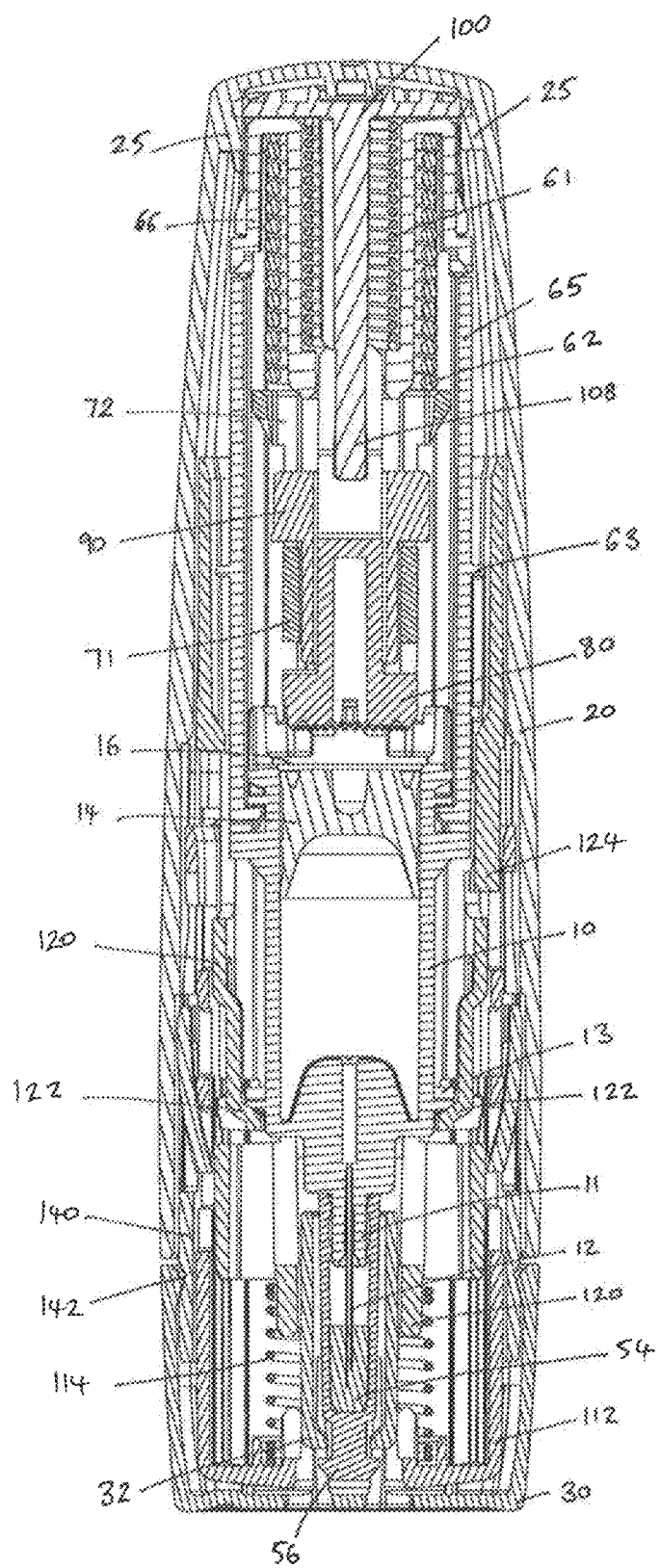
FIG. 2 is a first cross-section through the autoinjector of FIG. 1.
Figure 3:
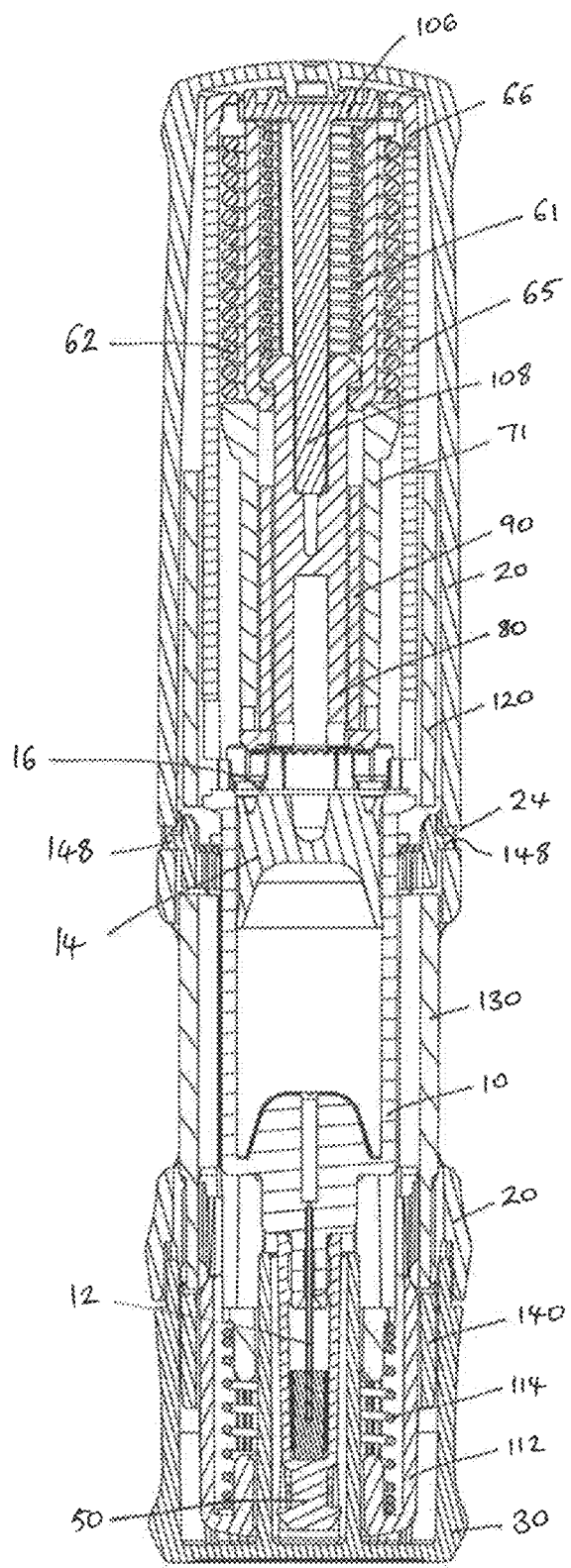
FIG. 3 is a second cross-section through the autoinjector of FIG. 1.

FIG. 2 is a cross-sectional view through the autoinjector 1 of FIG. 1. FIG. 3 is a second cross-sectional view through the autoinjector of FIG. 1, at 90 degrees to the cross-section of FIG. 2.

Figure 14:
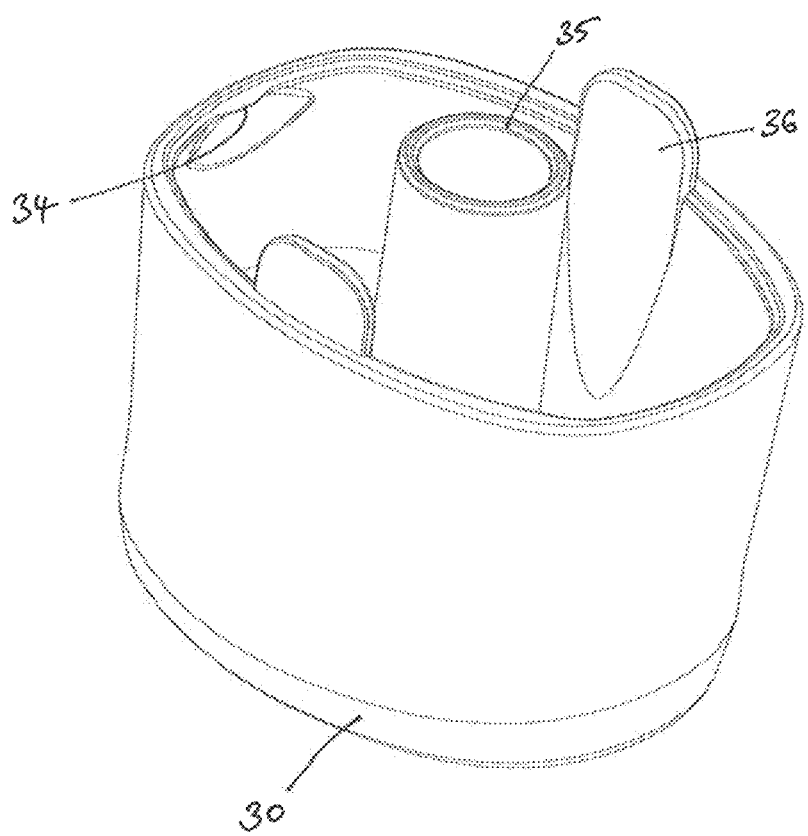
FIG. 14 is a perspective view of the cap.

The autoinjector 1 shown in FIGS. 1, 2 and 3 comprises a drug container assembly (shown in FIGS. 4a and 4b), a powerpack assembly (shown partially in FIGS. 6a, 6b and 7) including an end of delivery noise generating mechanism (shown in FIGS. 8 and 9), an internal housing (shown in FIG. 11), herein referred to as the chassis, a skin sensor assembly comprising a skin sensor element (shown in FIG. 10) and a skin sensor spring, a lower housing (shown in FIG. 12), an outer housing and a cap (shown in FIG. 14).

The drug container assembly 10 is held within the chassis 120 and in operation moves through the chassis. The drug container assembly 10 is retained in an initial position by latches 122 on the chassis, which engage protrusions 13 on the drug container and which are prevented from releasing the drug container by the skin sensor assembly. The skin sensor assembly comprises a skin sensor element 112 and a skin sensor spring 114. The skin sensor element is held by latching elements 124 on the chassis 120 and urged away from the drug container assembly 10 by the skin sensor spring 114, which is held between the chassis 120 and the skin sensor element 112. The lower housing 140 engages the chassis 120 by clipping to a window portion 130 of the chassis. Lugs 148 on the lower housing engage recesses 24 formed in the outer housing. The cap 30 engages recesses 142 on the lower housing and covers the skin sensor element 112.

Figure 4A:
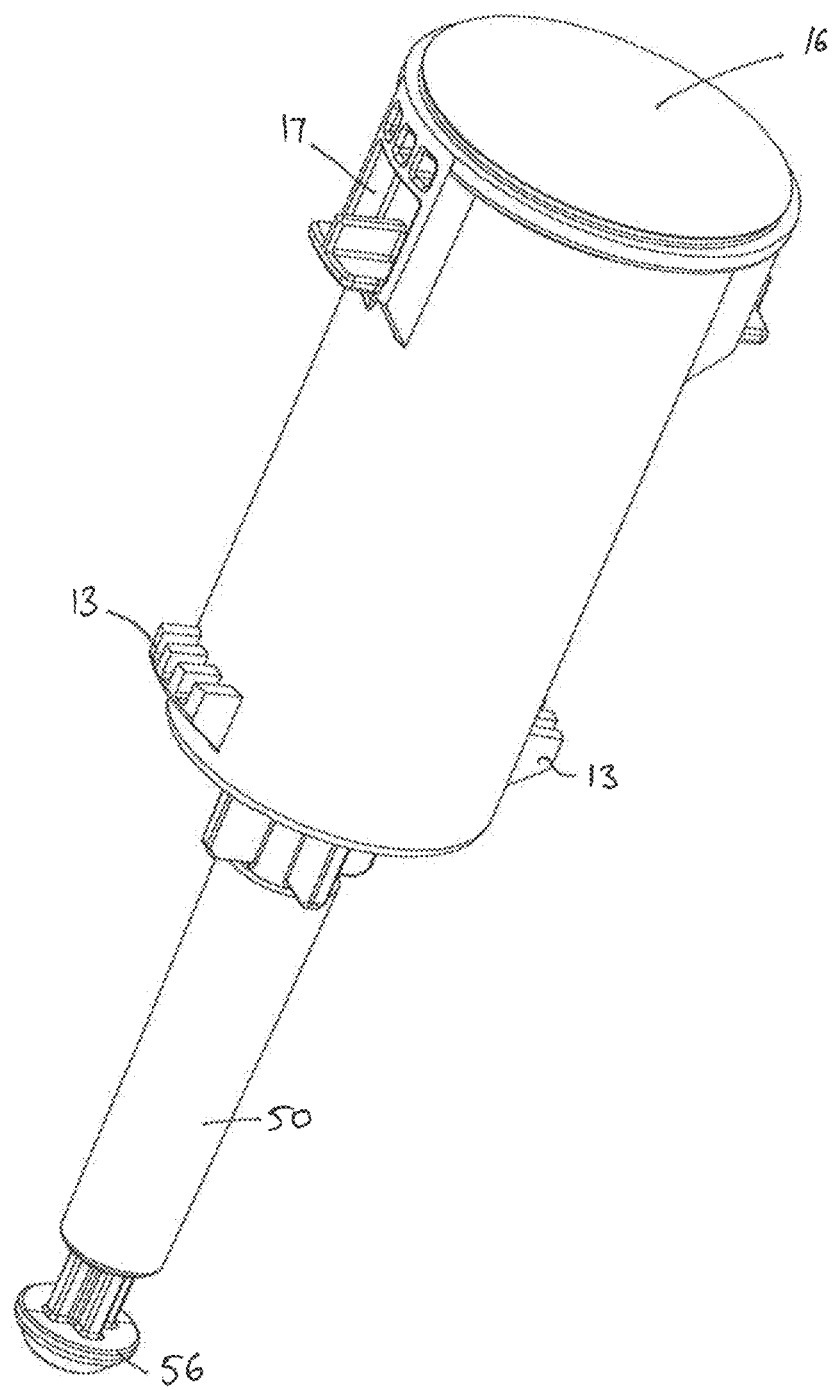
FIG. 4a is a perspective view of the drug container assembly.
Figure 4B:
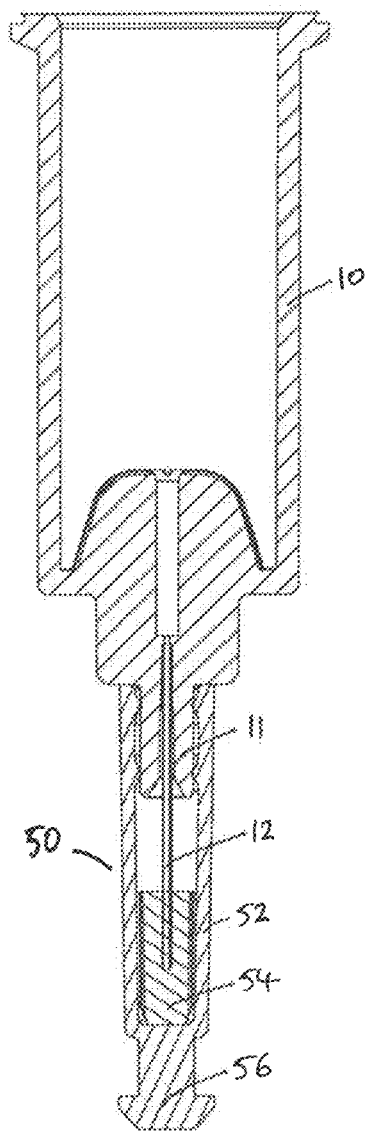
FIG. 4b is a cross-section view of the drug container assembly.

The drug container assembly is shown alone in FIG. 4a. FIG. 4b is a cross-section view of FIG. 4a. The drug container assembly comprises a drug container 10 containing a drug to be delivered to a patient by injection, with a hypodermic needle 12 fixed to a front end. The drug container is formed from cyclic olefin, which has excellent drug contact properties. The use of a plastic drug container has several advantages over glass. A plastic container can be moulded with features that form part of the automatic injection and drug delivery mechanism, as described in relation to this embodiment below, and can be formed with much higher accuracy than glass, A plastic container can also withstand higher impact forces and pressures allowing for the use of more powerful springs in the autoinjector mechanism and for a shorter, fatter drug container.

A plunger 14 is provided within the drug container. Movement of the plunger 14 within the drug container 10 urges the drug out through the needle 12. The plunger is designed to provide low friction with the walls of the drug container and to minimise any station between the plunger and the drug container. The plunger is a cup seal type plunger, configured such that a component of the fluid pressure exerted by the drug on the plunger as the plunger is moved through the drug containers is directed towards a sealing interface between the plunger and an internal surface of the drug container. A plunger of this type is described in GB2467904. A peripheral portion of the plunger 14 in contact with a wall of the drug container comprises a substantially non-elastomeric material. The internal surface of the front end of the drug container 10 is shaped to match the shape of the front end of the plunger 14 to maximise the amount of drug that is pushed out of the drug container during use.

A sealing foil 16 is provided at a back end of the drug container 10 to ensure the drug is retained and maintained in a sterile and pristine condition. The sealing foil 16 may be laminated foil including a layer of aluminium and may be welded or glued to a back end of the drug container 10.

In this embodiment, the hypodermic needle 12 is glued into a needle hub portion 11 of the drug container 10. However, the drug container may be moulded around the needle. The needle is covered by a needle shield 50 that keeps the needle 12 sterile. As shown in FIG. 4b, the needle shield 50 comprises a rigid outer housing 52 that forms a seal with the needle hub portion 11. A compliant element in the form of an elastomeric plug 54 is provided within the needle shield into which the front end of the needle 12 is inserted. The elastomeric plug seals the needle and ensures that no drug can escape from the needle prior to removal of the needle shield. The rigid outer housing 52 of the needle shield may be transparent to allow for inspection of the needle during assembly of the autoinjector. The front end of the rigid outer housing 52 comprises a bulb 56 configured to engage hooks 32 in the cap 30, as shown in FIG. 2a. This ensures that when the cap 30 is removed the needle shield is removed with it.

Figure 5:
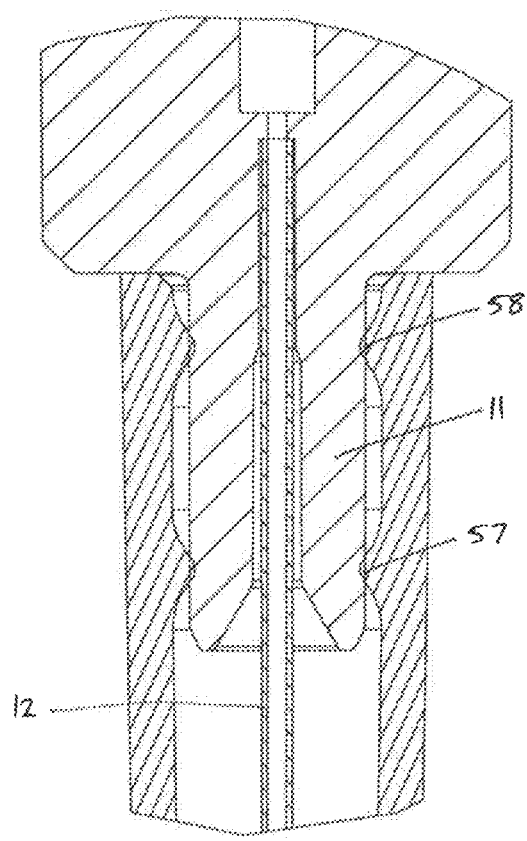
FIG. 5 is a cross-section showing the needle shield and the needle hub of the drug container.

The sealing of the needle shield to the needle hub 11 is shown in detail in FIG. 5, which is close-up view of a portion of FIG. 4b. The needle hub 11 is cylindrical where it surrounded by the needle shield. The rigid body 52 of the needle shield has a pair of ribs 57, 58 that extend around the inner surface of the needle shield. The ribs have an interference fit with the needle hub 11 to provide a seal that maintains the needle sterile. In this example, the hub has a diameter of 2.4 mm and a surface finish quality where the maximum distance between peak and trough is no more than 2 µm. The needle hub may be formed from a moulded plastics material, such as cyclic olefin polymer. The surface finish of the needle hub is specified to 0.2 Ra. The needle hub may have a circular cylindrical outer surface to which the rigid body is coupled. An interior surface of the rigid body is specified to have a surface finish of 0.2 Ra or less. An interior surface of the rigid body may have a surface finish having a maximum distance between peak and trough of 2 µm or less. The ribs have a nominal sealing diameter of 2.2 mm. There is therefore a nominal diametrical interference between the needle hub 11 and the needle shield 50 of 0.2 mm.

The rigid body of the needle shield is formed from polyethylene and has the same surface finish as the needle hub. The ribs 57, 58 are spaced from one another by 3 mm. In order to provide the greatest contact pressure between the ribs and the needle hub, combined with the lowest force, and so the tightest seal with the lowest removal force, the contact area between the ribs and the needle hub should be a small as possible. However, the contact area is limited by the manufacturing process for the needle shield and the materials used. In this example, the radius of curvature of each rib at the contact point, prior to fitting of the rigid body to the needle hub is preferably less than 0.6 mm. The contact point of each rib is the point on the surface of the rib that is configured to first contact the needle hub when the rigid body is fitted to the needle hub. However, the final contact radius may be larger than this, particularly if the plastic is deformed by the interference.

The autoinjector shown in FIGS. 1 to 3 also comprises an automatic mechanism for inserting the needle into an injection site and for ejecting the drug through the needle into the injection site. The automatic mechanism is referred to herein as the powerpack assembly. The powerpack assembly comprises stored energy sources, in the form of compressed springs 61, 62. When the first spring 61, referred to as the insertion spring, is released it moves the drug container 10 through the housing of the autoinjector to insert the needle 12 into an injection site. The second spring 62, referred to as the delivery spring, is then released to move the plunger 14 through the drug container 10 to inject the drug. The springs 61, 62 and the mechanism for controlling a sequence of release of the springs within the powerpack assembly are positioned rearward of the drug container.

The powerpack comprises a powerpack housing 64 that is coupled to the drug container 10. The powerpack housing of this embodiment comprises two parts, a lower powerpack housing 65 and an upper powerpack housing 66. The powerpack housing is in two parts to simplify the assembly of the autoinjector, but, in use, the two parts are fixed to each other and act as a single component. The lower powerpack housing 65 is clipped to the drug container 10. The lower powerpack housing 65 engages recesses 17 on the drug container. The insertion spring 61, shown in FIGS. 2 and 3 in a compressed condition prior to use of the autoinjector, is positioned between the upper powerpack housing 66 and a retaining means 100. The retaining means 100 is coupled to the upper powerpack housing 66 to retain the insertion spring 61 in a first compressed condition, as is explained with reference to FIG. 7.

The delivery spring 62 is positioned between the upper powerpack housing 66 and a multiple component drive member 70. When released, the delivery spring 62 drives the drive member 70 forward relative to the powerpack housing 64 and so drives the plunger 14 through the drug container 10 to eject the drug, as is described in detail below.

Figure 6A:
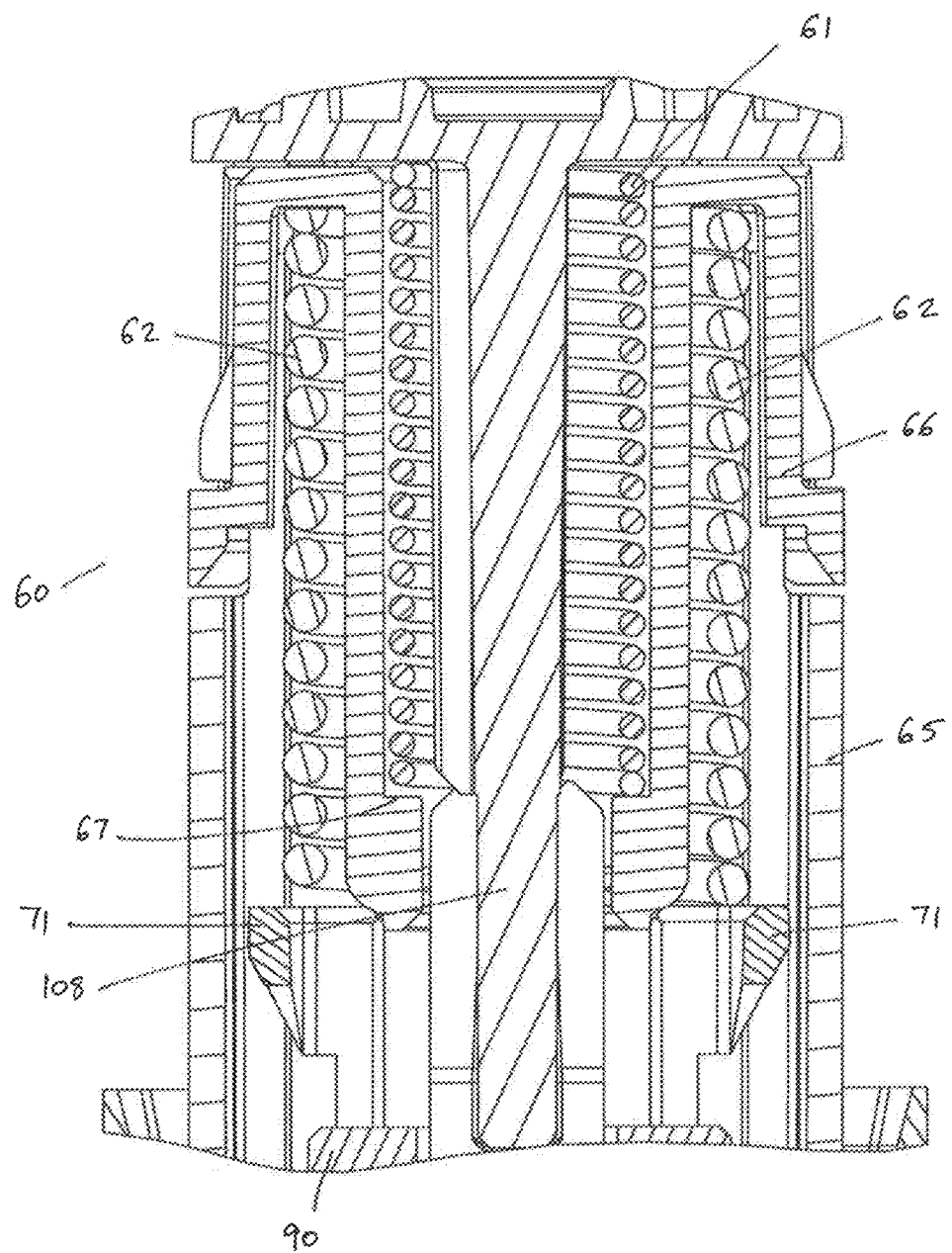
FIG. 6a is a first partial cross-section of the powerpack housing.
Figure 6B:
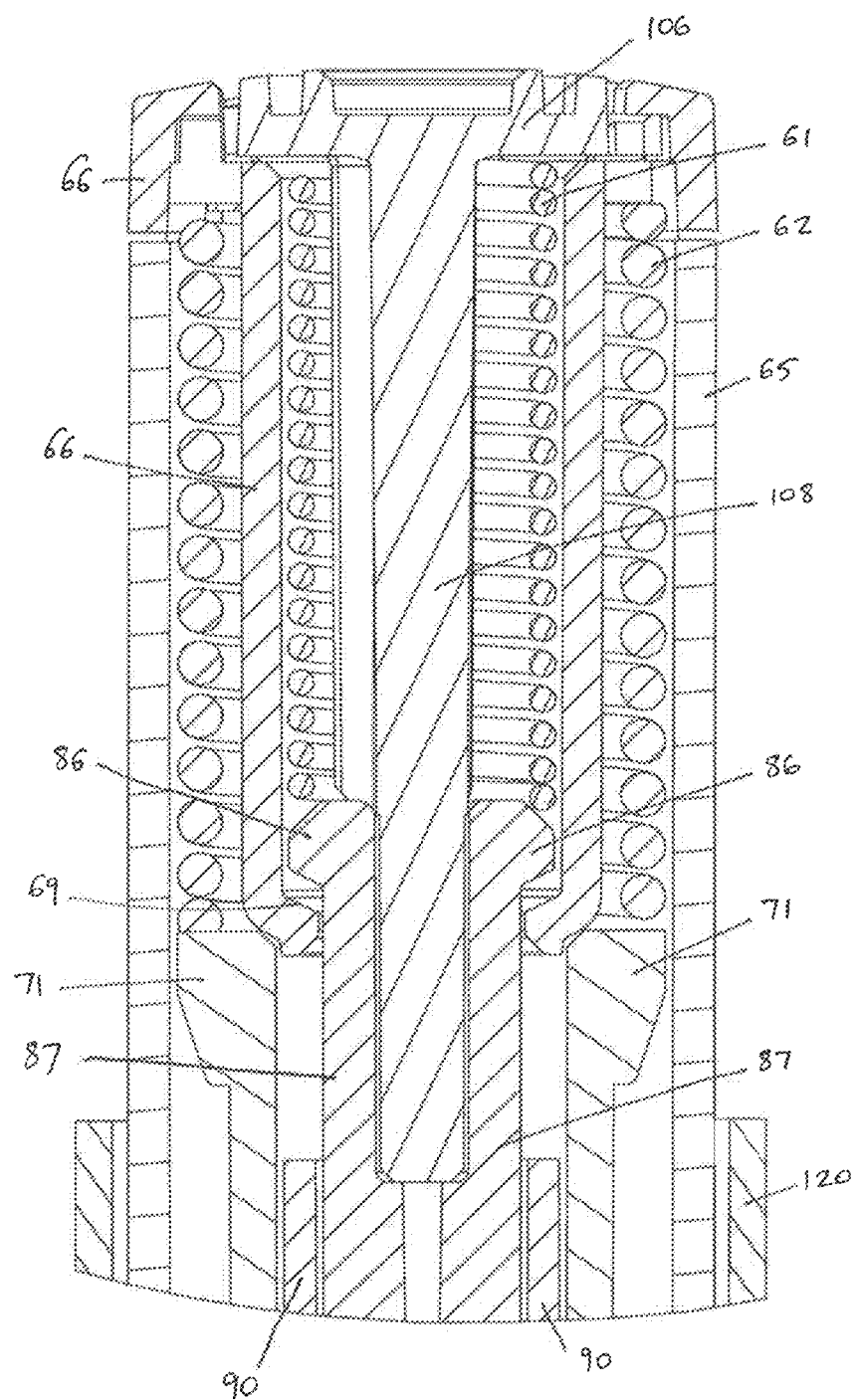
FIG. 6b is a second partial cross-section of the powerpack housing.

Before use of the autoinjector, the delivery spring 62 is positioned around the insertion spring 61. A two-spring mechanism, nested in this way has advantages. Firstly, by nesting one spring within the other, the length of the autoinjector is minimised. Secondly, the delivery spring can be made larger than the insertion spring. The force required to eject the drug through the needle is typically much greater than the force required to insert the needle into an injection site. The use of a smaller spring for needle insertion is therefore beneficial. The rear end of the powerpack assembly is shown in detail in FIGS. 6a and 6b. FIG. 6a is a first cross-section through the powerpack assembly and shows the insertion spring seated on a first ledge 67 formed on the upper powerpack housing 66. FIG. 6b is a second cross-section through the powerpack assembly, at ninety degrees to the cross-section of FIG. 6a, and shows the drive member 70 retained by a second ledge 69 formed on the upper powerpack housing.

The powerpack assembly is assembled as a separate component before it is coupled to the drug container and the rest of the autoinjector. In order to retain the insertion spring and delivery spring in a compressed condition, the powerpack housing engages the retaining means 100. The retaining means comprises a head portion 106 and a shaft portion 108 that extends from the head portion within the powerpack housing 64 and the drive member 70. The shaft portion 108 ensures that the drive member 70, and in particular lobes 86 on the second drive element 80, cannot disengage from the ledge 69 on the powerpack housing until the drive member is moved clear of the shaft portion 108.

Figure 7:
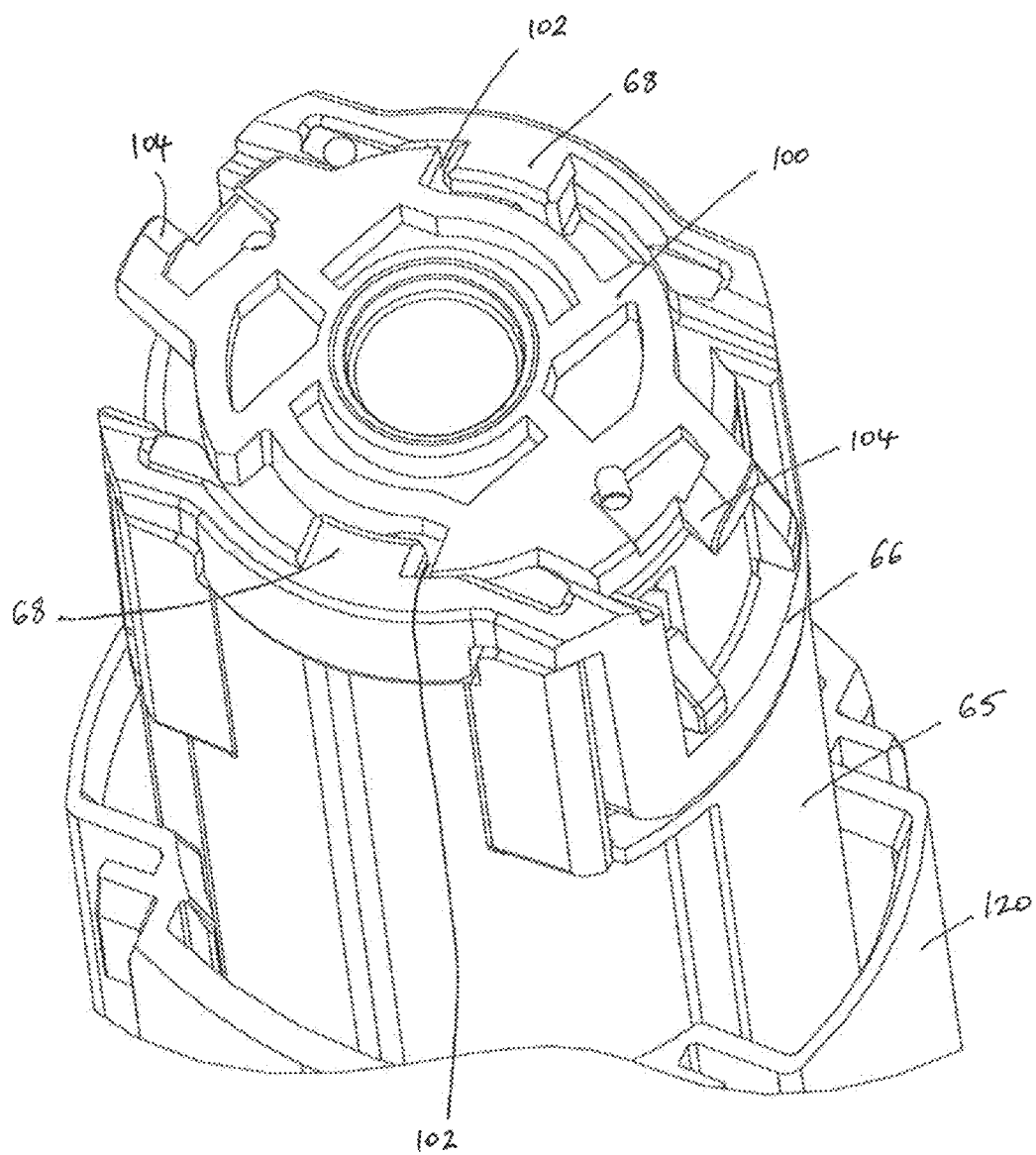
FIG. 7 is a top perspective view of the powerpack assembly.

FIG. 7 is a partial, perspective top view of the powerpack assembly, showing the retaining means 100 engaging the upper powerpack housing 66. The insertion spring 61 urges the powerpack housing away from the retaining means 100 but it is retained by the engagement of surfaces 102 on the retaining means under shelves 68 formed on the upper powerpack housing. The powerpack housing is released from the retaining means 100 by relative rotation between the powerpack housing and the retaining means. In particular, cam surfaces 104 are formed on the retaining means so that when the powerpack assembly is inserted into the outer housing, cam surfaces or protrusions 25 within the outer housing engage the cam surfaces on the retaining means and force the retaining means to rotate. The powerpack housing is prevented from rotating relative to the outer housing by engagement of the powerpack housing with the chassis and engagement of the chassis with the outer housing. The rotation of the retaining means 100 moves surfaces 102 out of engagement with shelves 68 so that the powerpack housing is disengaged from the retaining means.

Once the powerpack housing has been released from the retaining means 100 it is prevented from fully expanding by the engagement of the outer housing 20 with the lower housing 140, the engagement of the lower housing 140 with the chassis 120, the engagement of the chassis 120 with the drug container 10 and the engagement of the drug container 10 to the powerpack housing 64. The outer housing 20 is configured to engage the lower housing 140 as it drives the retaining means 100 out of engagement with the powerpack housing by rotating the retaining means.

As described, the insertion spring 61 engages the ledge 67 on the upper powerpack housing 66 to drive the powerpack housing and drug container assembly forward through the chassis as it expands. The drive spring 62 engages the powerpack housing 64 and the drive member 70 to drive the drive member and plunger through the drug container. The drive member 70 comprises three components. Specifically, the drive spring engages a spring bearing surface 72 on a first drive element 71. The first drive element 71 is coupled to a second drive element 80 and a third drive element 90. The multiple element drive member 70 is shown in FIGS. 8 and 9.

Figure 8:
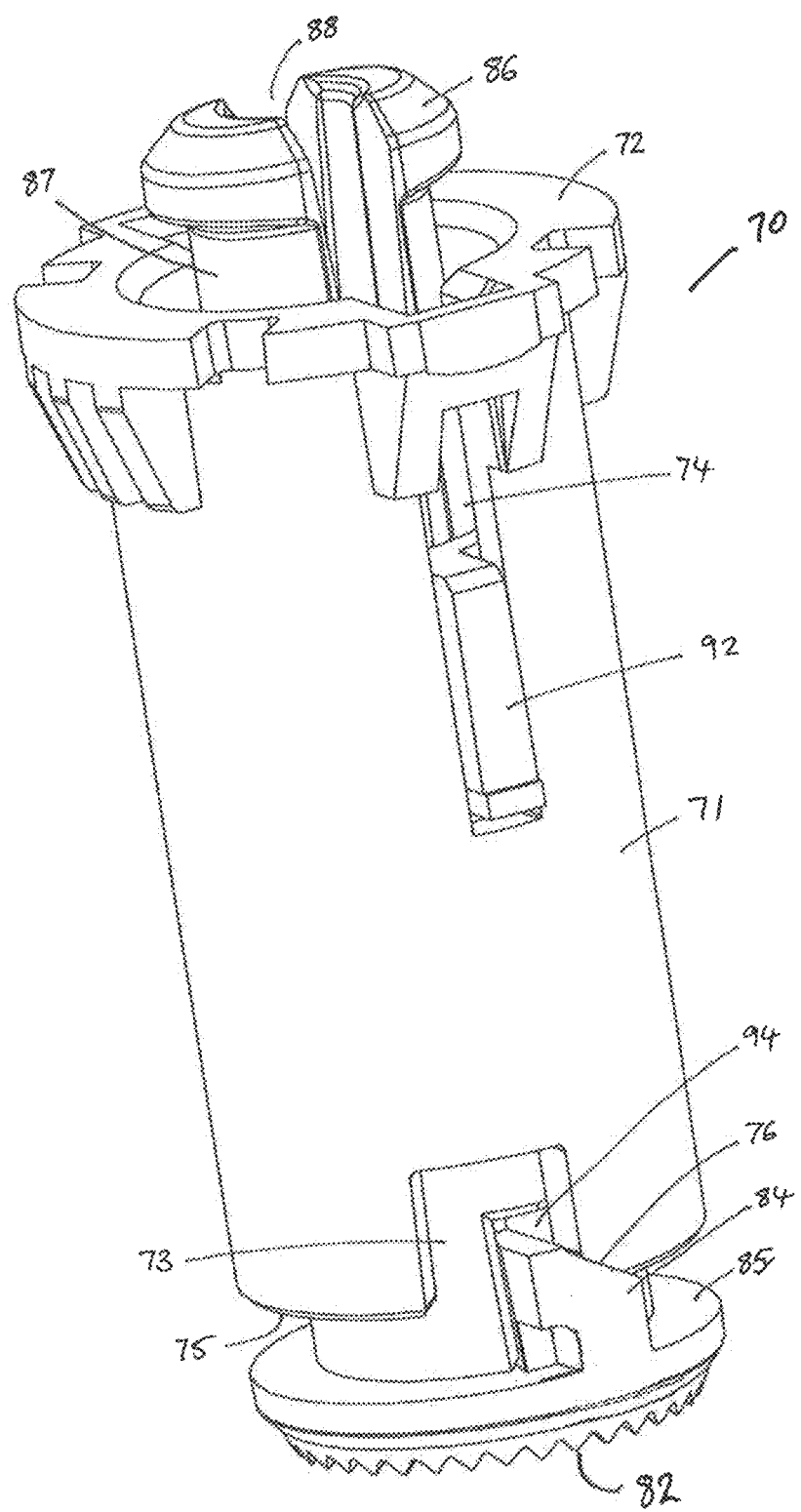
FIG. 8 is a perspective view of the drive member in an initial configuration.
Figure 9:
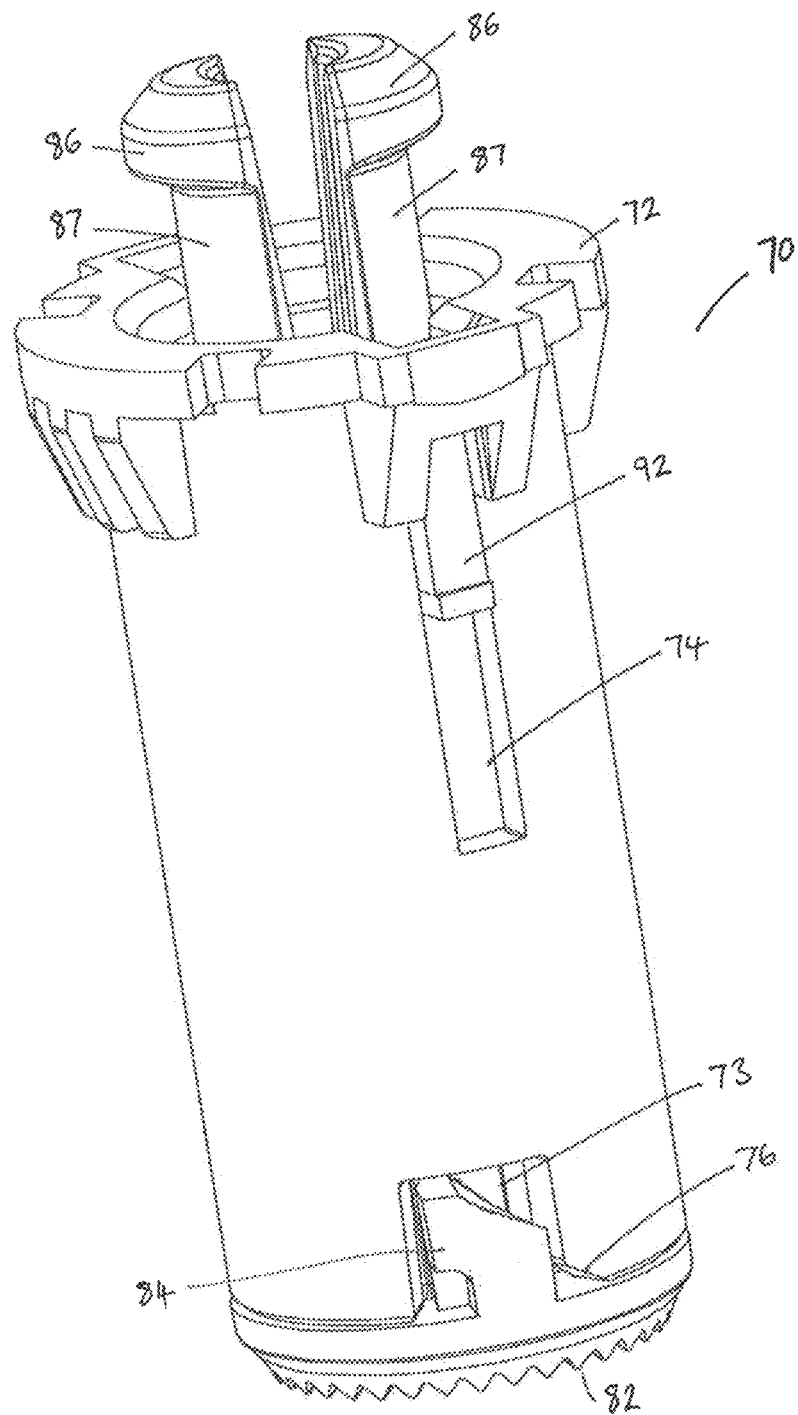
FIG. 9 is a perspective view of the drive member in a final configuration, after drug delivery.

The drive member 70 is shown in an initial configuration in FIG. 8, prior to delivery of the drug from the drug container. The first drive element 71 is essentially a circular cylindrical tube, within which a second drive element 80 is located. A first striking surface 75 on the first drive element is held apart from a first striking surface 85 on the second drive element by the engagement of the first drive element with a tooth 84 that extends from the first striking surface on the second drive element towards the first drive element. The second drive element comprises a foil contact surface 82 configured to contact and pierce the sealing foil 16 on the drug container 10. The foil contact surface 82 comprises a plurality of serrations to assist in piercing the foil seal. The second drive element 80 extends from the first striking surface 85, through the first drive element.

The second drive element is formed from a moulded plastics material and is divided at its rear end into a pair of flexible legs 87, at the rear end of each of which a lobe 86 is formed for engagement with the powerpack housing. A bore 88 is defined between the legs, into which the shaft portion 108 of the retaining means is received. The shaft portion of the retaining means prevents the legs 87 from deflecting inwardly to disengage from the ledge 69 on the upper powerpack housing.

The first drive element 71 comprises a cut-out 73 that is dimensioned to receive tooth 84 of the second drive element so that the first striking surface 75 on the first drive element and contact the first striking surface 85 on the second drive element. In order for tooth 84 to be received in the cut-out 73 the first drive element must be rotated relative to the second drive element. However, in an initial position, this is prevented by the third drive element 90. The third drive element 90 engages both the first drive element and the second drive element in the initial position. The third drive element in this embodiment is generally tubular and is positioned between the first drive element and the second drive element. A protrusion 92 on the third drive element engages a slot 74 formed in the first drive element to prevent relative rotation of the first drive element and the third drive element. The slot is dimensioned to allow axial movement i.e. movement in the direction of travel of the drive member on expansion of the drive spring, between the first drive element and the third drive element. A cut-out 94 in the third drive element engages the tooth 84 on the second drive element to prevent relative rotation between the second drive element and the third drive element. However, the third drive element is free to move axially relative to the second drive element.

As the drive member reaches the end of its forward travel through the drug container, the protrusion 92 on the third drive element engages a rear surface of the drug container 10. The third drive element is thus held by the drug container as the first and second drive elements continue to move forwards under the influence of the drive spring 62. When the cut-out 94 in the third drive element is disengaged from the tooth 84 as a result of the this relative axial movement between the third drive element and the second drive element, the first drive element 71 is free to rotate relative to the second drive element 80. Tooth 84 engages the first drive element on an angled surface 76 so that the action of the drive spring on the first drive element 71 forces it to rotate relative to the second drive element. When the tooth 84 is free to enter cut-out 73, the first drive element moves forward rapidly relative the second drive element as there is no significant resistance to that forward movement. The first striking surface on the first drive element then strikes the first striking surface on the second drive element at high speed, creating an audible single indicative of the drive member reaching the end of its travel. The final position is shown in FIG. 9.

A principle of operation of this "end-of-delivery" indication is to use a two-part drive member in which the two parts move together until at or near to the end of travel of the drive member, whereupon the two parts are free to move relative to one another under the action of a stored energy source to create an audible signal. It is advantageous to use the same energy source as is used to drive the drive member through the drug container. However, it should be clear that there are several options for the mechanism for locking and releasing the two parts of the drive member, which in the embodiment of FIGS. 8 and 9 is realised using the third drive member. For example, features within the powerpack housing might be provided to force the first drive element to rotate relative to the second drive element when the first drive element reaches a particular position within the powerpack housing.

A skin sensor assembly is provided forward of the drug container, which covers the needle both before and after use and which allows the autoinjector to be activated simply by removing a cap and pressing the autoinjector against an injection site.

Figure 10:
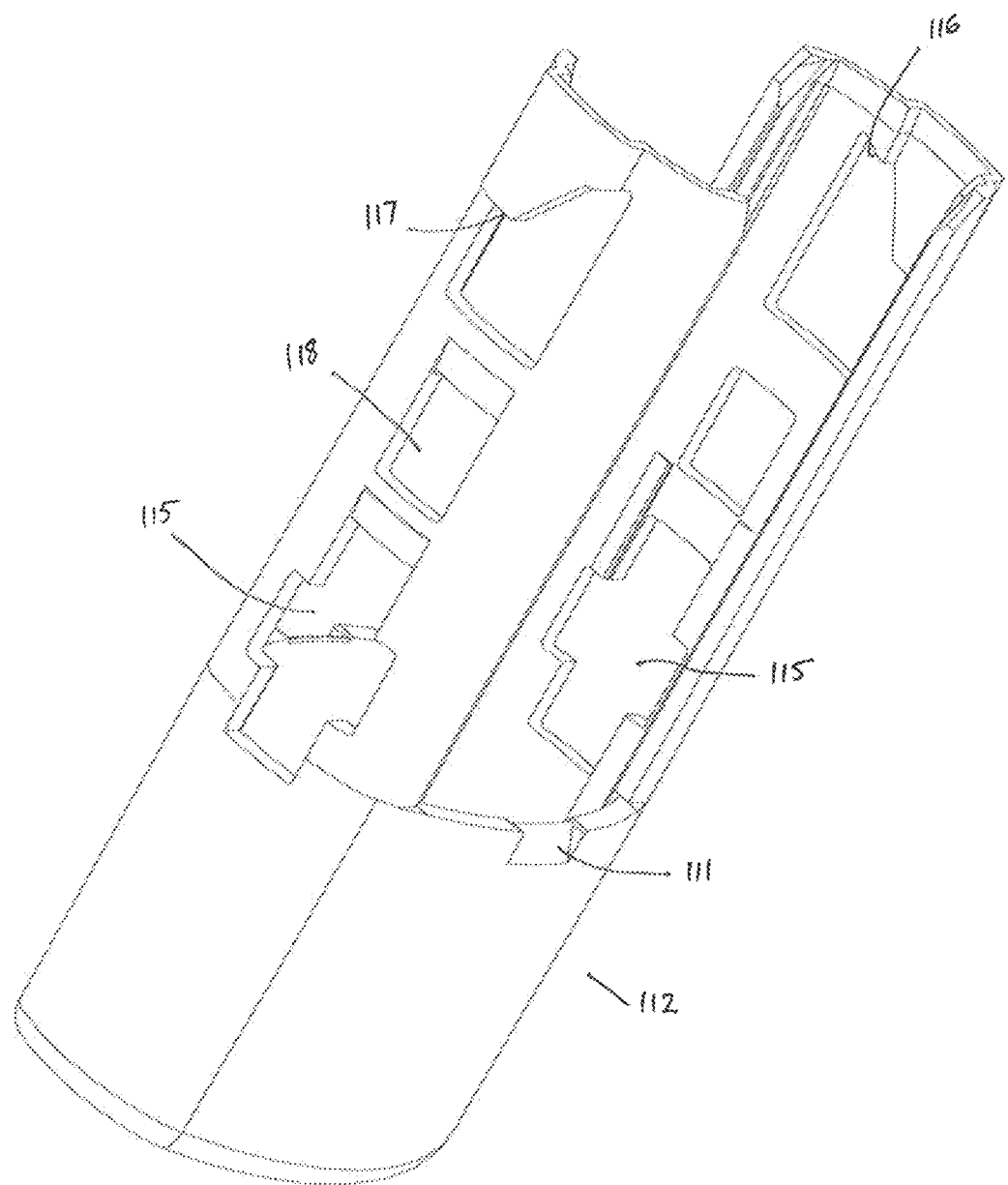
FIG. 10 is a perspective view of the skin sensor element.

The skin sensor assembly comprises a skin sensor element 112, shown in FIG. 10, and skin sensor spring 114 that is held between the skin sensor element and the chassis. This can be seen clearly in FIG. 3. In operation, the skin sensor element interacts with the chassis 120 shown in FIG. 11 and the lower housing 140 shown in FIG. 12.

Figure 11:
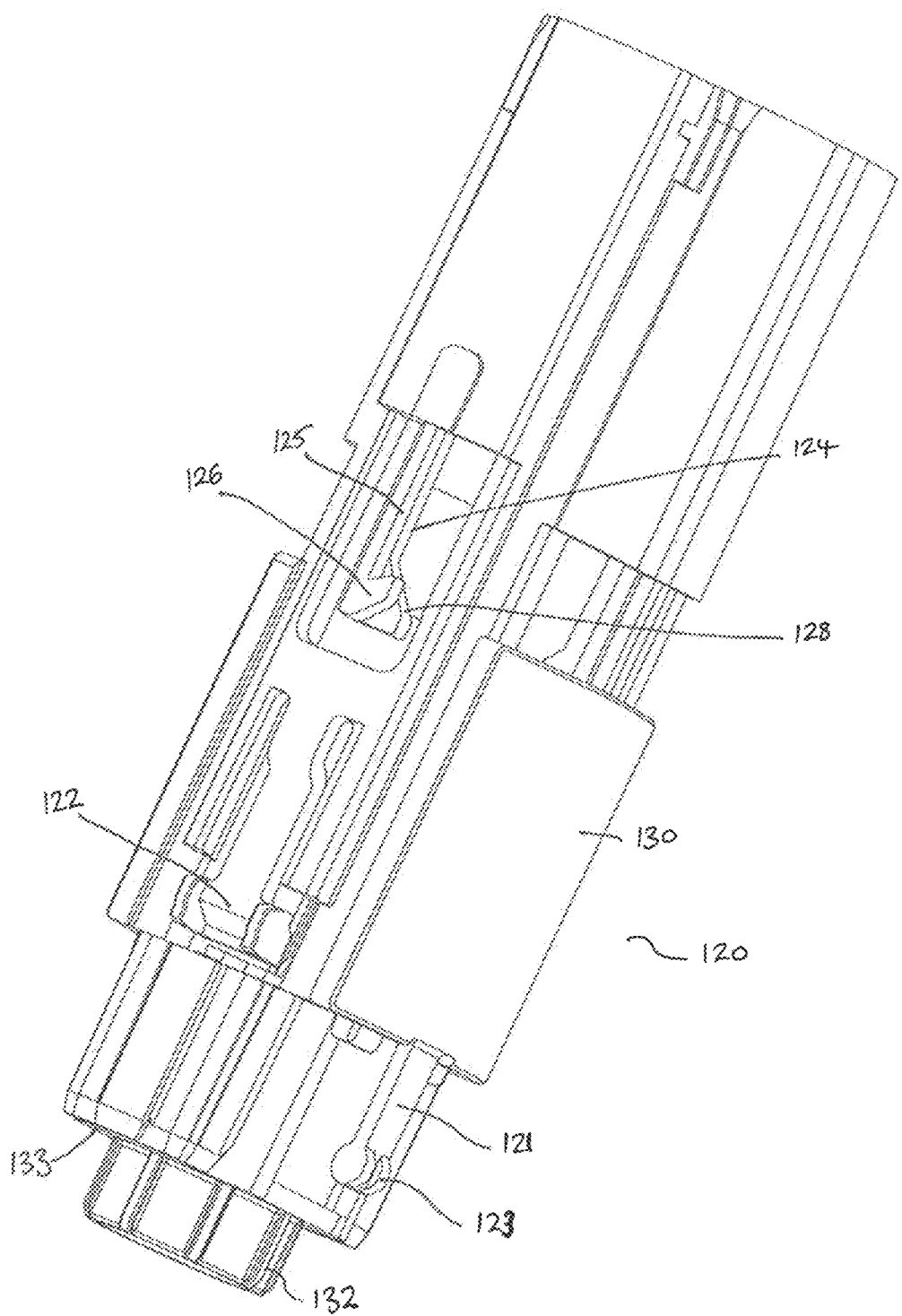
FIG. 11 is a perspective view of the internal housing.
Figure 13A:
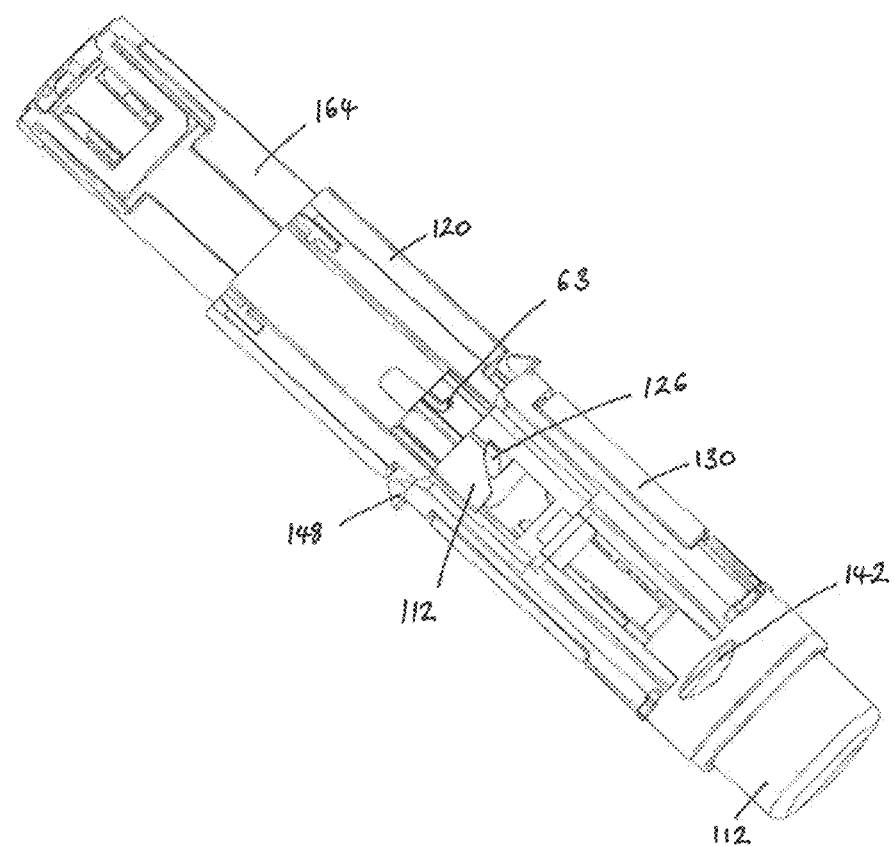
FIG. 13a is a side view of the device with the upper housing and cap removed, showing the skin sensor element in an initial position.

FIG. 11 is a perspective view of the chassis 120. The chassis is formed from a transparent plastic material and includes two window portions 120, which align with the windows 22 formed in the outer housing 20. The lower housing 140 clips to the chassis around the window portion 130, as shown in FIG. 13a. Latches 122 are formed so that they can be flexed outward, out of engagement with the drug container 10. The chassis has a front end 132 of reduced diameter, which prevents the drug container from travelling beyond an insertion position. A bearing surface 133 is provided against which the skin sensor spring 114 sits.

The chassis 120 also includes flexible arms 121 formed below the window portions 130. The flexible arms 121 each comprise a bulb 123 at their free end that abuts a rear end of the skin sensor element 112. The bulb 123 (in combination with the cap and/or upper housing) prevents the skin sensor element being moved rearward to a position in which the latches 122 can release the drug container 10, as described with reference to FIG. 15. The chassis also includes latching elements 124. Each latching elements 124 comprises a flexible arm 125 extending from the body of the chassis towards a front end of the device, and a hook 126 and cam head 128 on the end of the flexible arm. The hook 126 is configured to engage the skin sensor element 112. The cam head 128 is positioned inward of the hook and is configured to engage the powerpack housing 64. Inward in this context is relative to the outer housing. The latching elements 124 on the chassis do not extend inwardly of the surrounding portion of the chassis in order to engage the powerpack or skin sensor element. This is advantageous from a moulding perspective.

Figure 12:
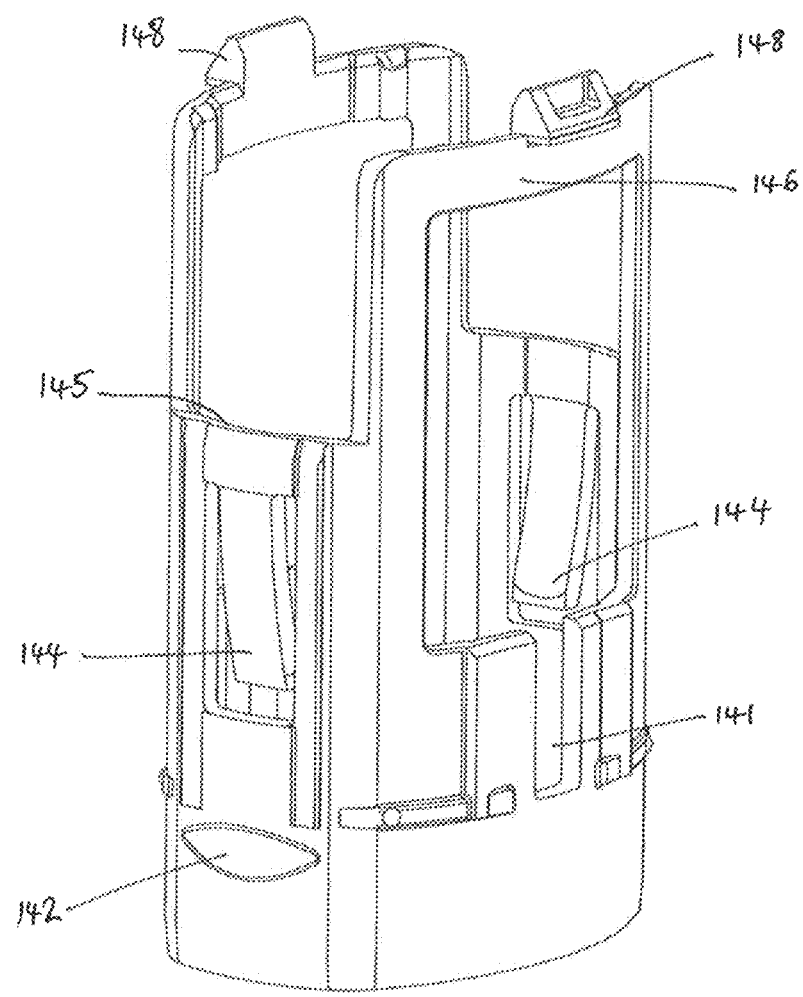
FIG. 12 is a perspective view of lower housing.

FIG. 12 is a perspective view of the lower housing 140. The lower housing is secured to the chassis by the clipping of portion 146 around window portion 130 of the chassis. The lower housing 140 includes a pair of second latching elements 144 that, in the initial position are received in openings 115 of the skin sensor element 112. The lower housing includes recesses 142 for engagement with the cap 30. Surface 145 acts to limit movement of the skin sensor beyond a fully extended position, as will be described. The lower housing also includes slots 141, into which flexible arms 121 of the chassis are received. Lugs 148 on the lower housing engage recesses 24 formed in the outer housing. In an initial position, prior to use, and as shown in FIGS. 2 and 3, the skin sensor element 112 is urged away from the chassis by the skin sensor spring 114. It is retained to the chassis by engagement of surfaces 116 with latching elements 124. The second latching elements 144 on the lower housing, in the initial position, are received in openings 115 of the skin sensor element 112.

FIGS. 13a-13d show the sequence of operation of the skin sensor assembly, and are side views of the device with the outer housing and cap removed. FIG. 13a shows the device with the cap removed but prior to use. The skin sensor element 112 is retained against the action of the skin sensor spring by the latching element 124. Specifically hook 126 on the latching element 124 engages surface 114 on the skin sensor element.

Figure 13B:
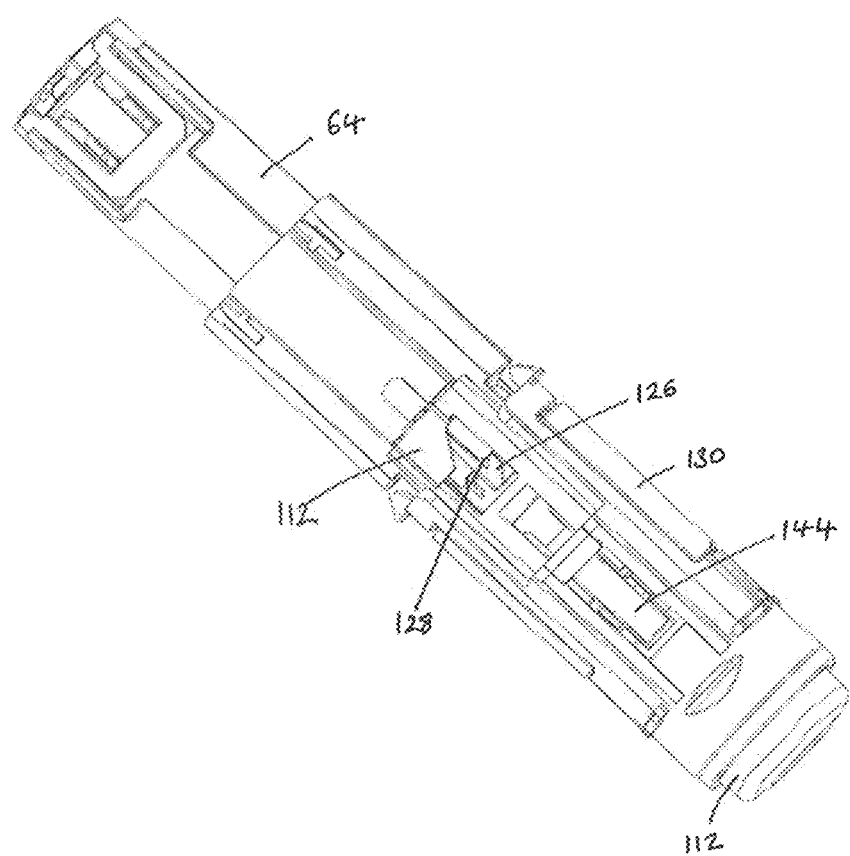
FIG. 13b is a side view of the device with the upper housing and cap removed, showing the skin sensor element in a retracted position.

FIG. 13b shows the skin sensor element 112 pushed back, as it would be if the skin sensor element were pressed against an injection site. In this position, the hook 126 is clear of the surface 116. The second latching elements 144 are still received in opening 115 of the skin sensor element. However, the wider portions of opening 115 are now aligned with the position of latches 122 on the chassis. In the position shown in FIG. 13b, the latches 122 no longer retain the drug container 10, as they can be pushed outwards into the opening 115 in the skin sensor element. Accordingly, the drug container is free to move forward and the insertion spring 61 expands to move the powerpack assembly and drug container to an insertion position, as shown in FIG. 13c.

Figure 13C:
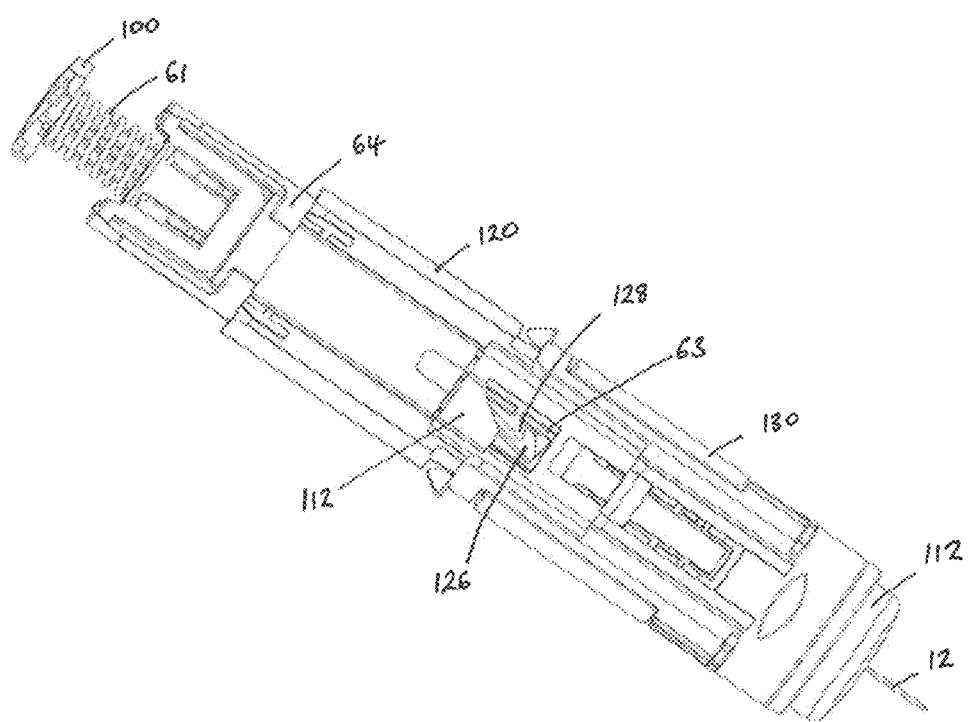
FIG. 13c is a side view of the device with the upper housing and cap removed, showing the skin sensor element in a retracted position and with the skin sensor latching element deflected by the powerpack assembly.

In FIG. 13c the drug container is in an insertion position, and needle 12 is clearly extending beyond the skin sensor element 112. In this position, the powerpack assembly has moved forward so that protrusions 63 on the powerpack housing 64, only an upper end of which can be seen in FIG. 2, have pushed against cam head 128 and so have deformed arm 124. The deformation of arm 124 moves the hook 126 out of the path of surface 116 when it moves forward.

Figure 13D:
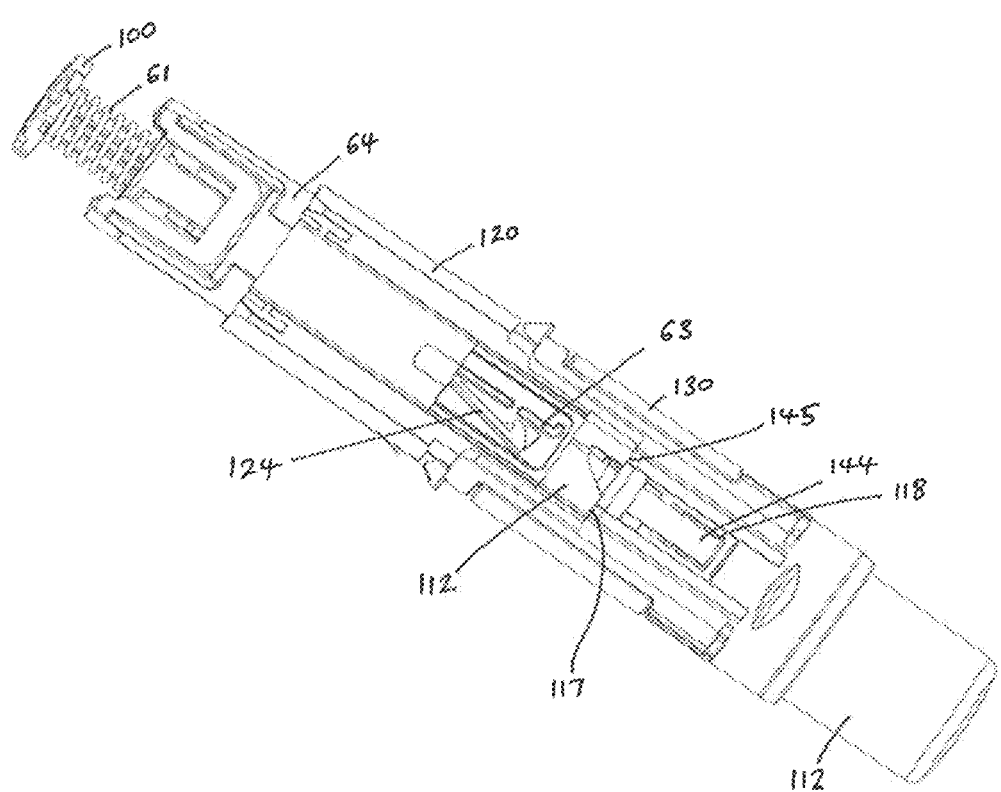
FIG. 13d is a side view of the device with the upper housing and cap removed, showing the skin sensor element and powerpack assembly in a final position.

When the device is removed from the injection site, the skin sensor spring urges the skin sensor element forward. As the arm is deformed, the surface 116 can move past hook 126. The skin sensor element can then move to a fully extended position as shown in FIG. 13d. In this position the skin sensor element covers the needle again. The skin sensor element is retained to the chassis and prevented from further forward movement by the surface 117 on the skin sensor element abutting the surface 145 on the lower housing. The second latching elements 144 engage with aperture 118 in the skin sensor element 112 to prevent the skin sensor element from being moved back against the skin sensor spring. The second latching elements can ride over sloped surface 119 on the skin sensor element as it moves to its fully extended position to snap into the aperture 118, whereupon the skin sensor element is locked in a fully extended position.

The latching mechanism for the skin sensor and for retaining and releasing the drug container is all positioned on two opposite sides of the device. This allows the window 22 to remain unobscured throughout operation of the device. This allows the drug to be easily inspected before use and for the progress of the drug delivery to be observed through the window 22.

The device shown in FIGS. 1 to 13 includes a mechanism to prevent activation prior to removal of the cap. FIG. 14 is a perspective view of the cap 30. The cap is formed from a moulded plastics material and comprises protrusions 34 that are configured to engage recesses 142 on the lower body, as shown in FIG. 2. The upstanding central tube comprises the hooks 32 shown in FIG. 2, for retaining the needle shield. The cap also includes tongues 36 that extend within a space between the outer housing and the chassis when the cap is fitted to the device, as shown in FIG. 3.

Figure 15:
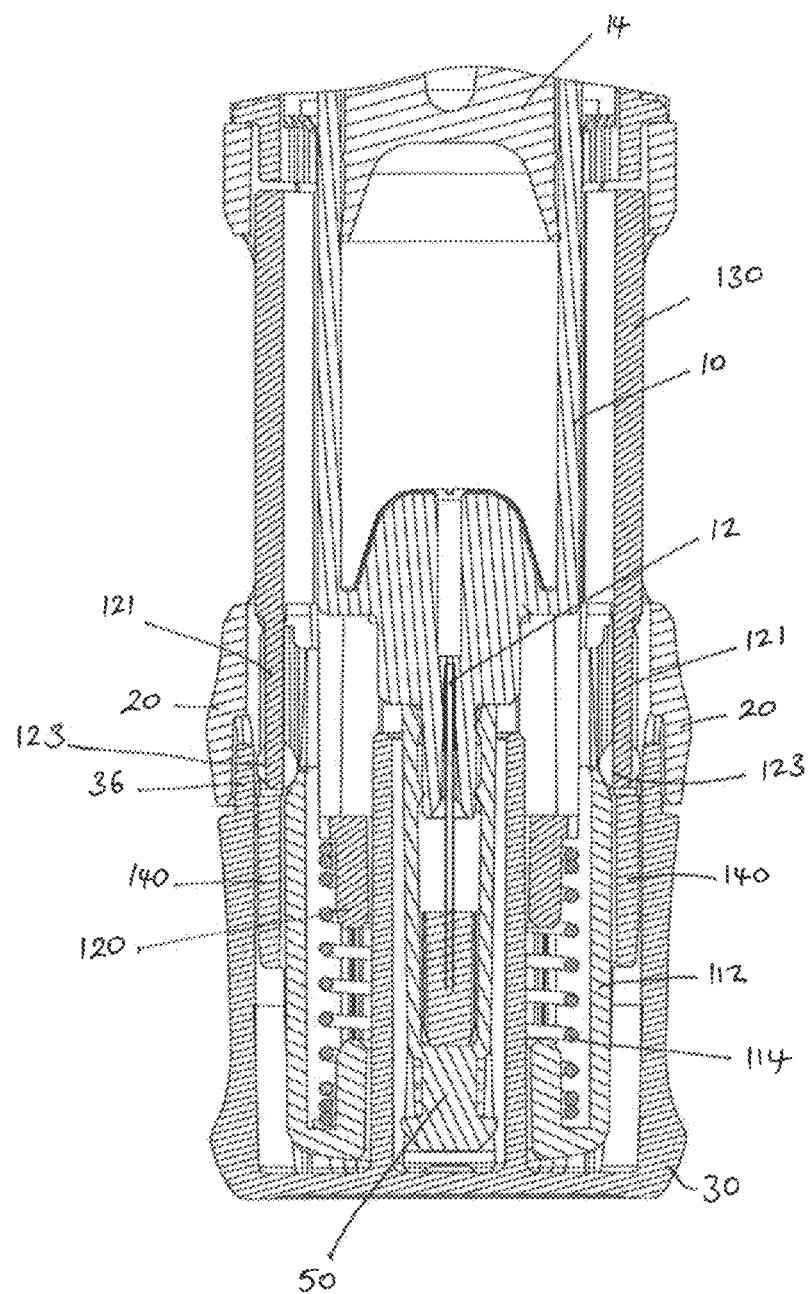
FIG. 15 is a cross-section view of the front end of the device prior to removal of the cap.

FIG. 15 is a detail view of the front end of the device as shown in FIG. 3. It can be seen that the tongues 36 on the cap are adjacent flexible arms 121 formed on the chassis, and shown more clearly in FIG. 11. The flexible arms 121 comprise a bulb 123 that abuts a rear end of the skin sensor element 112. The bulb 123 prevents the skin sensor element being moved rearward to a position in which the latches 122 can release the drug container 10. So, when the cap is engaged to the lower housing 140, the device cannot be activated.

When the cap is removed, the arms 121 can be pushed outwardly by the skin sensor element into the space vacated by the tongues 36, as it the skin sensor is moved rearward. The skin sensor element and bulbs 123 are shaped to allow this to happen smoothly. The lower housing includes apertures 141 into which the arms 123 can deflect.

FIGS. 16a to 16g illustrate the sequence of operation of the device of the first embodiment. FIGS. 16a to 16g are cross-section views, similar to FIG. 2, but with the cap removed.

Figure 16A:
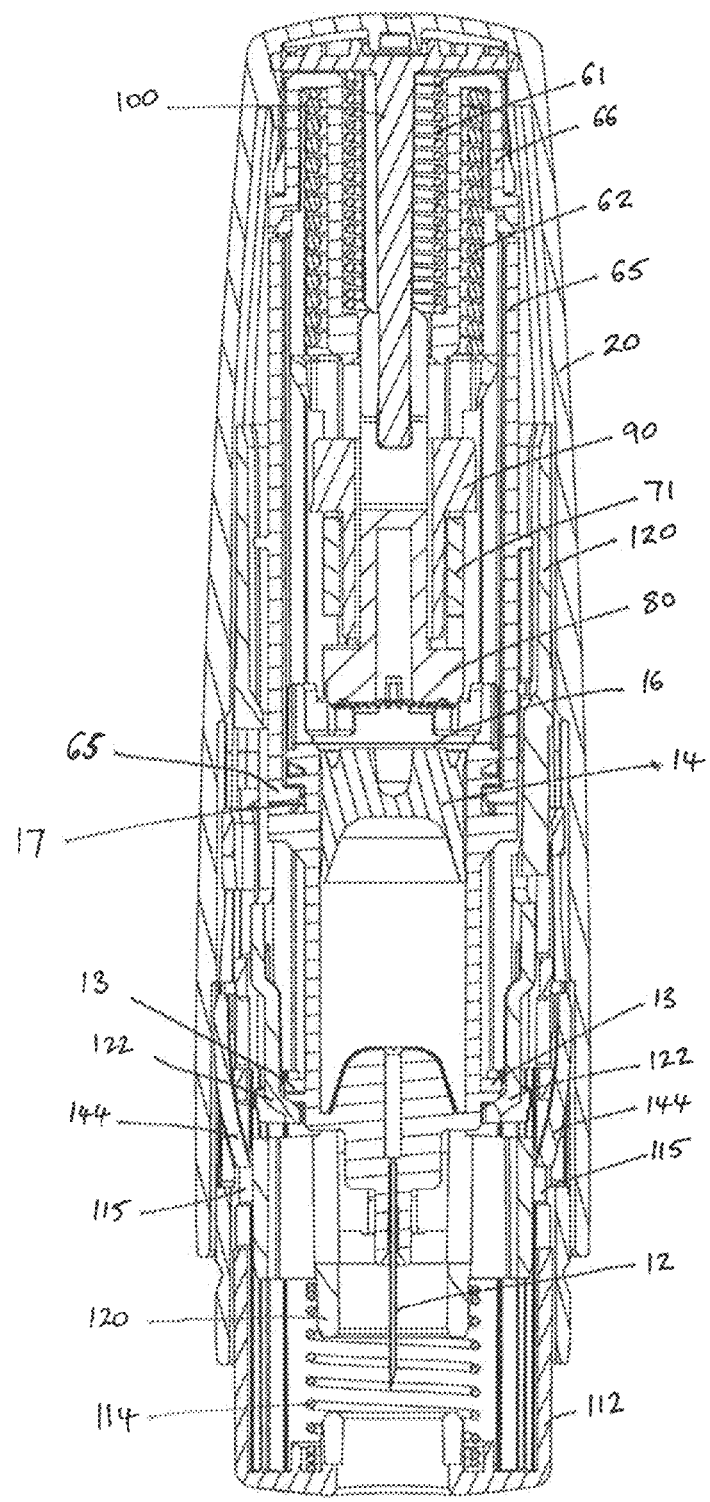
FIG. 16a-16g are cross-section views of the first embodiment, illustrating the sequence of operation.

FIG. 16a shows the device immediately after cap removal, but prior to the pressing of the skin sensor element against an injection site. It can be seen that the needle shield assembly has been removed together with the cap.

Figure 16B:
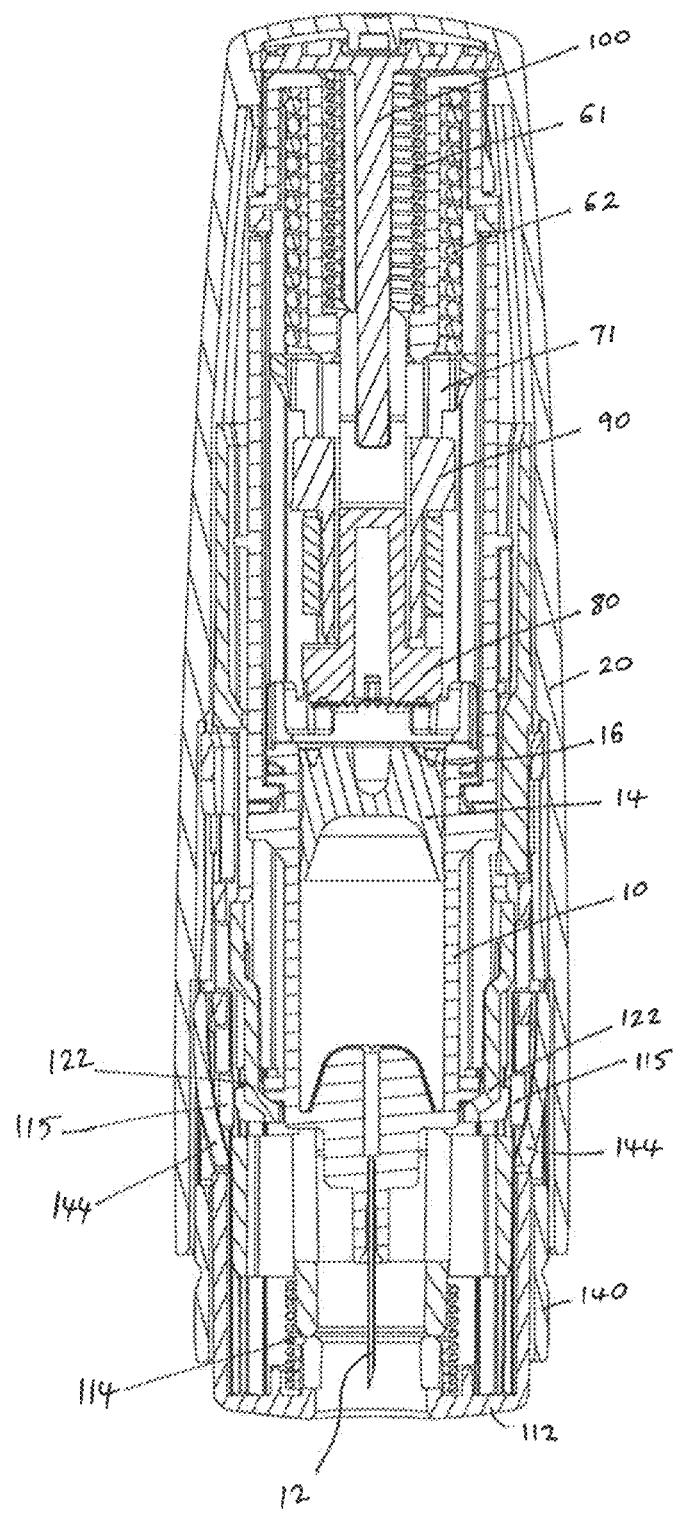

FIG. 16b shows the device with the skin sensor element pushed back. Second latching elements 144 on the lower housing prevent the skin sensor from moving further back. In this position, the latches 122 on the chassis are free to bend out into the windows 115, but have not yet done so.

Figure 16C:
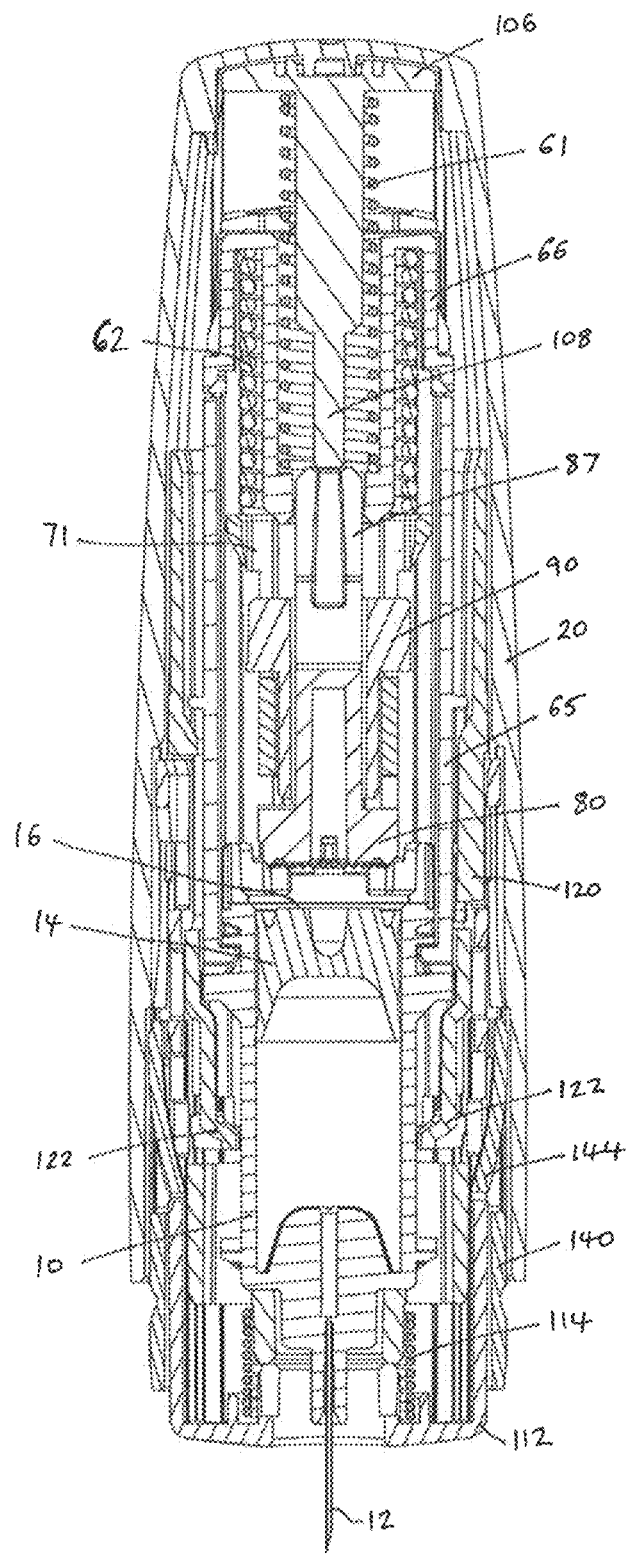

FIG. 16c shows the drug container 10 and powerpack housing 64 moved to an insertion position by the expansion of insertion spring 61. In this position, the needle 12 is inserted into the injection site. The second drive element 80 is just clear of the shaft portion 108 of the retaining means 100. This means that legs 87 can be squeezed together to disengage from the lugs 86 from surface 69 on the powerpack housing 64. The protrusions 63 on the powerpack housing has deflected the latching arms 124 so that the skin sensor element 112 is free to move forward to a fully extended position once it is removed from the injection site.

Figure 16D:
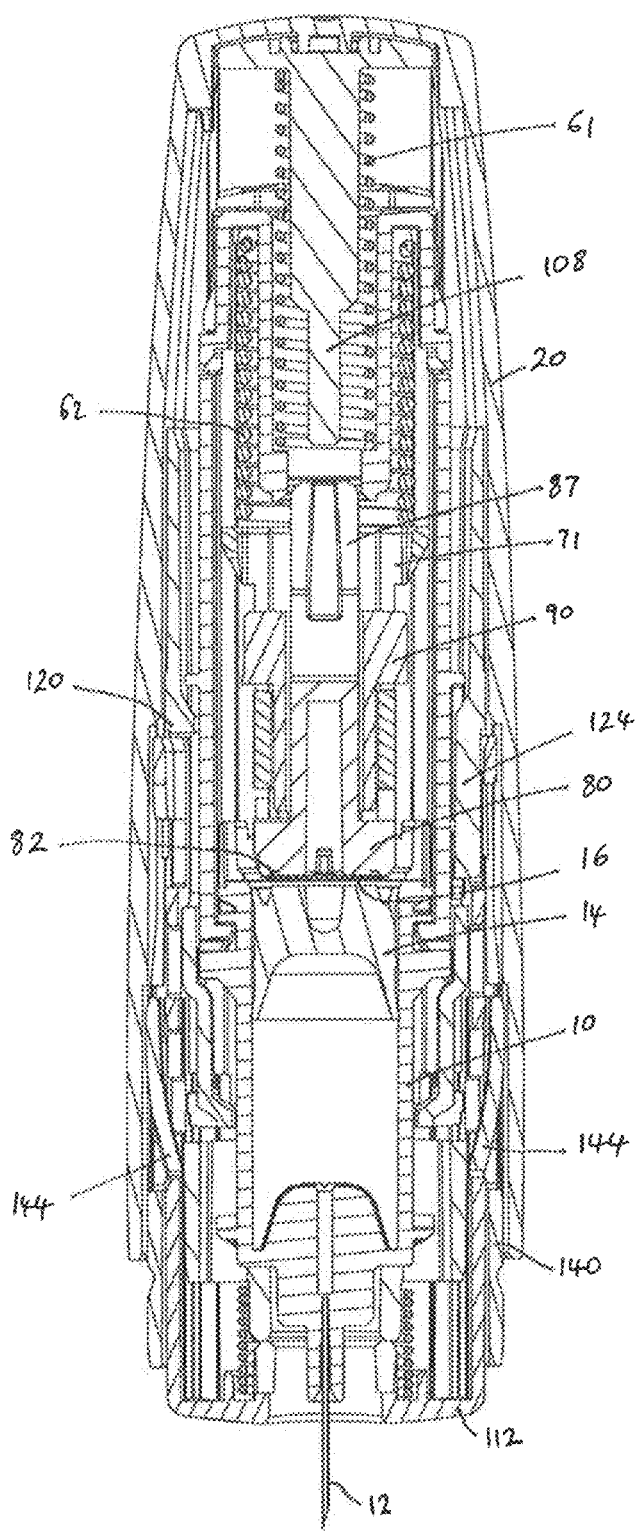

FIG. 16d shows the drive member disengaged from the powerpack housing and at the point of first contact of the drive member with the sealing foil. The drive spring is expanding to urge the drive member forward.

Figure 16E:
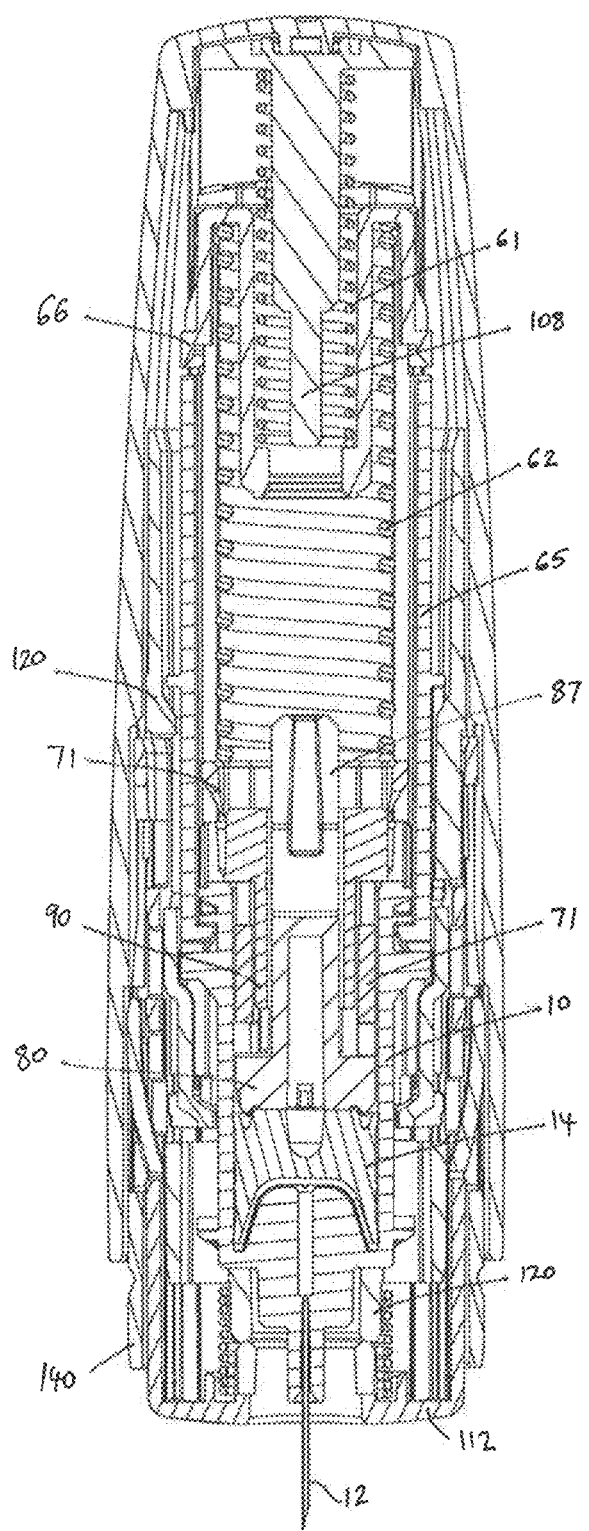

FIG. 16e shows the drive spring further expanded and the drive member further forward. The foil has been ruptured and the plunger has been moved through the drug container and almost all the drug has been ejected. At this point, the third drive element has engaged the rear end of the drug container and so moved back relative to the second drive element. In this position, the drive element is no longer engaged to the second drive element, and the second drive element is able to rotate relative to the first drive element, as described with reference to FIGS. 8 and 9.

Figure 16F:
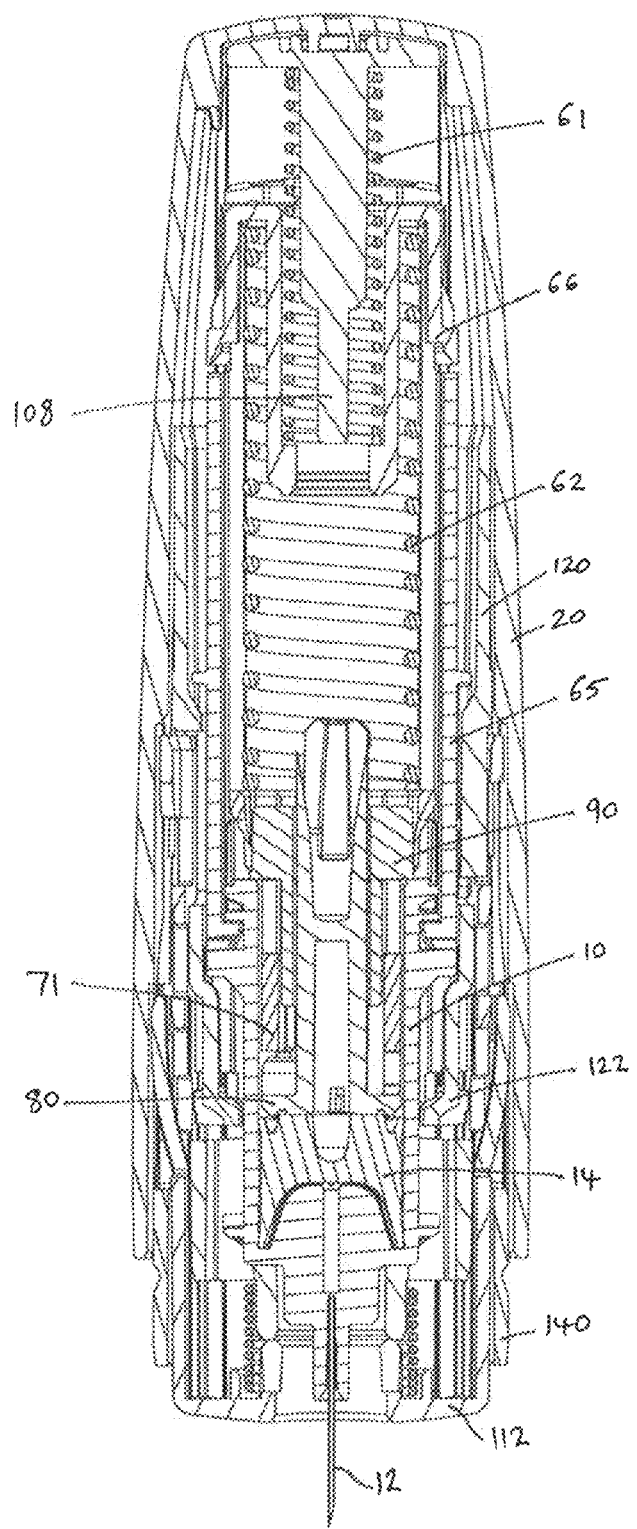

FIG. 16f shows the first drive element driven forward onto the second drive element, with the second drive element rotated, to provide an audible indication of the end of drug delivery. The plunger is in a fully forward position, with the intended volume of drug ejected. At this point, the user can remove the device from the injection site.

Figure 16G:
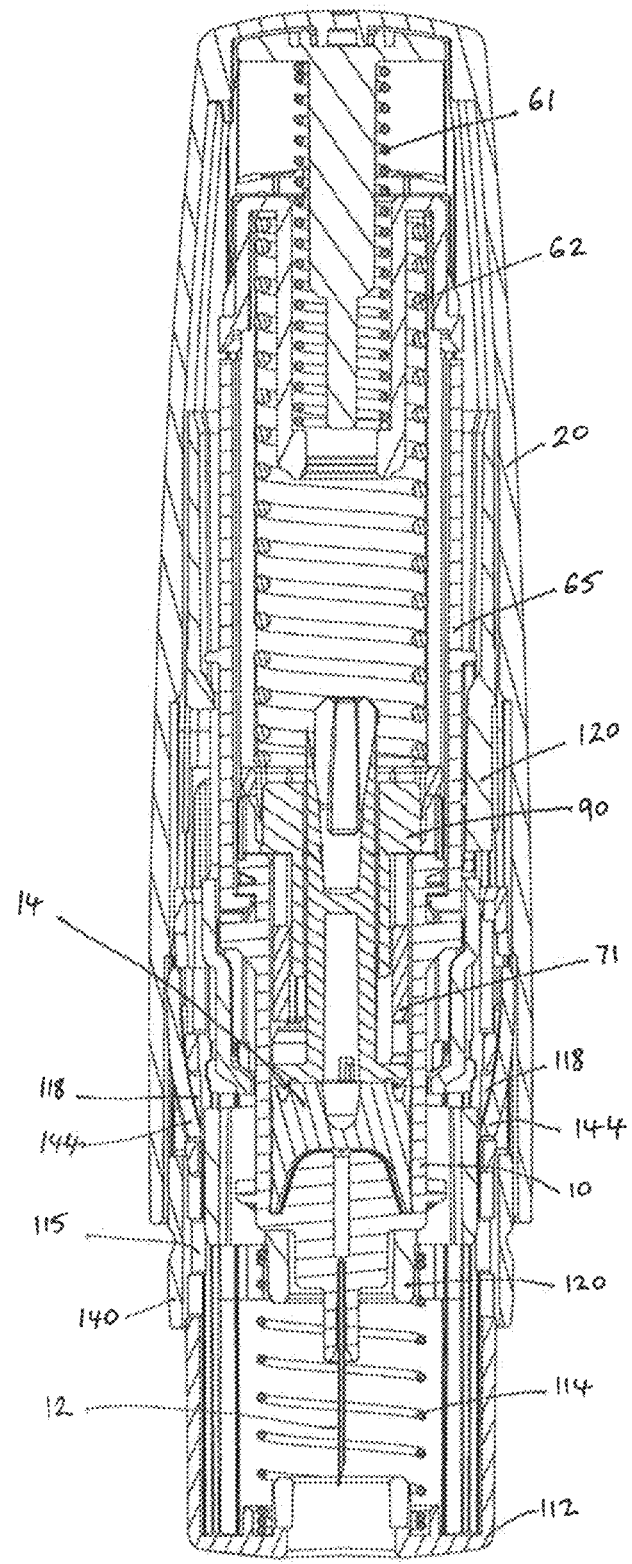

FIG. 16g shows the device after it has been removed from the injection site, with the skin sensor element in a fully extended position, locked and covering the needle. As described with reference to FIG. 13d, the skin sensor element is retained to the chassis and prevented from further forward movement by surface 117 on the skin sensor element abutting the surface 145 on the lower housing. The second latching elements 144 engage with aperture 118 in the skin sensor element 112 to prevent the skin sensor element from being moved back against the skin sensor spring.

It can be seen from FIG. 2 and FIGS. 16a-c, that the drive member 70 and all of the other components of the device are held apart from the sealing foil 16 until the time at which the sealing foil is ruptured. Prior to use, the drive member 70 is held a predetermined distance from the sealing foil 16. The powerpack housing 64 is fixed to the sides of the drug container and does not contact the sealing foil. During the needle insertion stage of operation, the sealing foil 16 remains untouched. This arrangement ensures that the sealing foil can be tested before the drug container is assembled to the rest of the autoinjector, and the sealing foil then remains untouched until the point of drug delivery. This reduces the possibility of contamination or loss of drug before delivery.

Figure 17:
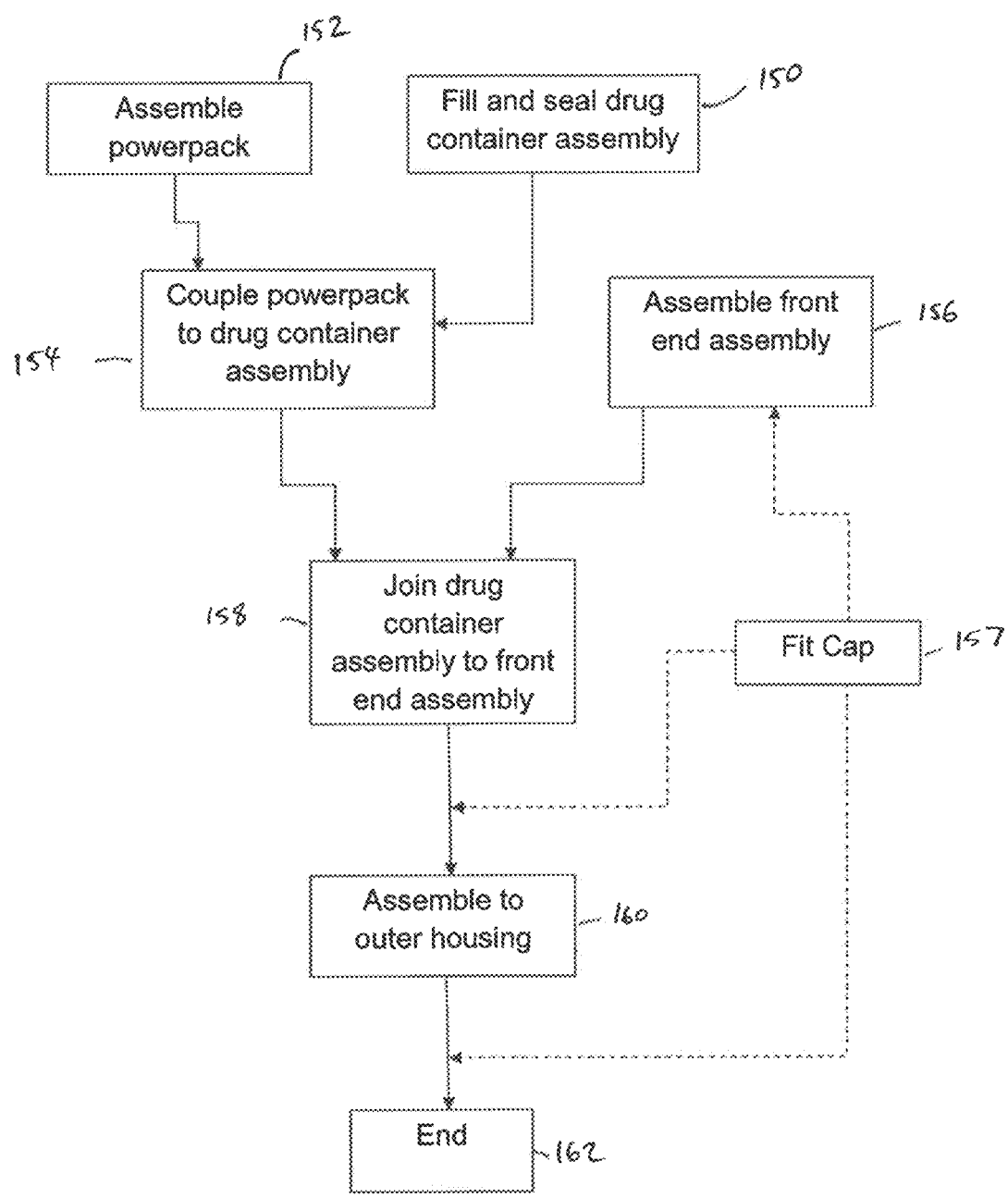
FIG. 17 is a schematic diagram illustrating the assembly process of an autoinjector in accordance with the first embodiment of the invention.

FIG. 17 is a schematic diagram illustrating the sequence of assembly of an autoinjector of the first embodiment. In step 150, the drug container assembly 10, including the needle 12 and needle shield 50 is filled with dose of drug and a plunger 14, and then sealed by a sealing foil 16. This is carried out in a sterile environment. Independently, in step 152, the powerpack assembly is assembled, with the retaining means holding the drive and insertion springs in a compressed state. In step 154 the filled drug container assembly in then fitted to the powerpack assembly, the lower powerpack housing clipping to the drug container 10. In step 156, the front end of the device, including the chassis, skin sensor element, skin sensor spring, and lower housing are assembled. The cap is typically coupled to the front end assembly at this stage, but this is shown as a separate step 157. In step 158 the front end assembly is coupled to the drug container assembly and powerpack assembly. The drug container assembly is retained by latching arms on the chassis. In step 160, the outer housing is placed over the powerpack assembly and engages with the lower housing 140. The cam surfaces 25 on the outer housing 20 engage the retaining means 100 and force the retaining means to rotate out of engagement with the powerpack housing 64 just before the lugs 148 on the lower housing engage recesses 24 formed in the outer housing. The insertion spring 61 is allowed to expand a small amount as the powerpack housing disengages from the retaining means, but it is held in a second compressed state by the action of latches 122 on the chassis engaging the drug container 10. In the second compressed state, the insertion spring still stores enough energy to insert the needle 12 into an injection site by pushing the drug container to the insertion position.

The cap 30 is typically assembled to the lower housing 140 during assembly of the front end assembly, but may be added after the powerpack and front assembly are joined or after the outer housing has been fitted to the lower housing. These options are illustrated in FIG. 17 as step 157.

The autoinjector is fully assembled and ready for use at step 162. This production sequence has the advantage that the powerpack assembly can be produced independently of the other components and transported and stored separately. Steps 156, 157, 158 and 160 are very simple and easily automated.

The first described embodiment also has the advantage that different length and shaped outer housing can be used for different drugs with the same powerpack assembly. The features 25 used to rotate the retaining means out of engagement with the powerpack housing 64 do not need to be manufactured with the same tight tolerances on dimensions that the shaft portion 108 of the retaining means requires. It is therefore a simple matter to provide different outer housings to provide a distinctive appearance for devices for particular drugs or for devices associated with particular brands. Users can then quickly recognise if they have the appropriate device. Different outer housing may also be provided to suit different user groups that may have different specific requirements e.g. they may have limited manual dexterity.

Figure 18:
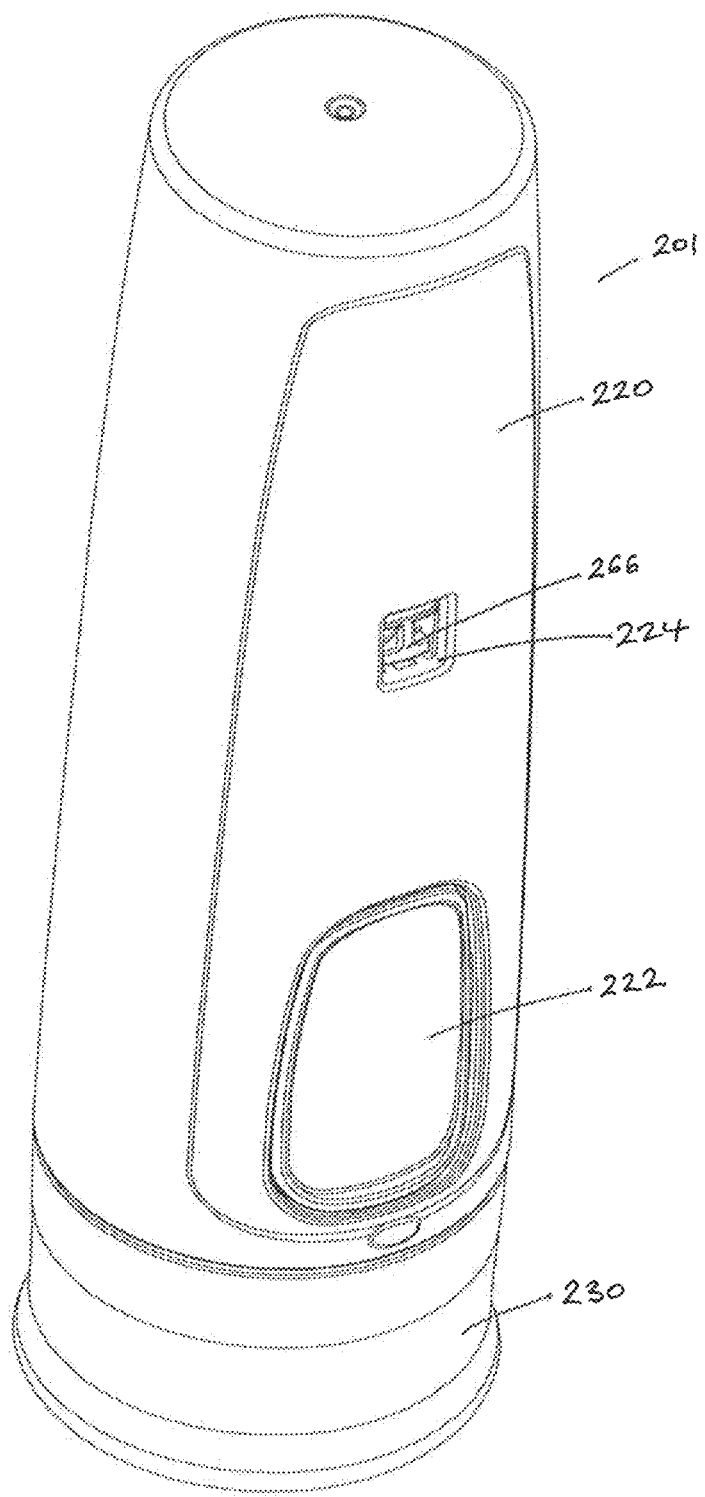
FIG. 18 is a perspective view of an autoinjector in accordance with a second embodiment of the invention, prior to use.

FIG. 18 is a perspective view of an autoinjector 201 in accordance with a second embodiment of the invention, before use. The autoinjector 201 comprises an outer housing 220, having a viewing window 222 through which a drug within the autoinjector can be inspected. A cap 230 is provided to cover the needle insertion end of the device and to prevent inadvertent activation of the device. The autoinjector is compact, being approximately 10 cm long and fits easily in a user's hand.

Figure 19:
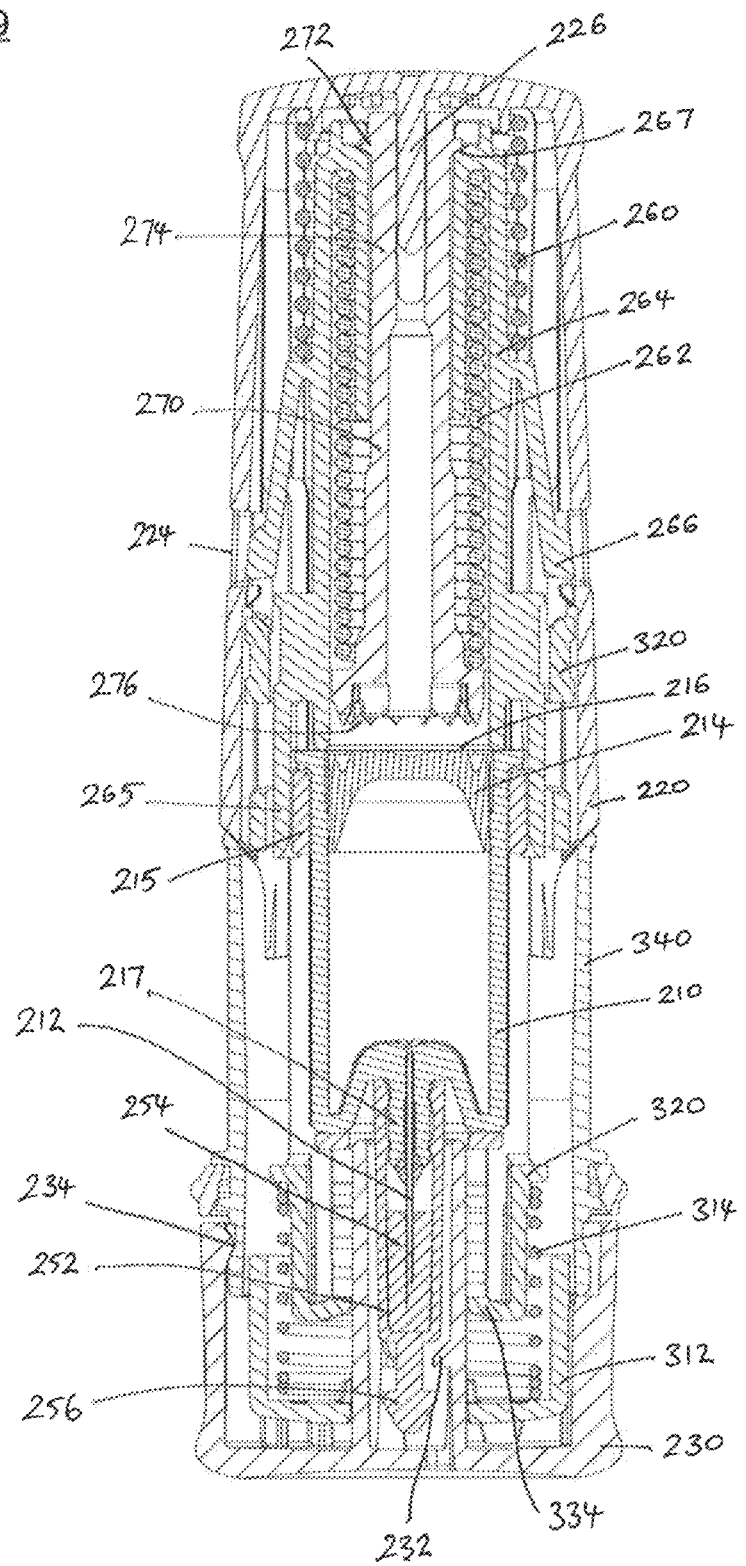
FIG. 19 is a first cross-section through the autoinjector of FIG. 18.
Figure 20:
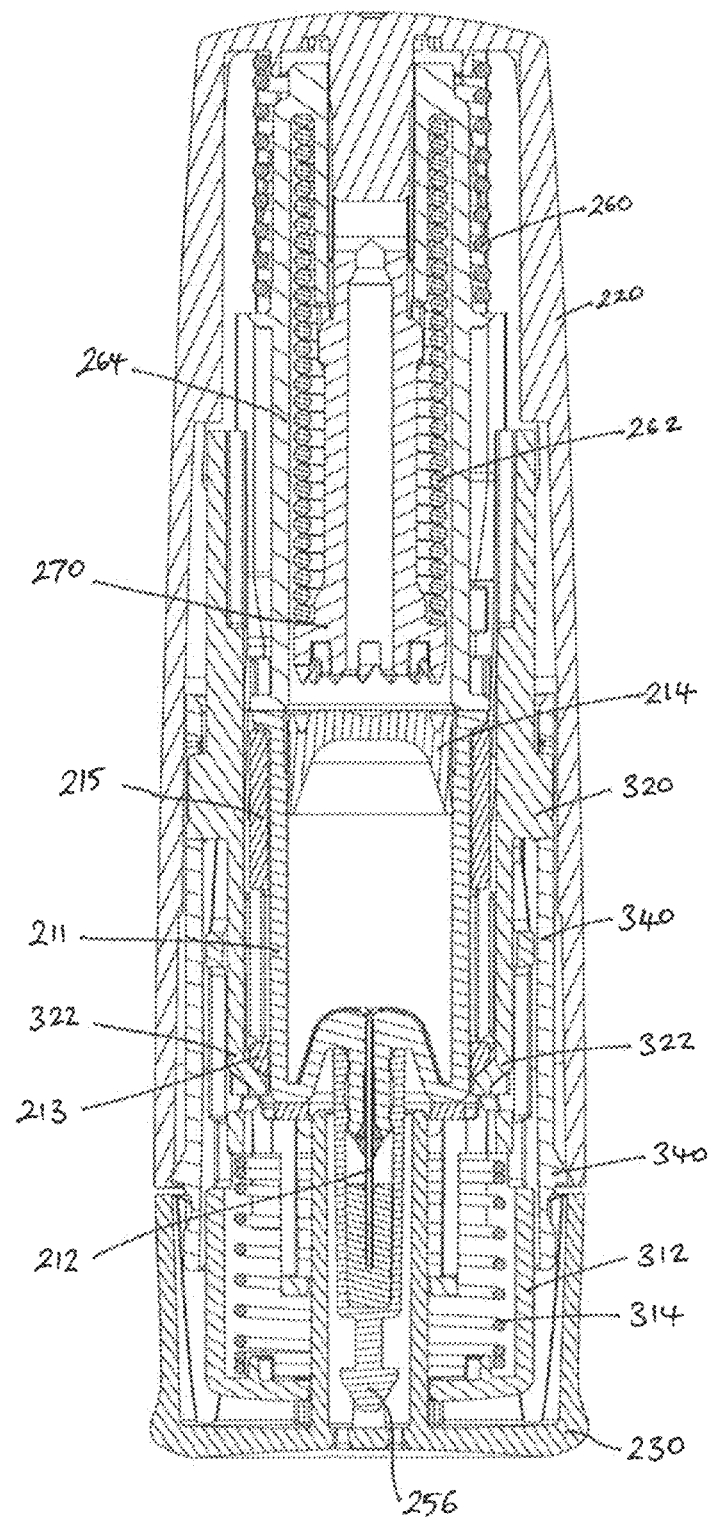
FIG. 20 is a second cross-section through the autoinjector of FIG. 18.

FIG. 19 is a cross-sectional view through the autoinjector 201 of FIG. 19. FIG. 20 is a second cross-sectional view through the autoinjector of FIG. 19, at 90 degrees to the cross-section of FIG. 19.

Figure 26:
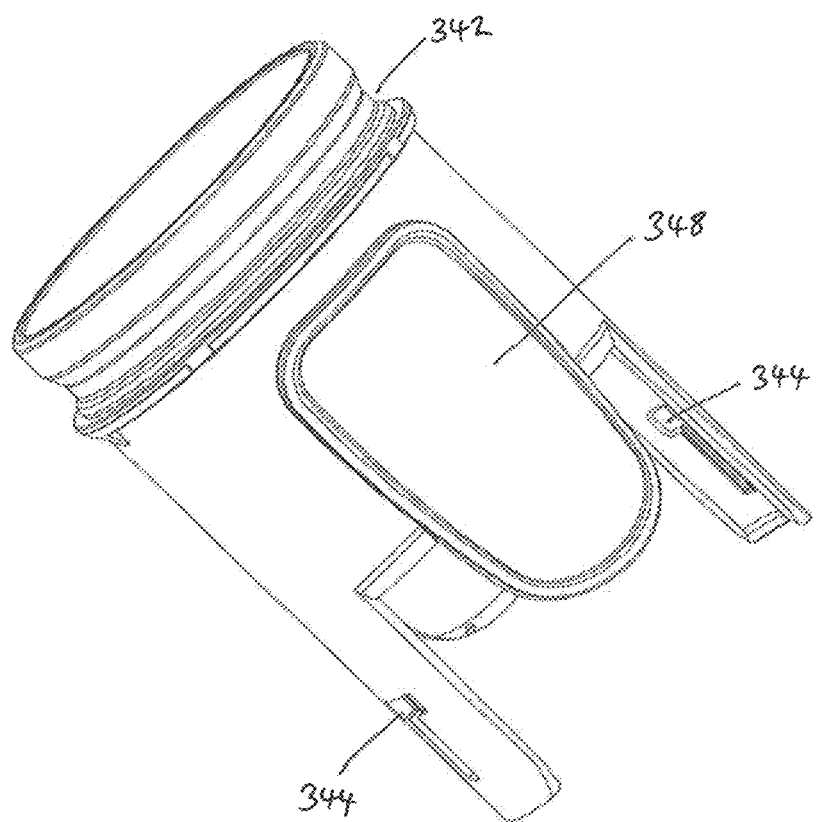
FIG. 26 is a perspective view of the lower housing of the second embodiment.
Figure 27:
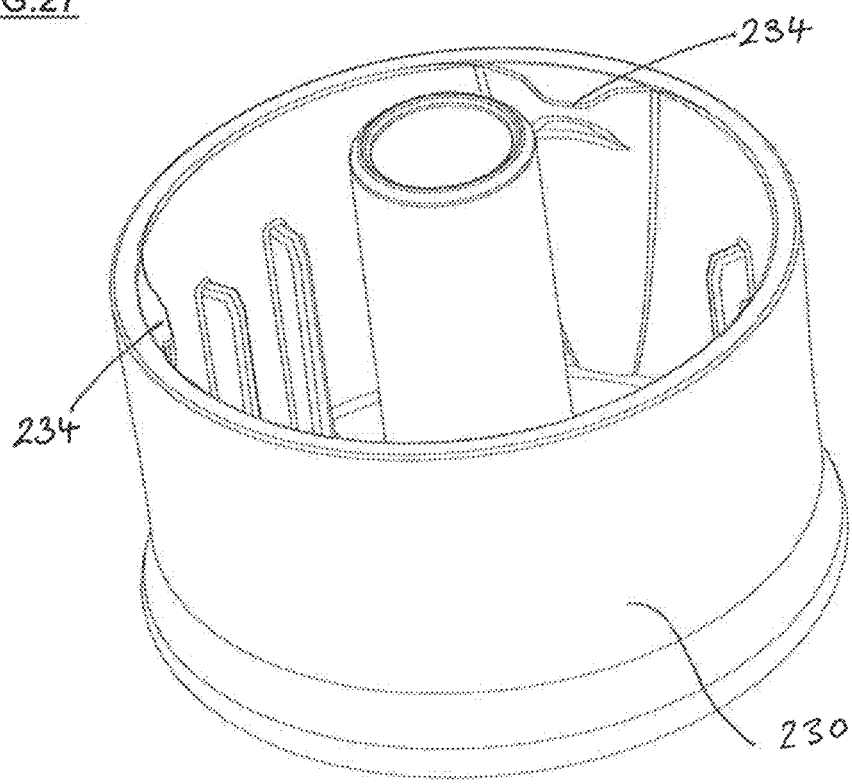
FIG. 27 is a perspective of the cap of the second embodiment.

The autoinjector 201 shown in FIGS. 18, 19 and 20 comprises a drug container assembly (shown in FIG. 21), a powerpack assembly including a powerpack housing 264 (as shown in FIG. 27), a drive member 270 and insertion and drive springs 260, 262, an internal housing (shown in FIG. 23), herein referred to as the chassis, a skin sensor assembly comprising a skin sensor element (shown in FIG. 22) and a skin sensor spring, a lower housing (shown in FIG. 26), an outer housing and a cap (shown in FIG. 25). The drug container assembly 210 is held within the chassis 320 and in operation moves through the chassis. The drug container assembly 210 is retained in an initial position by latches 322 on the chassis, which engage protrusions 213 on the cradle 215 that surrounds the drug container 211. The latches 322 are prevented from releasing the cradle by the skin sensor assembly. The skin sensor assembly comprises a skin sensor element 312 and a skin sensor spring 314. The skin sensor element is held by latching elements 324 on the chassis 320 and urged away from the drug container assembly 210 by the skin sensor spring 314, which is held between the chassis 320 and the skin sensor element 312. The lower housing 340 engages the chassis 320 by clipping to a T-shaped protrusion 328 on the chassis. Window portions 348 on the lower housing engage window 222 formed in the outer housing. The cap 230 engages the channel 342 on the lower housing and covers the skin sensor element 312.

Figure 21:
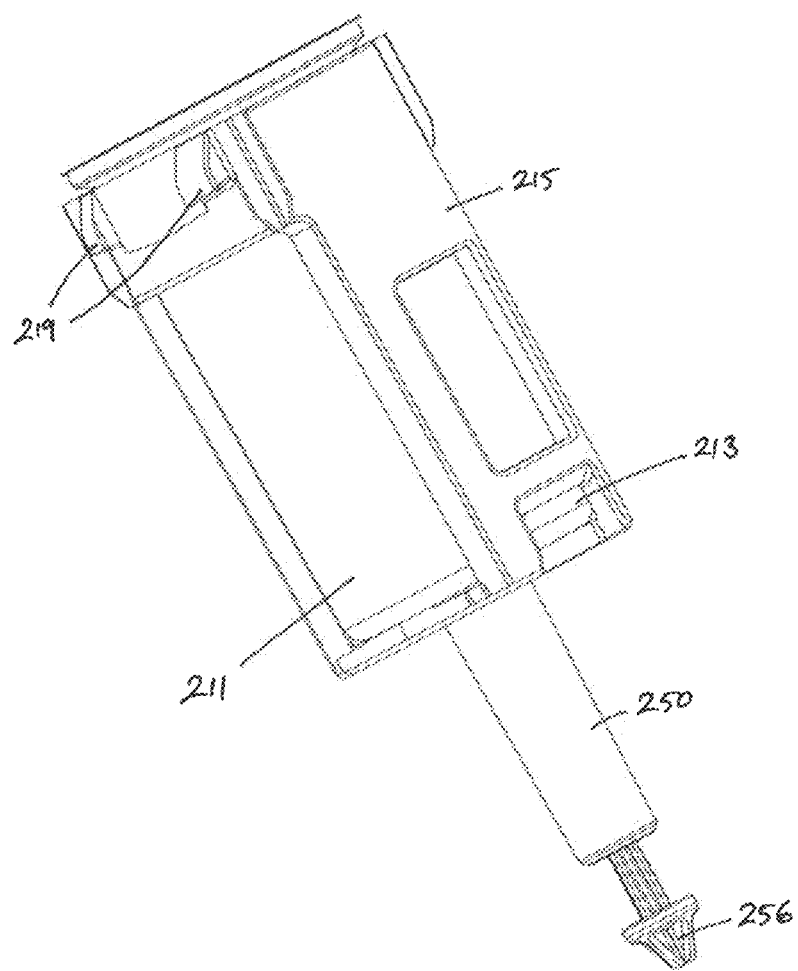
FIG. 21 is a perspective view of the drug container assembly of the second embodiment.

FIG. 21 is a perspective view of the drug container assembly shown in FIGS. 19 and 20. The drug container assembly comprises a drug container 211 and cradle element in which the drug container 211 is held. The cradle and drug container may be formed as separate components or may be co-moulded together. The drug container 211 contains a drug to be delivered to a patient by injection, with a hypodermic needle 212 fixed to a front end. As in the first embodiment, the drug container is formed from cyclic olefin, which has excellent drug contact properties. The cradle may be formed of a different material and advantageously is formed from a mouldable plastic. Clipping features 213 and 219 are formed on the cradle 215.

A plunger 214 is provided within the drug container. Movement of the plunger 214 within the drug container 211 urges the drug out through the needle 212. The plunger is of the same type as described with reference to the first embodiment and is designed to provide low friction with the walls of the drug container and to minimise any stiction between the plunger and the drug container. The internal surface of the front end of the drug container 211 is again shaped to match the shape of the front end of the plunger 214 to maximise the amount of drug that is pushed out of the drug container during use.

A sealing foil 216 is provided at a back end of the drug container 211 to ensure the drug is retained and maintained in a sterile and pristine condition. The sealing foil 216 may be laminated foil including a layer of aluminium and may be welded to a back end of the drug container 211.

As in the first embodiment, the hypodermic needle 212 is glued into a needle hub portion 217 of the drug container 211. However, the drug container may be moulded around the needle. The needle is covered by a needle shield 250 that keeps the needle 212 sterile. As described in the first embodiment, the needle shield 250 comprises a rigid outer housing 252 that forms a seal with the needle hub portion 217. An elastomeric plug 254 is provided within the needle shield into which the front end of the needle 212 is inserted. The elastomeric plug seals the needle and ensures that no drug can escape from the needle prior to removal of the needle shield. The rigid outer housing 252 of the needle shield may be transparent to allow for inspection of the needle during assembly of the autoinjector. The front end of the needle shield outer housing 252 comprises a bulb 256 to engage hooks 232 in the cap 230, as shown in FIG. 19. This ensures that when the cap 230 is removed the needle shield is removed with it.

The sealing of the needle shield to the needle hub is achieved using an interference fit in the same manner as described for the first embodiment and shown in FIG. 5.

As in the first embodiment, the autoinjector shown in FIGS. 18 to 20 comprises an automatic mechanism for inserting the needle into an injection site and for ejecting the drug through the needle into the injection site. The automatic mechanism is referred to herein as the powerpack assembly. The powerpack assembly comprises stored energy sources, in the form of compressed springs 260, 262. When the first spring 260, referred to as the insertion spring, is released it moves the drug container assembly 210 through the housing of the autoinjector to insert the needle 212 into an injection site. The second spring 262, referred to as the delivery spring, is then released to move the plunger 214 through the drug container 211 to inject the drug. The springs 260, 262 and the mechanism for controlling a sequence of release of the springs within the powerpack assembly are positioned rearward of the drug container assembly.

Figure 22:
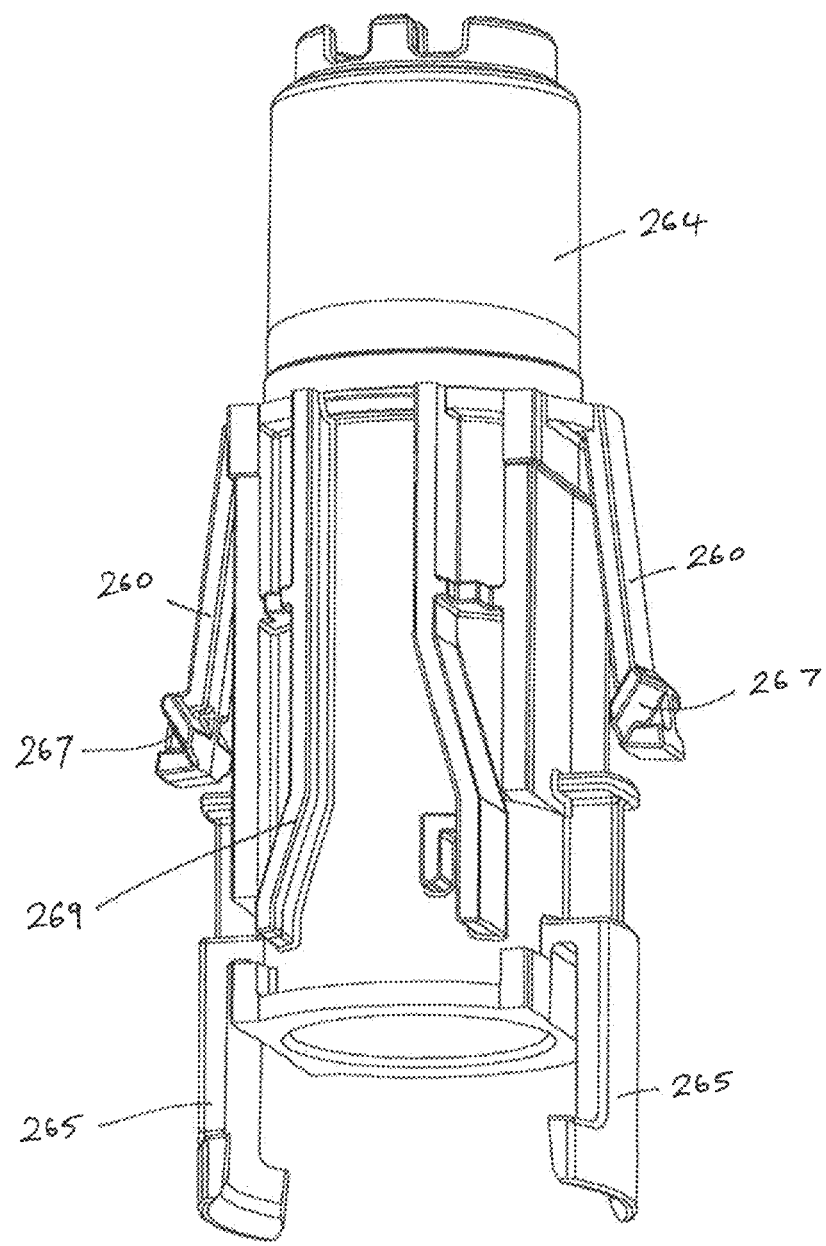
FIG. 22 is a perspective view of the powerpack housing of the second embodiment.

The powerpack comprises a powerpack housing 264, shown in FIG. 22, that is coupled to the drug container assembly 210. The powerpack housing 264 has arms 265 that clip to the features 219 on the cradle 215. The insertion spring 260, shown in FIGS. 19 and 20 in a compressed condition prior to use of the autoinjector, is positioned between the powerpack housing 264 and the outer housing 220. When the drug container assembly is released from the latches 322 on the chassis, the drug container assembly is free to move forward through the chassis to an insertion position, pushed by the expansion of the insertion spring 260, as will be described.

The drive spring 262 is positioned between the powerpack housing 264 and a drive member 270. In an initial position, the drive spring is prevented from expanding by the engagement of protrusions 272 on the drive member 270 with surface 267 on the powerpack housing.

The drive member 270 comprises a front end surface 276 that has a serrations to aid rupture of the sealing foil 216 and which in use engages with the plunger, as will be described. The drive member 270 also has resilient legs 274 that are pressed outwardly by a locking surface 226 that is part of (or rigidly fixed to) the main housing 20 so that protrusions 272 engage with the powerpack housing and are prevented from disengagement with the locking surface 226. In this way the drive spring 262 is locked in a compressed state, and moves with the powerpack housing 264, until the protrusions 272 can be released from the surface 267.

When the powerpack housing has traveled to an insertion position, the drive member has traveled beyond the locking surface 226. At this point, because the locking surface is no longer between the legs 274, the legs 274 can be squeezed together allowing the drive member to disengage from the surface 267 on the powerpack housing. The drive member can then be moved forward by the drive spring 262 to rupture the sealing foil 216 and push the plunger 214 through the drug container 211 to dispense the drug through the needle 212.

As in the first embodiment, in the second embodiment a skin sensor assembly is provided forward of the drug container, which covers the needle both before and after use and which allows the autoinjector to be activated simply by removing a cap and pressing the autoinjector against an injection site.

The skin sensor assembly comprises a skin sensor element 312 and a skin sensor spring 314. The skin sensor spring 314 is held between the skin sensor element and the chassis. This can be seen clearly in FIG. 19. In operation, the skin sensor element interacts with the chassis 320.

FIG. 23 is a perspective view of the skin sensor element of the second embodiment. The skin sensor element comprises a front surface 313 which contacts the injection site in use, and which has an aperture through which the needle passes during insertion of the needle. Apertures 315 are provided so that when the skin senor element is in a retracted position they align with the latches 322 on the chassis, allowing the latches to deflect outwardly out of engagement with features 213, releasing the drug container. Hooks 316 are provided to engage the chassis in an initial position, retaining the skin sensor element against the force applied by the skin sensor spring. Surfaces 317 are provided to abut the chassis and prevent retraction of the chassis when the skin sensor element is in a fully extended position. Bracing arms 318 provide mechanical rigidity.

FIG. 24 is a perspective view of a chassis of the second embodiment. The chassis is formed from a plastics material. The chassis is again essential tubular with a central bore through which the drug container assembly can move axially. The chassis has a front end 332 of reduced diameter beyond which the drug container assembly cannot travel. At the front end, the chassis includes a pair of cantilever arms 334 extending radially inward. The drug container assembly contacts and deflects the cantilever arms in the insertion direction, also referred to as the axial direction herein, as it moves to an insertion position. The deflection of the cantilever arms decelerates the drug container assembly as it reaches the insertion position, reducing force applied to the injection site through the skin sensor spring and skin sensor from the chassis. The cantilever arms 334 are constructed to extend rearward from their fixed end to their free end so that they can deflect before being level with the rest of the front end of the chassis.

Figure 25A:
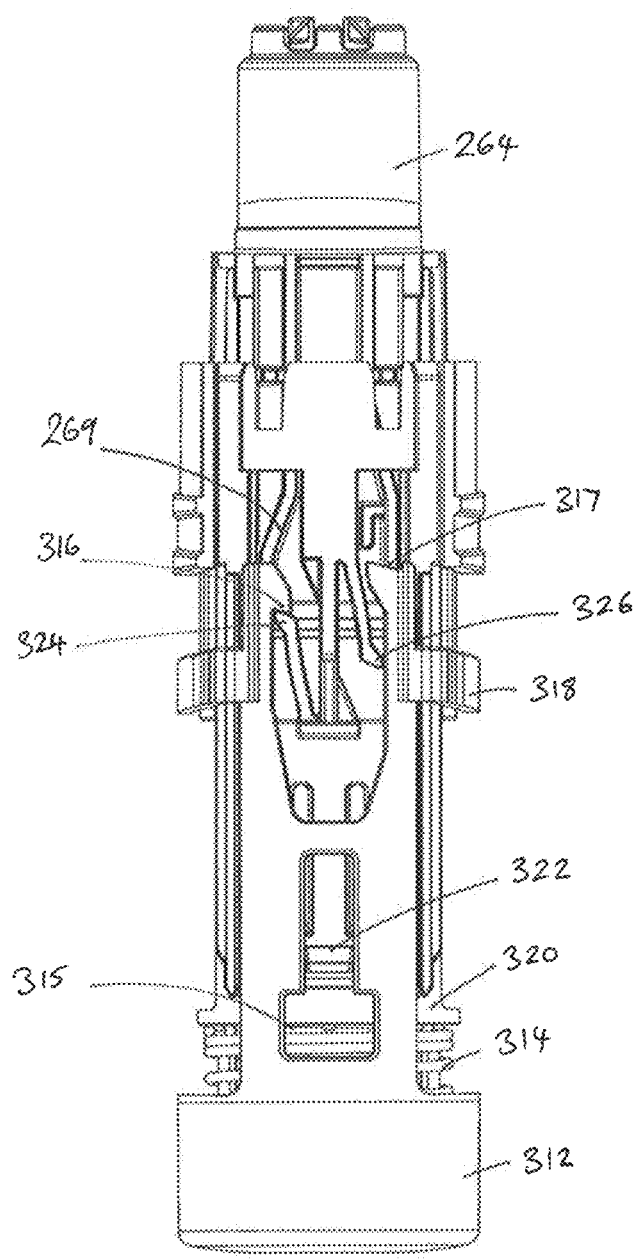
FIGS. 25a to 25c are side views of the skin sensor element, chassis and powerpack housing showing the sequence of movement of the skin sensor element during use.
Figure 25B:
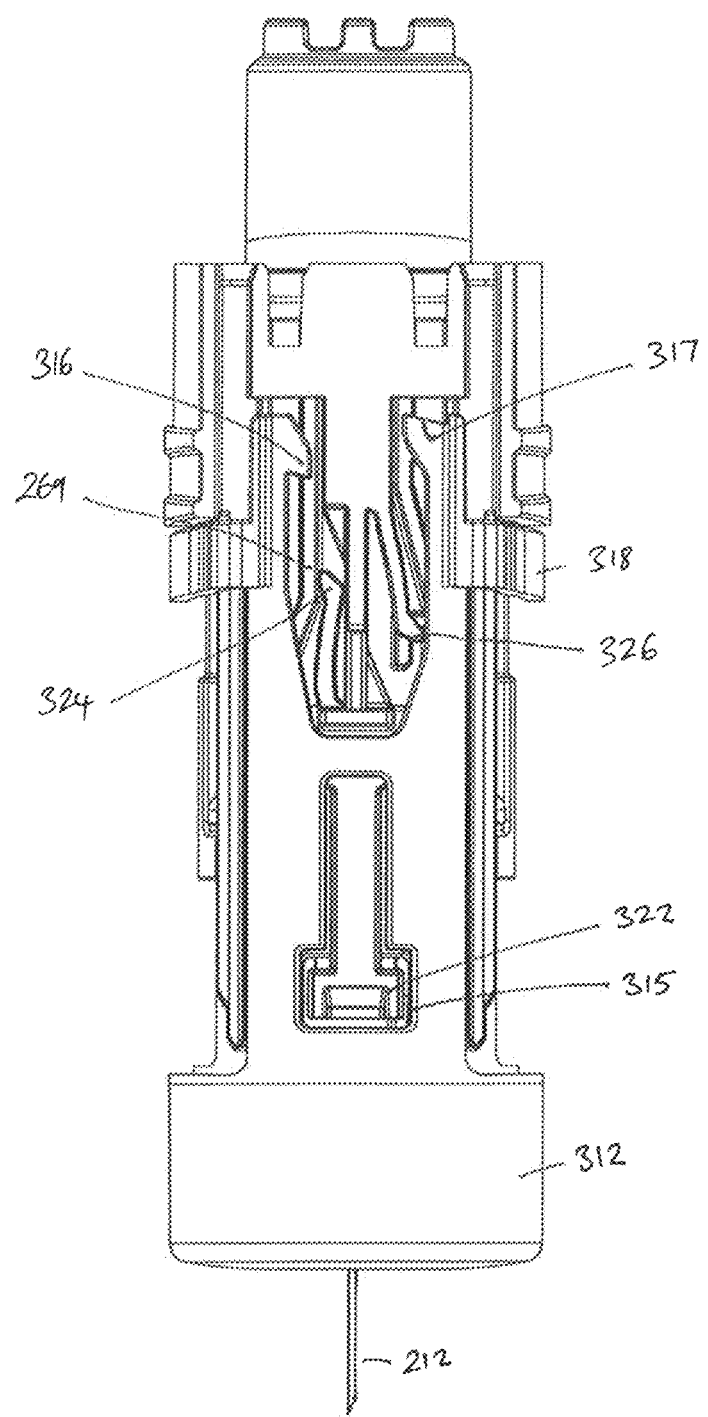
Figure 25C:
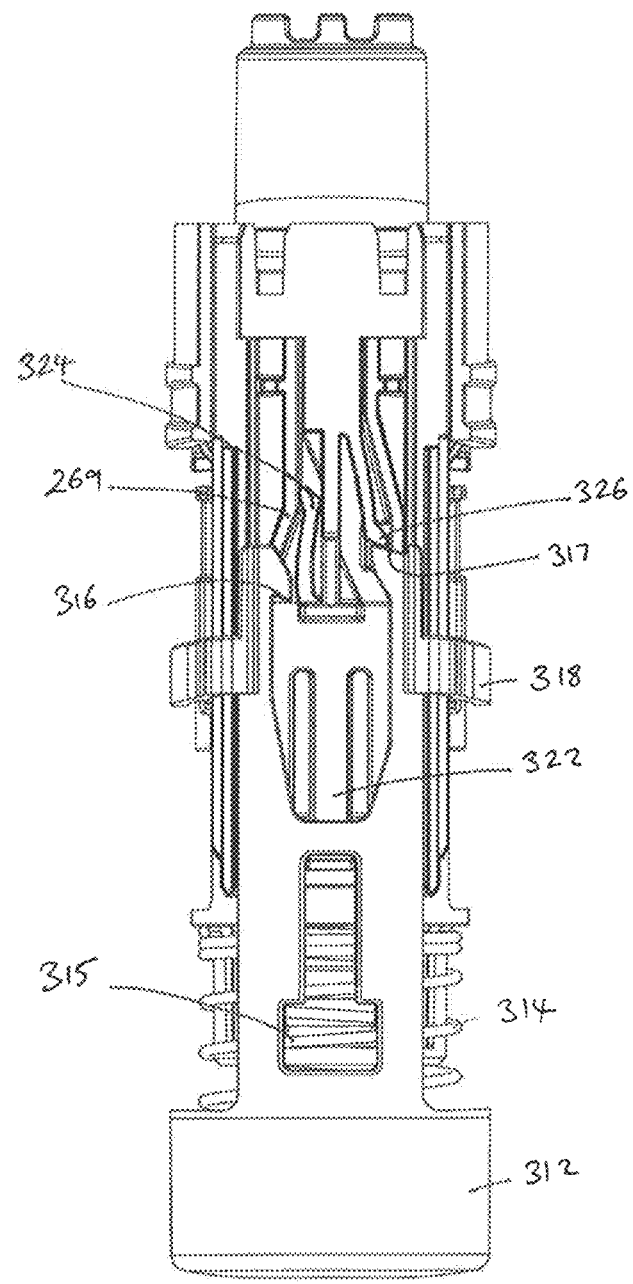

The chassis comprises latching elements 324 that engage hooks 316 on the skin sensor element. The latching elements 324 are resilient arms that extend rearward from their fixed end but at an angle offset from the axial direction. The latching elements can be deflected by camming features 269 on the powerpack assembly to allow the hooks 316 to pass as the skin sensor moves to an extended position. The chassis comprises locking arms 326, which are resilient arms that extend forward from their fixed end. The locking arms can flex to allow the skin sensor element to pass when the skin sensor moves from a retracted position to an extended position, but are configured to prevent the surfaces 317 from passing back over the locking arms 326 once the skin senor has reached the fully extended position. FIGS. 25a-25c show the sequence of operation of the skin sensor assembly, and are side views of the device with the outer housing and cap removed. FIG. 25a shows the device prior to use. The skin sensor element 312 is retained against the action of the skin sensor spring by the latching element 324. Specifically hook 316 on the skin sensor element engages the latching element 324.

FIG. 25b shows the skin sensor element 312 pushed back, as it would be if the skin sensor element were pressed against an injection site, and the powerpack moved forward. In this position, the hook 316 is clear of the surface latching element 324. The apertures 315 are now aligned with the position of latches 322 on the chassis. In the position shown in FIG. 25b, the latches 322 no longer retain the drug container assembly 210, as they can be pushed outwards into the apertures 315 in the skin sensor element. Accordingly, the drug container 311 has moved forward and the insertion spring 261 expanded to move the powerpack assembly and drug container to an insertion position.

As the powerpack assembly moves forward to the insertion position, camming ridge 269 engages the latching elements 324 to deflect the latching elements so that they extend in an axial direction, as shown.

When the device is removed from the injection site, the skin sensor spring 314 urges the skin sensor element 312 forward. As the latching arms 324 are deflected, the hooks 316 can pass the latching elements 324 as the skin sensor element moves forward. The skin sensor element 312 can then move to a fully extended position as shown in FIG. 25c. In this position, the skin sensor element covers the needle again. The skin sensor element is retained to the chassis and prevented from further forward movement by the engagement of bracing arms 318 with a portion of the lower housing 340 (not shown in FIG. 25c). The locking arms 326 flex to allow the skin sensor element to pass when the skin sensor moves from a retracted position to an extended position, but surfaces 317 then engage the locking arms 326 if the skin sensor element is pushed back towards a retracted position, locking the skin sensor element in the extended position.

FIG. 26 is a perspective view of the lower housing of the second embodiment. The lower housing 340 is formed from a transparent plastics material and includes window portions 348. The lower housing fits over the skin sensor and chassis but partially within the outer housing. Window portions 348 have raised outer rims that and engage windows 222 formed in the outer housing. The lower housing 340 engages the chassis 320 by apertures 344 receiving T-shaped protrusions 328 on the chassis Channel 342 on the lower housing is provided to engage the cap 330.

FIG. 27 is a perspective of the cap of the second embodiment. The cap 230 comprises a central cylindrical tube portion comprising three angularly spaced, inwardly projecting hooks 232, shown in FIG. 19, that can be pushed over and engage the bulb 256 on the needle shield 250. This ensures that the needle shield is removed with the cap when the device is to be used. The cap also comprises three inwardly projecting lugs 234, equally spaced around the circumference on the cap, that are configured to engage the lower housing 340. To remove the cap, a user simply grips and squeezes the cap between two fingers and pulls the cap away from the lower housing. The use of three, equally spaced lugs ensures that when the cap is radially squeezed by a user, at least two of the lugs will move outwardly to disengage from the lower housing, whatever direction the cap is squeezed in. This ensures that the cap can be easily removed.

Figure 28A:
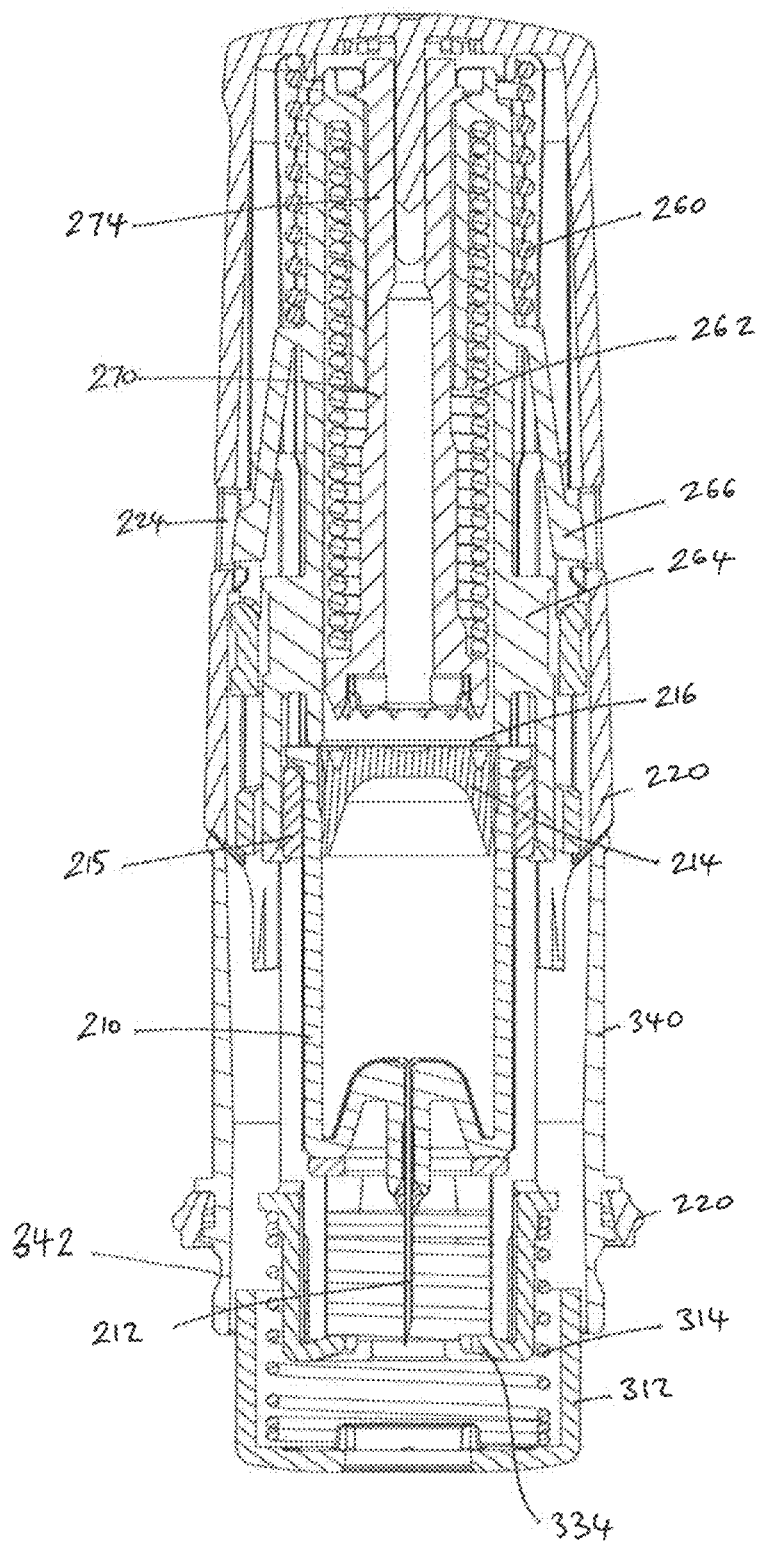
FIGS. 28a to 28e are cross-section views of the second embodiment, illustrating the sequence of operation.

FIGS. 28a to 28e are cross-section views of the second embodiment, illustrating the sequence of operation. FIG. 28a shows the device immediately after cap removal, but prior to the pressing of the skin sensor element against an injection site. It can be seen that the needle shield assembly has been removed together with the cap.

Figure 28B:
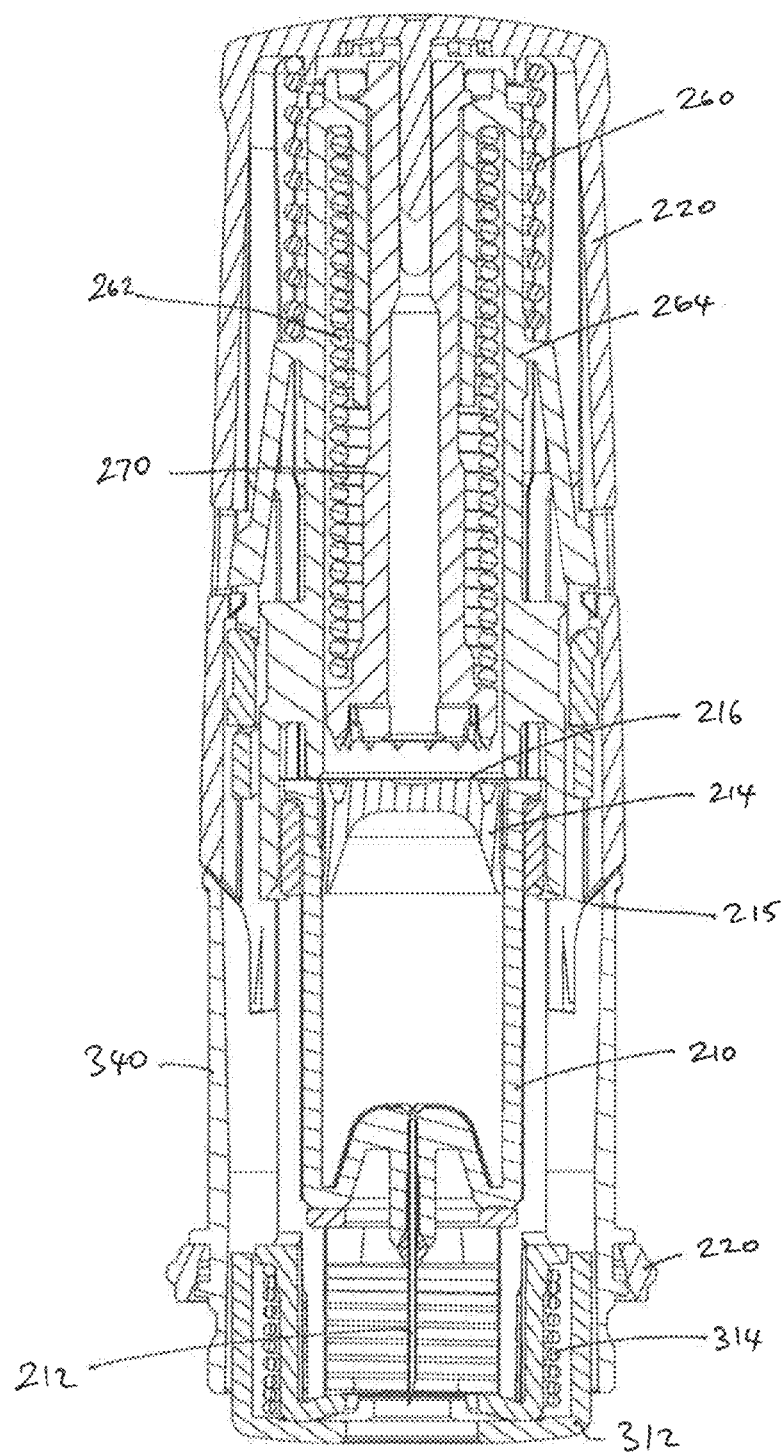

FIG. 28b shows the device with the skin sensor 312 element pushed back, compressing the skin sensor spring 314. The bracing arms 318 on the skin sensor element abut the chassis to prevent the skin sensor element from moving further back. In this position, the latches 322 on the chassis are free to bend out into the windows 315.

Figure 28C:
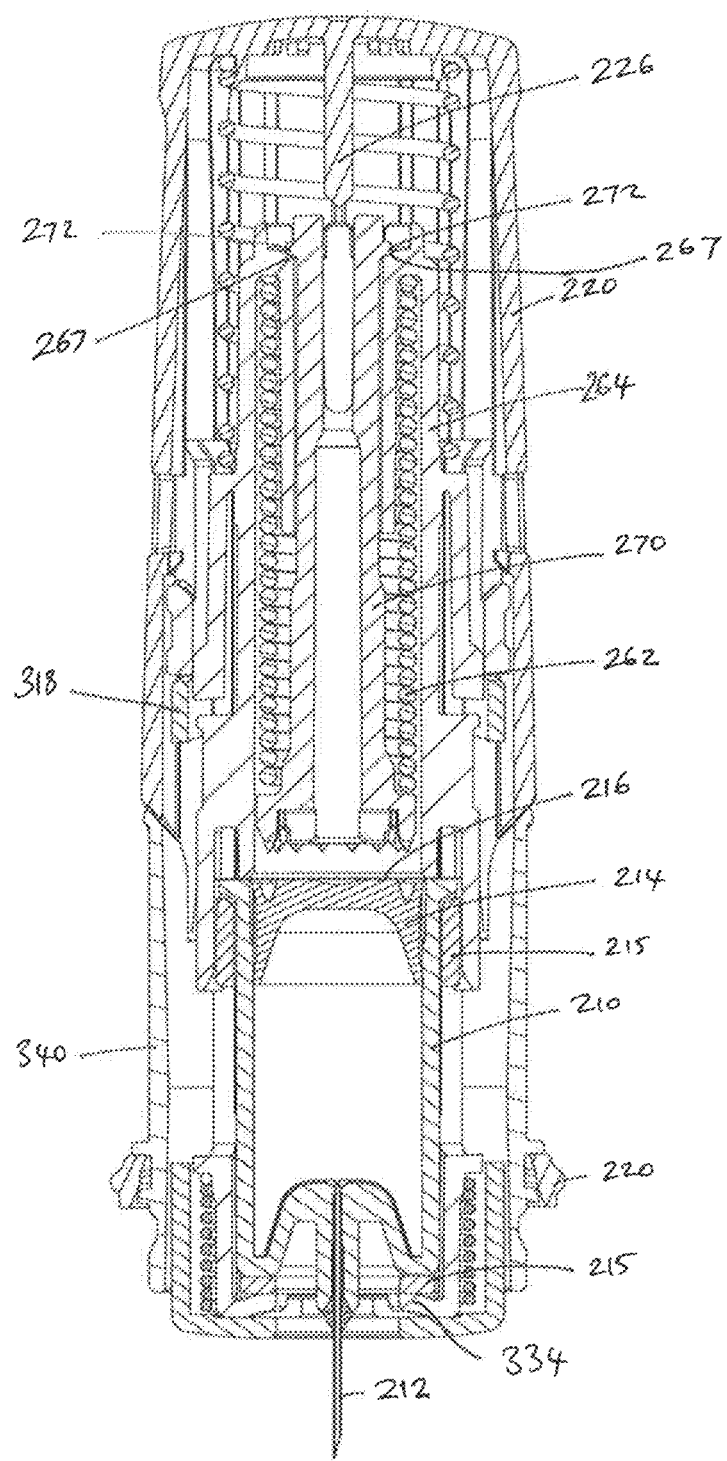

FIG. 28c shows the drug container 211 and powerpack housing 264 moved to an insertion position by the expansion of insertion spring 261. In this position, the needle 212 is inserted into the injection site. The drive member 270 is just clear of the locking surface 226 on the outer housing. This means that legs 274 can be squeezed together to disengage the lugs 272 from surface 267 on the powerpack housing 264. The drive spring 262 is free to expand. The camming protrusions 269 on the powerpack housing have deflected the latching elements 324 so that the skin sensor element 312 is free to move forward to a fully extended position once it is removed from the injection site.

Figure 28D:
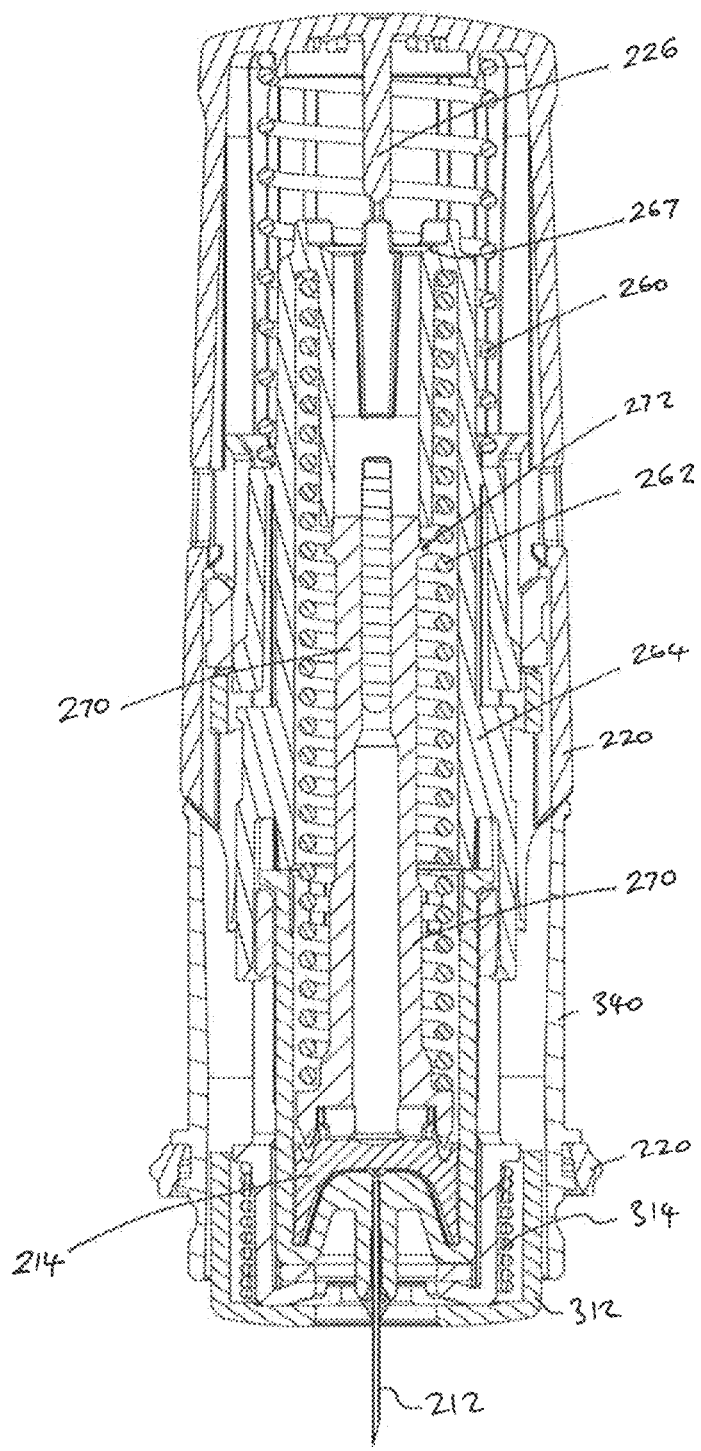

FIG. 28d shows the drive spring 262 expanded. The sealing foil 216 has been ruptured and the plunger 214 has been moved through the drug container and the drug has been ejected.

Figure 28E:
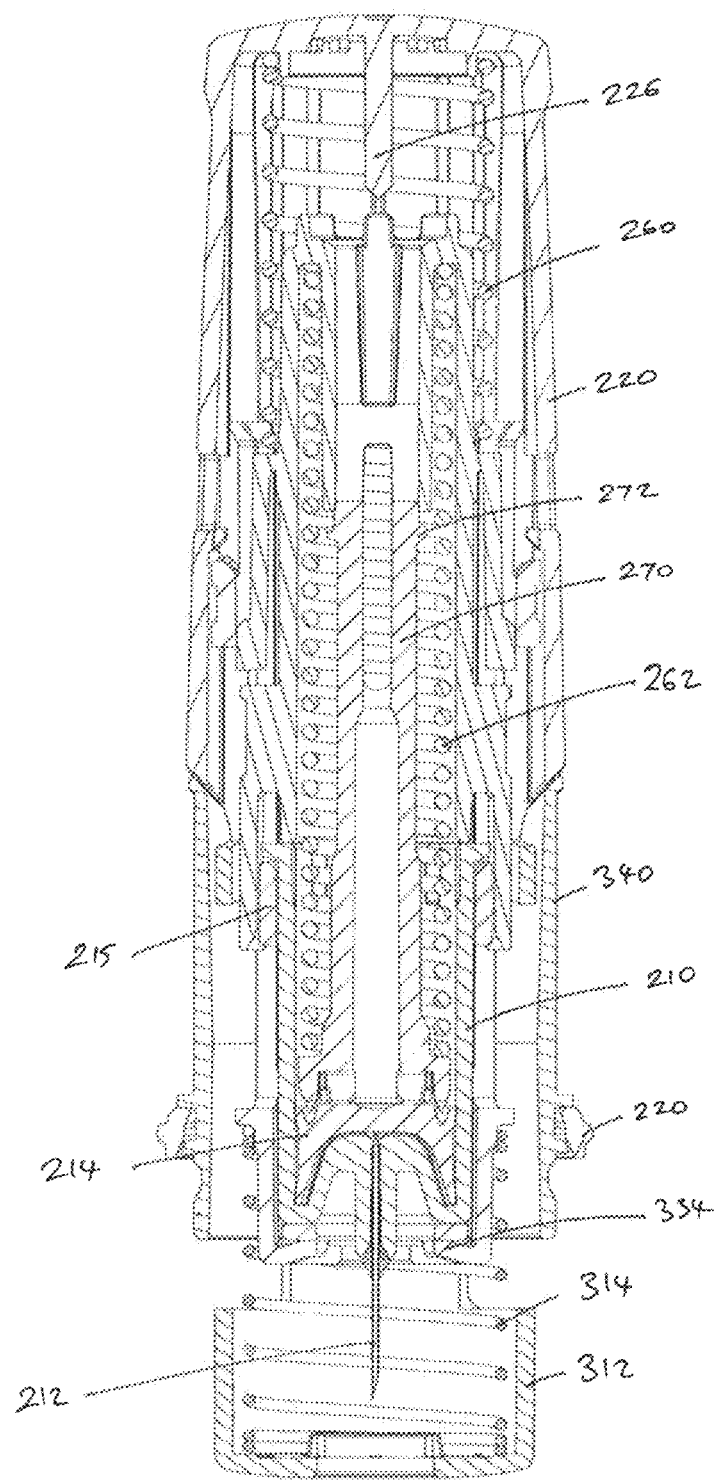

FIG. 28e shows the device after it has been removed from the injection site, with the skin sensor element in a fully extended position, locked and covering the needle. The skin sensor element is retained to the chassis and prevented from further forward movement by the engagement of bracing arms 318 with a portion of the lower housing 340. The locking arms 316 have flexed to allow the skin sensor element to pass as the skin sensor to the extended position, but surfaces 317 lock the skin sensor element in the extended position, preventing any retraction of the skin sensor element.

Figure 29:
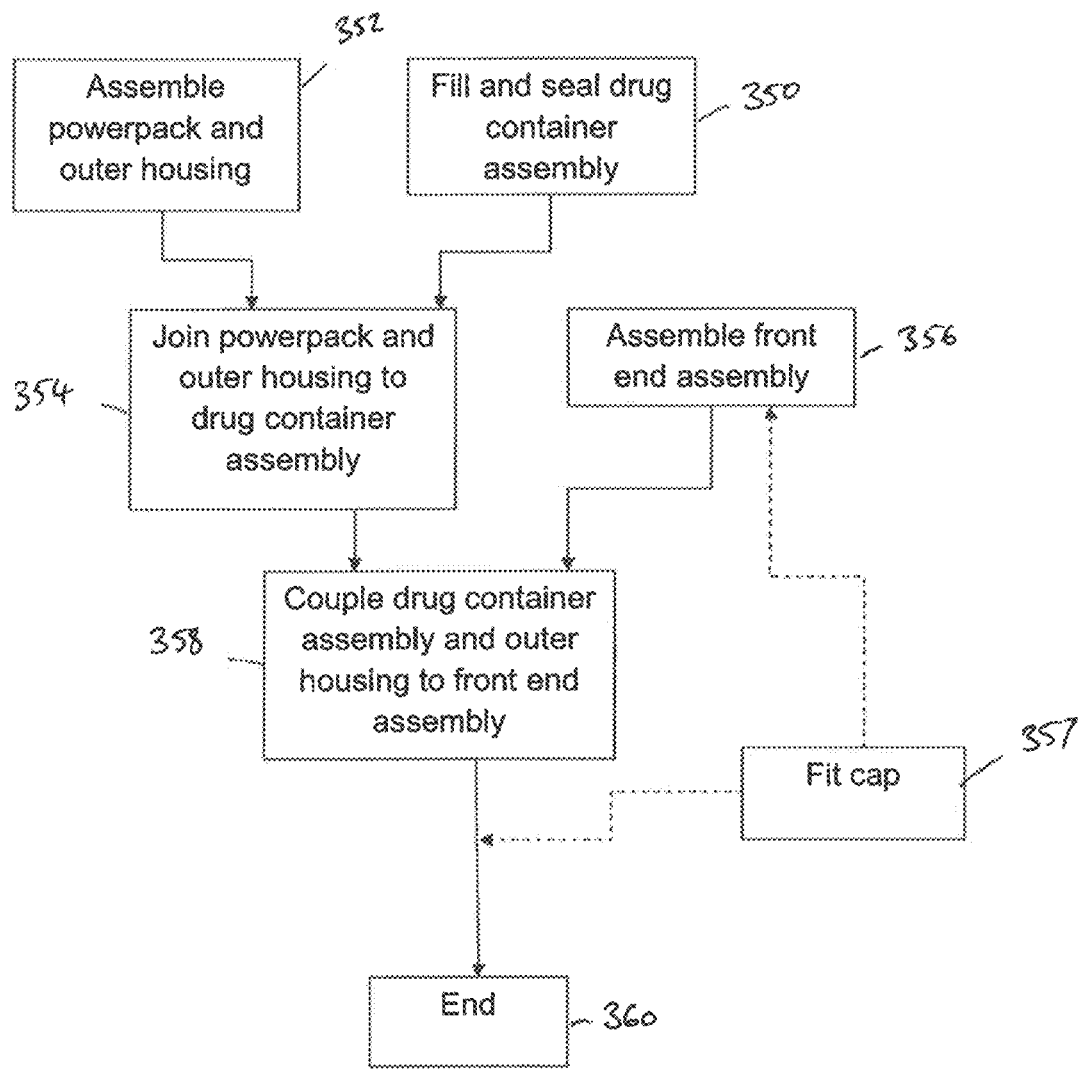
FIG. 29 is a schematic diagram illustrating the assembly process of an autoinjector in accordance with the second embodiment of the invention.

FIG. 29 is a schematic diagram illustrating the assembly process of an autoinjector in accordance with the second embodiment of the invention. In step 350, the drug container assembly 210, including the needle 212 and needle shield 250 is filled with dose of drug and a plunger 214, and then sealed by a sealing foil 216. This is carried out in a sterile environment. Independently, in step 352 the powerpack assembly is assembled to the outer housing. In step 354 the filled drug container assembly is then fitted to the powerpack assembly. The front end of the device, including the chassis, skin sensor element, skin sensor spring, and lower housing is assembled in step 356. The powerpack housing includes locking arms 266, which are received in openings 224 in the outer housing to retain the insertion spring in a first compressed state. The locking surface 226 engages the drive member 270 to hold the drive spring in a compressed state.

Figure 30:
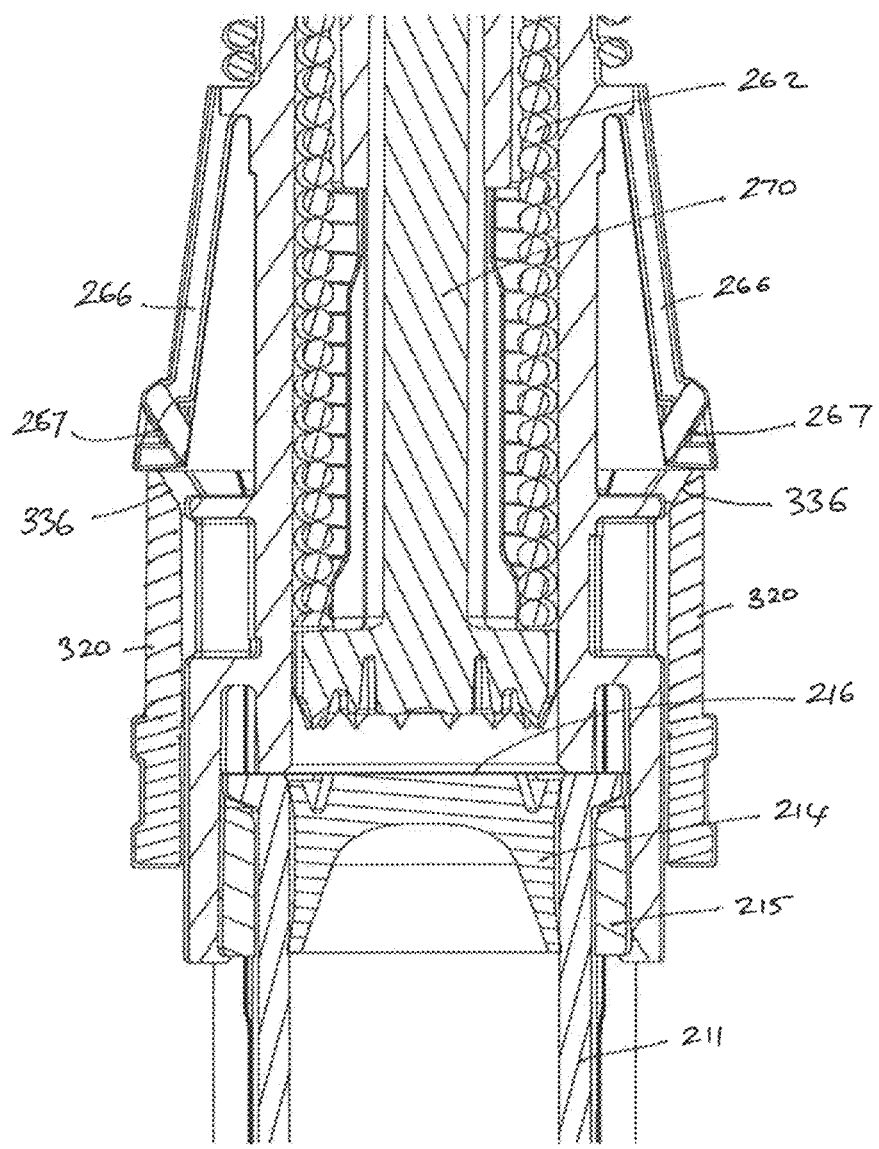
FIG. 30 illustrates the mechanism by which the powerpack is disengaged from the outer housing as it engages the chassis.

In step 358, the front end assembly is coupled to the drug container assembly and the powerpack assembly and outer housing. The drug container assembly is retained by latching arms on the chassis. The window portions 348 of the lower housing clip into to the windows 222 of the outer housing. As the lower housing is moving towards an engaged position in which the window portions are fully engaged with the windows on the outer housing, the chassis 320 engages the arms 266 on the powerpack housing to move them out of the openings 224. This mechanism is illustrated in FIG. 30.

The chassis includes cam surfaces 336 at its rear end that engage corresponding cam surfaces 267 on the locking arms 266. As the chassis and powerpack move toward one other, the cam surfaces 267 on the chassis deflect locking arms inwardly and out of engagement with the outer housing 220. At this point, the insertion spring 260 is allowed to expand a small amount, but it is subsequently held in a second compressed state as soon as the lower housing 340 engages the outer housing. The latches 322 on the chassis engage the drug container assembly 210, the chassis 320 is fixed to the lower housing and the lower housing is fixed to the outer housing. Accordingly, the insertion spring cannot expand until the latches 322 are released from the drug container. In the second compressed state, the insertion spring still stores enough energy to insert the needle 12 into an injection site by pushing the drug container to the insertion position when the latches 322 are released. The components are configured so that the disengagement of the locking arms 266 from the outer housing happens only momentarily before the window portions 348 lock to the window 222.

The cap 30 is typically assembled to the lower housing 340 during assembly of the front end assembly, but may be added after the powerpack and front assembly are joined or after the outer housing has been fitted to the lower housing. These options are illustrated in FIG. 29 as step 357. Also, as an alternative to the process illustrated in FIG. 29, the drug container assembly could be assembled to the front end assembly before being coupled to the powerpack and outer housing. The assembly process is complete at step 360.

What is claimed is:

1. A drug delivery device comprising:
    a housing;
    a drug container within the housing and containing a drug to be dispensed, the drug container having a first end defining a first opening, a second opening through which the drug is dispensed in use, and at least one side wall extending between the first opening and the second opening;
    a plunger, positioned within the drug container, in contact with the drug;
    a first sealing element providing a first closure seal across the first opening of the drug container;
    a pusher initially located on an opposite side of the first closure seal to the plunger, wherein the pusher is operable to break the first closure seal and move the plunger within the drug container to dispense the drug; and
    an insertion mechanism configured to contact the at least one side wall of the drug container to move the drug container through the housing,
    wherein, prior to use, the pusher and the insertion mechanism are held out of contact with the first sealing element.

2. The drug delivery device according to claim 1, wherein the plunger is a cup seal type plunger, configured such that a component of a fluid pressure exerted by the drug on the plunger as the plunger is moved through the drug container is directed towards a sealing interface between the plunger and an internal surface of the drug container.

3. The drug delivery device according to claim 1, wherein a peripheral portion of the plunger in contact with a wall of the drug container comprises a substantially non-elastomeric material.

4. The drug delivery device according to claim 1, wherein the first sealing element provides a sterile seal.

5. The drug delivery device according to claim 1, wherein the pusher comprises one or more piercing elements or serrations on a seal contact surface, configured to pierce the first sealing element during operation of the device.

6. The drug delivery device according to claim 1, wherein the device is an autoinjector.

7. A drug delivery device comprising:
a housing;
a drug container within the housing and containing a drug to be dispensed, the drug container having a first end defining a first opening;
a plunger, positioned within the drug container, in contact with the drug;
a first sealing element providing a first closure seal across the first opening of the drug container;
a pusher initially located on an opposite side of the first closure seal to the plunger, wherein the pusher is operable to break the first closure seal and move the plunger within the drug container to dispense the drug; and
an insertion mechanism configured to move the drug container through the housing prior to operation of the pusher to break the first closure seal,
wherein no elements of the insertion mechanism and housing contact the first sealing element as the drug container is moved through the housing.

8. The drug delivery device according to claim 7, wherein the device is an autoinjector.

9. A drug delivery device, comprising:
a drug container;
an internal housing;
an insertion mechanism coupled to the drug container and configured to move the drug container through the internal housing in an insertion direction;
a skin contact element, configured to contact an injection site in use; and
a skin contact biasing element biasing the skin contact element in the insertion direction relative to the internal housing;
wherein the skin contact element is movable relative to the internal housing in a direction opposite to the insertion direction from an initial position to a retracted position to trigger the insertion mechanism;
wherein the internal housing includes a first latching element to restrain the skin contact element from moving from the initial position in the insertion direction, wherein the first latching element comprises a latching surface to engage the skin contact element and a first camming surface; and
wherein either the drug container or the insertion mechanism includes a second camming surface, wherein the second camming surface is configured to engage the first camming surface to move the first latching element as the drug container is moved through the internal housing, thereby allowing the skin contact element to move in the insertion direction past the initial position to an extended position.

10. The drug delivery device according to claim 9, wherein the first latching element comprises a resilient cantilever arm, wherein the latching surface and the first camming surface are formed at a free end of the resilient cantilever arm.

11. The drug delivery device according to claim 10, wherein the resilient cantilever arm is held in tension by the skin contact element and the skin contact biasing element when the skin contact element is in the initial position.

12. The drug delivery device according to claim 9, wherein the internal housing defines a central bore through which the drug container moves, and wherein the first and second camming surfaces are configured to move the first latching element in a direction parallel to a perimeter of the bore.

13. The drug delivery device according to claim 12, wherein the first camming surface is positioned inwardly of the latching surface.

14. The drug delivery device according to claim 9, wherein the first camming surface extends non-parallel with the latching surface.

15. The drug delivery device according to claim 9, wherein the skin contact element comprises at least a first aperture that aligns with a drug container latch on the internal housing when the skin contact element is in the retracted position.

16. The drug delivery device according to claim 9, wherein the skin contact element is configured so as not to occlude a window in the internal housing for viewing the drug container when in the initial or retracted position.

17. The drug delivery device according to claim 9, further comprising a second latching element formed on the internal housing, the second latching element being configured to prevent the skin contact element moving to the retracted position after it has been released from the first latching element.

18. The drug delivery device according to claim 17, wherein the second latching element engages an aperture or a protrusion on the skin contact element.

19. The drug delivery device according to claim 9, wherein in the retracted position the skin contact element abuts the internal housing.

* * * * *